(12) United States Patent
Sakurada et al.

(10) Patent No.: US 9,714,433 B2
(45) Date of Patent: *Jul. 25, 2017

(54) HUMAN PLURIPOTENT STEM CELLS INDUCED FROM UNDIFFERENTIATED STEM CELLS DERIVED FROM A HUMAN POSTNATAL TISSUE

(71) Applicant: Kyoto University, Kyoto (JP)

(72) Inventors: Kazuhiro Sakurada, Kanagawa (JP); Tetsuya Ishikawa, Tokyo (JP); Hideki Masaki, Tokyo (JP); Shunichi Takahashi, Hyogo (JP)

(73) Assignee: KYOTO UNIVERSITY, Kyoto (JP)

( * ) Notice: Subject to any disclaimer, the term of this patent is extended or adjusted under 35 U.S.C. 154(b) by 217 days.

This patent is subject to a terminal disclaimer.

(21) Appl. No.: 14/195,698

(22) Filed: Mar. 3, 2014

(65) Prior Publication Data

US 2014/0206083 A1    Jul. 24, 2014

Related U.S. Application Data

(62) Division of application No. 12/663,840, filed as application No. PCT/EP2007/010019 on Nov. 20, 2007, now abandoned.

(30) Foreign Application Priority Data

Jun. 15, 2007   (JP) ................................ 2007-159382

(51) Int. Cl.
*C12N 5/074* (2010.01)
*C12N 15/85* (2006.01)

(52) U.S. Cl.
CPC ........... *C12N 15/85* (2013.01); *C12N 5/0696* (2013.01); *C12N 2501/602* (2013.01); *C12N 2501/603* (2013.01); *C12N 2501/604* (2013.01); *C12N 2501/606* (2013.01); *C12N 2510/00* (2013.01); *C12N 2799/027* (2013.01)

(58) Field of Classification Search
CPC ........... C12N 5/0696; C12N 2501/602; C12N 2501/603; C12N 2501/604; C12N 2501/606; C12N 2510/00; C12N 15/85; C12N 2501/605; C12N 2501/608; C12N 15/63; C12N 2799/027; C12N 2501/60; C12N 15/86; C12N 2506/45; C12N 2501/727; C12N 2506/1307; C12N 5/0657; C12N 5/0678; C12N 5/0606; A61K 35/545

See application file for complete search history.

(56) References Cited

U.S. PATENT DOCUMENTS

| | | |
|---|---|---|
| 4,650,764 A | 3/1987 | Temin et al. |
| 4,861,719 A | 8/1989 | Miller |
| 4,937,190 A | 6/1990 | Palmenberg et al. |
| 5,225,348 A | 7/1993 | Nagata et al. |
| 5,266,491 A | 11/1993 | Nagata et al. |
| 5,268,290 A | 12/1993 | Hasegawa et al. |
| 5,288,514 A | 2/1994 | Ellman |
| 5,324,645 A | 6/1994 | Takahara et al. |
| 5,449,614 A | 9/1995 | Danos et al. |
| 5,519,134 A | 5/1996 | Acevedo et al. |
| 5,525,735 A | 6/1996 | Gallop et al. |
| 5,549,974 A | 8/1996 | Holmes |
| 5,591,624 A | 1/1997 | Barber et al. |
| 5,637,456 A | 6/1997 | Roth et al. |
| 5,652,122 A | 7/1997 | Frankel et al. |
| 5,674,980 A | 10/1997 | Frankel |
| 5,707,618 A | 1/1998 | Armentano et al. |
| 5,716,832 A | 2/1998 | Barber et al. |
| 5,744,320 A | 4/1998 | Sherf et al. |
| 5,817,491 A | 10/1998 | Yee et al. |
| 5,817,492 A | 10/1998 | Saito et al. |
| 5,830,725 A | 11/1998 | Nolan et al. |
| 5,834,256 A | 11/1998 | Finer et al. |
| 5,858,740 A | 1/1999 | Finer et al. |
| 5,910,434 A | 6/1999 | Rigg et al. |
| 5,955,331 A | 9/1999 | Danos et al. |

(Continued)

FOREIGN PATENT DOCUMENTS

| | | |
|---|---|---|
| AU | 2008201280 A1 | 4/2008 |
| CN | 101250502 A | 8/2008 |

(Continued)

OTHER PUBLICATIONS

Perkins et al. Anemia and perinatal death result from loss of the murine ecotropic retrovirus receptor mCAT-1.Genes & Development, 1997, vol. 11, pp. 914-925.*
A reprogramming rush. Editorial. Nature. Mar. 27, 2008. 452:388. Published online Mar. 26, 2008.
Adachi et al. Role of SOX2 in maintaining pluripotency of human embryonic stem cells. Genes Cells. May 2010; 15(5):455-70.
Adewumi et al., Characterization of Human Embryonic Stem Cell Lines by the International Stem Cell Initiative, Nat. Biotechnol. 25(7):803-16, 2007.
Adhikary et al. Transcriptional regulation and transformation by Myc proteins. Nat Rev Mol Cell Biol. Aug. 2005;6(8):635-45.
Akimov et al., Bypass of Senescence, Immortalization, and Transformation of Human Hematopoietic Progenitor Cells, Stem Cells 23:1423-33, 2005.

(Continued)

*Primary Examiner* — Thaian N Ton
(74) *Attorney, Agent, or Firm* — Knobbe, Martens, Olson & Bear LLP

(57) ABSTRACT

Establishment of human pluripotent stem cells having properties close to human ES cells with the genome of the patient per se that can circumvent immunological rejection of transplanted cells from cells derived from a postnatal human tissue are described. Human pluripotent stem cells can be induced by introducing three genes of Oct3/4, Sox2 and Klf 4, or three genes of Oct3/4, Sox2 and Klf 4 plus the c-Myc gene or a histone deacetylase (HDAC) inhibitor of undifferentiated stem cells present in various human postnatal tissues in which each gene of Tert, Nanog, Oct3/4 and Sox2 has not undergone epigenetic inactivation.

2 Claims, 22 Drawing Sheets

(56) References Cited

U.S. PATENT DOCUMENTS

| | | |
|---|---|---|
| 6,013,517 A | 1/2000 | Respess et al. |
| 6,017,735 A | 1/2000 | O'hare |
| 6,017,761 A | 1/2000 | Rigg et al. |
| 6,025,192 A | 2/2000 | Beach et al. |
| 6,140,111 A | 10/2000 | Riviere et al. |
| 6,146,874 A | 11/2000 | Zolotukhin et al. |
| 6,153,432 A | 11/2000 | Halvorsen et al. |
| 6,153,745 A | 11/2000 | Williams et al. |
| 6,203,975 B1 | 3/2001 | Wilson et al. |
| 6,251,398 B1 | 6/2001 | O'Hare et al. |
| 6,255,071 B1 | 7/2001 | Beach et al. |
| 6,312,948 B1 | 11/2001 | Cohen-haguenauer |
| 6,312,949 B1 | 11/2001 | Sakurada et al. |
| 6,333,195 B1 | 12/2001 | Respess et al. |
| 6,365,352 B1 | 4/2002 | Yerramilli et al. |
| 6,395,546 B1 | 5/2002 | Zobel et al. |
| 6,451,595 B1 | 9/2002 | Kim et al. |
| 6,485,959 B1 | 11/2002 | Demetriou et al. |
| 6,521,453 B1 | 2/2003 | Crameri et al. |
| 6,521,455 B2 | 2/2003 | O'Hare et al. |
| 6,605,275 B1 | 8/2003 | Boyse et al. |
| 6,660,514 B1 | 12/2003 | Zolotukhin et al. |
| 6,773,920 B1 | 8/2004 | Dalby et al. |
| 6,833,269 B2 | 12/2004 | Carpenter |
| 6,835,567 B1 | 12/2004 | Sah et al. |
| 6,841,535 B2 | 1/2005 | Divita et al. |
| 6,872,528 B2 | 3/2005 | Klatzmann et al. |
| 6,875,578 B2 | 4/2005 | Giuliano et al. |
| 6,881,825 B1 | 4/2005 | Robbins et al. |
| 6,910,434 B2 | 6/2005 | Lundgren et al. |
| 6,995,009 B1 | 2/2006 | Kitamura et al. |
| 7,029,913 B2 | 4/2006 | Thomson |
| 7,030,292 B2 | 4/2006 | Yan et al. |
| 7,070,994 B2 | 7/2006 | Barber et al. |
| 7,250,255 B2 | 7/2007 | Yamanaka |
| 7,439,064 B2 | 10/2008 | Thomson et al. |
| 8,048,999 B2 | 11/2011 | Yamanaka et al. |
| 8,058,065 B2 | 11/2011 | Yamanaka et al. |
| 8,129,187 B2 | 3/2012 | Yamanaka et al. |
| 8,211,697 B2 | 7/2012 | Sakurada et al. |
| 8,278,104 B2 | 10/2012 | Yamanaka et al. |
| 8,298,825 B1 | 10/2012 | Hochedlinger et al. |
| 8,440,461 B2 | 5/2013 | Thomson et al. |
| 2002/0090722 A1 | 7/2002 | Dominko et al. |
| 2002/0123146 A1 | 9/2002 | Klatzmann et al. |
| 2002/0142397 A1 | 10/2002 | Collas et al. |
| 2002/0174013 A1 | 11/2002 | Freeman et al. |
| 2003/0003574 A1 | 1/2003 | Toma et al. |
| 2003/0044976 A1 | 3/2003 | Dominko et al. |
| 2003/0161817 A1 | 8/2003 | Young et al. |
| 2004/0048297 A1 | 3/2004 | Scherf |
| 2004/0137460 A1 | 7/2004 | Yamanaka et al. |
| 2004/0235031 A1 | 11/2004 | Schultz et al. |
| 2005/0019801 A1 | 1/2005 | Rubin et al. |
| 2005/0026133 A1 | 2/2005 | Nakatsuji et al. |
| 2005/0079606 A1 | 4/2005 | Tamaki et al. |
| 2005/0130144 A1 | 6/2005 | Nakatsuji et al. |
| 2005/0162419 A1 | 7/2005 | Kim et al. |
| 2006/0030041 A1 | 2/2006 | Furcht et al. |
| 2006/0084172 A1 | 4/2006 | Muller et al. |
| 2006/0088599 A1 | 4/2006 | Prasad et al. |
| 2006/0095319 A1 | 5/2006 | Cardwell |
| 2006/0110830 A1 | 5/2006 | Dominko et al. |
| 2006/0222636 A1 | 10/2006 | Rambukkana |
| 2006/0246064 A1 | 11/2006 | Boyle |
| 2006/0292620 A1 | 12/2006 | Yamanaka et al. |
| 2007/0033061 A1 | 2/2007 | Patten et al. |
| 2007/0053884 A1 | 3/2007 | Suda et al. |
| 2007/0155013 A1 | 7/2007 | Akaike et al. |
| 2007/0202592 A1 | 8/2007 | Kitagawa et al. |
| 2007/0254884 A1 | 11/2007 | Chen et al. |
| 2007/0269790 A1 | 11/2007 | Amit et al. |
| 2008/0003560 A1 | 1/2008 | Nakatsuji et al. |
| 2008/0076176 A1 | 3/2008 | Dominko et al. |
| 2008/0085555 A1 | 4/2008 | Asahara et al. |
| 2008/0132803 A1 | 6/2008 | Friedlander |
| 2008/0171358 A1 | 7/2008 | Perrault |
| 2008/0171385 A1 | 7/2008 | Bergendahl et al. |
| 2008/0206865 A1 | 8/2008 | Zhang et al. |
| 2008/0233610 A1 | 9/2008 | Thomson et al. |
| 2008/0274914 A1 | 11/2008 | Yamanaka et al. |
| 2008/0280362 A1 | 11/2008 | Jaenisch et al. |
| 2008/0293143 A1 | 11/2008 | Lin et al. |
| 2008/0299548 A1 | 12/2008 | Yamanaka |
| 2009/0047263 A1 | 2/2009 | Yamanaka et al. |
| 2009/0068742 A1 | 3/2009 | Yamanaka |
| 2009/0191159 A1 | 7/2009 | Sakurada et al. |
| 2009/0191171 A1 | 7/2009 | Ma |
| 2009/0227032 A1 | 9/2009 | Yamanaka et al. |
| 2009/0246875 A1 | 10/2009 | Yamanaka et al. |
| 2009/0299763 A1 | 12/2009 | Sakurada |
| 2009/0304646 A1 | 12/2009 | Sakurada et al. |
| 2009/0324559 A1 | 12/2009 | Sakurada |
| 2010/0003757 A1 | 1/2010 | Mack |
| 2010/0021437 A1 | 1/2010 | Isacson |
| 2010/0062533 A1 | 3/2010 | Yamanaka |
| 2010/0062534 A1 | 3/2010 | Hochedlinger |
| 2010/0075421 A1 | 3/2010 | Yamanaka |
| 2010/0093090 A1 | 4/2010 | Deng |
| 2010/0105100 A1 | 4/2010 | Sakurada |
| 2010/0120069 A1 | 5/2010 | Sakurada |
| 2010/0144031 A1 | 6/2010 | Jaenisch |
| 2010/0184051 A1 | 7/2010 | Hochedlinger |
| 2010/0184227 A1 | 7/2010 | Thomson |
| 2010/0210014 A1 | 8/2010 | Yamanaka |
| 2010/0216236 A1 | 8/2010 | Yamanaka |
| 2010/0221827 A1 | 9/2010 | Jaenisch |
| 2010/0233804 A1 | 9/2010 | Zhou |
| 2010/0240090 A1 | 9/2010 | Sakurada |
| 2010/0267135 A1 | 10/2010 | Sakurada |
| 2010/0279404 A1 | 11/2010 | Yamanaka |
| 2011/0014164 A1 | 1/2011 | Huangfu et al. |
| 2011/0039332 A1 | 2/2011 | Sakurada et al. |
| 2013/0059386 A1 | 3/2013 | Yamanaka et al. |
| 2013/0065311 A1 | 3/2013 | Yamanaka et al. |
| 2014/0057355 A1 | 2/2014 | Thomson et al. |
| 2015/0072417 A1 | 3/2015 | Yamanaka et al. |

FOREIGN PATENT DOCUMENTS

| | | |
|---|---|---|
| CN | 101550428 A | 10/2009 |
| EP | 1384775 A1 | 1/2004 |
| EP | 1403366 A1 | 3/2004 |
| EP | 1970446 A1 | 9/2008 |
| EP | 2096169 A1 | 9/2009 |
| EP | 2213727 A1 | 4/2010 |
| JP | 2-227075 | 9/1990 |
| JP | 2002-065261 | 3/2002 |
| JP | 2002-511248 A | 4/2002 |
| JP | 2003-009854 | 1/2003 |
| JP | 2004-161682 A | 6/2004 |
| JP | 2005-095027 | 4/2005 |
| JP | 2005-198546 | 7/2005 |
| JP | 2005-359537 | 12/2005 |
| JP | 2006-526409 | 11/2006 |
| JP | 2008-515435 | 5/2008 |
| JP | 2008-283972 | 11/2008 |
| WO | WO 95/10619 A2 | 4/1995 |
| WO | WO 95/10619 A3 | 7/1995 |
| WO | WO 97/05265 A1 | 2/1997 |
| WO | WO 98/02529 A1 | 1/1998 |
| WO | WO 99/55841 A2 | 11/1999 |
| WO | WO 99/64568 A1 | 12/1999 |
| WO | WO 00/18885 A1 | 4/2000 |
| WO | WO 00/23567 A2 | 4/2000 |
| WO | WO 00/27995 A1 | 5/2000 |
| WO | WO 00/23567 A3 | 7/2000 |
| WO | WO 00/73423 A1 | 12/2000 |
| WO | WO 01/21767 A2 | 3/2001 |
| WO | WO 01/34776 A1 | 5/2001 |
| WO | WO 01/51616 A2 | 7/2001 |
| WO | WO 01/21767 A3 | 8/2001 |
| WO | WO 01/81549 A2 | 11/2001 |
| WO | WO 02/00871 A2 | 1/2002 |

(56) References Cited

FOREIGN PATENT DOCUMENTS

| WO | WO 02/061033 A2 | 8/2002 |
|---|---|---|
| WO | WO 02/000871 A3 | 10/2002 |
| WO | WO 02/086129 A1 | 10/2002 |
| WO | WO 02/086134 A2 | 10/2002 |
| WO | WO 02/097090 A1 | 12/2002 |
| WO | WO 03/018780 A1 | 3/2003 |
| WO | WO 02/086134 A3 | 12/2003 |
| WO | WO 2004/081205 A1 | 9/2004 |
| WO | WO 2005/017149 | 2/2005 |
| WO | WO2005/035741 A1 | 4/2005 |
| WO | WO 2005/080598 A1 | 9/2005 |
| WO | WO 2005/090557 A1 | 9/2005 |
| WO | WO 2006/035741 A1 | 4/2006 |
| WO | WO 2006/083331 | 8/2006 |
| WO | WO 2006/084229 A2 | 8/2006 |
| WO | WO 2006/088867 A2 | 8/2006 |
| WO | WO 2007/014162 | 2/2007 |
| WO | WO 2007/019398 A1 | 2/2007 |
| WO | WO 2007/026255 A2 | 3/2007 |
| WO | WO 2007/054720 A1 | 5/2007 |
| WO | WO 2007/069666 A1 | 6/2007 |
| WO | WO 2007/097494 A2 | 8/2007 |
| WO | WO 2008/030610 A2 | 3/2008 |
| WO | WO 2008/035110 A1 | 3/2008 |
| WO | WO 2008/038148 A2 | 4/2008 |
| WO | WO 2008/089351 A1 | 7/2008 |
| WO | WO 2008/105566 A1 | 9/2008 |
| WO | WO 2008/105630 A1 | 9/2008 |
| WO | WO 2008/116213 A1 | 9/2008 |
| WO | WO 2008/118820 A2 | 10/2008 |
| WO | WO 2008/124133 A1 | 10/2008 |
| WO | WO 2008/118820 A3 | 11/2008 |
| WO | WO 2008/150814 A2 | 12/2008 |
| WO | WO 2008/151058 A2 | 12/2008 |
| WO | WO 2008/151058 A3 | 1/2009 |
| WO | WO 2009/006930 A1 | 1/2009 |
| WO | WO 2009/006997 A1 | 1/2009 |
| WO | WO 2009/007852 A2 | 1/2009 |
| WO | WO 2008/150814 A3 | 2/2009 |
| WO | WO 2009/023161 A1 | 2/2009 |
| WO | WO 2009/032194 A1 | 3/2009 |
| WO | WO 2009/032456 | 3/2009 |
| WO | WO 2009/032456 A3 | 4/2009 |
| WO | WO 2009/057831 A1 | 5/2009 |
| WO | WO 2009/061442 A1 | 5/2009 |
| WO | WO 2009/067563 A1 | 5/2009 |
| WO | WO 2009/007852 A3 | 8/2009 |
| WO | WO 2009/096614 A1 | 8/2009 |
| WO | WO 2009/102983 A2 | 8/2009 |
| WO | WO 2009/115295 A1 | 9/2009 |
| WO | WO 2009/133971 A1 | 11/2009 |
| WO | WO 2009/102983 A3 | 12/2009 |
| WO | WO 2009/144008 A1 | 12/2009 |
| WO | WO 2009/149233 A1 | 12/2009 |
| WO | WO 2010/013359 A1 | 2/2010 |
| WO | WO 2010/048567 A1 | 4/2010 |

OTHER PUBLICATIONS

Allergucci et al. Differences between human embryonic stem cell lines. Hum Reprod Update. Mar.-Apr. 2007;13(2):103-20.
Altschul et al. Gapped BLAST and PSI-BLAST: a new generation of protein database search programs. Nucleic Acids Research. 1997;25(17): 3389-3402.
Amit et al., Clonally Derived Human Embryonic Stem Cell Lines Maintain Pluripotency and Proliferative Potential for Prolonged Periods of Culture, Dev. Biol. 227:271-78, 2000.
Amsellem et al., Ex vivo Expansion of Human Hematopoietic Stem Cells by Direct Delivery of the HOXB4 Homeoprotein, Nat. Med. 9(11):1423-27, 2003.
Anderson et al. Transgenic enrichment of cardiomyocytes from human embryonic stem cells. Mol Ther. Nov. 2007; 15(11):2027-36.
Anisimov et al, "SAGE Identification of Gene Transcripts with Profiled Unique to Pluripotent Mouse R1 Embryonic stem Cells," Genomics, vol. 79, No. 2, Feb. 2002, pp. 69-176.

Aoi et al. Generation of Pluripotent Stem Cells from Adult Mouse Liver and Stomach Cells. Science. Feb. 14, 2008. Published Online Feb. 14, 2008. Science DO1: 10.1126/science.1154884.
Asahi Shimbun Weekly AERA, The Novel Pluripotent Cells Established by Professor Yamanaka of Kyoto University May change Medical Care, pp. 72-73, Dec. 24, 2009, along with a partial English language translation thereof.
Assady et al. Insulin production by human embryonic stem cells. Diabetes. Aug. 2001;50(8): 1691-7.
Assou et al. A meta-analysis of human embryonic stem cells transcriptome integrated into a web-based expression atlas. Stem Cells. Apr. 2007;25(4):961-73.
Avilion et al., Multipotent Cell Lineages in Early Mouse Development Depend on SOX2 Function, Genes Dev. 17:126-40, 2003.
Bader et al. Leukemia inhibitory factor modulates cardiogenesis in embryoid bodies in opposite fashions. Circ Res. Apr. 14, 2000;86(7):787-94.
Bagutti et al. Differentiation of embryonal stem cells into keratinocytes: comparison of wild-type and beta 1 integrin-deficient cells. Dev Biol. Oct. 10, 1996; 179(1): 184-96.
Bang et al., Deconstructing Pluripotency, Science 320:58-59, 2008.
Barrett et al. NCBI GEO: mining tens of millions of expression profiles—database and tools update. Nucleic Acids Res. Jan. 2007;35(Database issue):D760-S.
Barrett et al., Activation Domains of L-Myc and c-Myc Determine Their Transforming Potencies in Rat Embryo Cells, Mol. Cell. Biol. 12(7):3130-37, 1992.
Bayani et al. Multi-color FISH techniques. Curr. Protoc. Cell Biol. 2004; Chapter 22:Unit 22.5.
Becker-Hapak et al. Protein transduction: generation of full-length transducible proteins using the TAT system. Curr Protoc Cell Biol. May 2003;Chapter 20: Unit 20.2.
Belmonte et al. "Induced pluripotent stem cells and reprogramming: seeing the science through the hype." Nat Rev Genet. Dec. 2009;10(12):878-83. Epub Oct. 27, 2009.PMID: 19859062 [PubMed—indexed for MEDLINE]Related citations.
Bendall et al. IGF and FGF cooperatively establish the regulatory stem cell niche of pluripotent human cells in vitro. Nature. Aug. 30, 2007;448(7157): 1015-21.
Benetti et al., A Mammalian microRNA Cluster Controls DNA Methylation and Telomere Recombination via Rbl2-Dependent Regulation of DNA Methyltransferases, Nat. Struct. Mol. Biol. 15(3):268-79, published online Mar. 2, 2008.
Ben-Shushan et al., Rex-1, A Gene Encoding a Transcription Factor Expressed in the Early Embryo, Is Regulated via Oct-3/4 and Oct-6 Binding to an Octomer Site and a Novel Protein, Rox-1, Binding to an Adjacent Site, Mol. Cell Biol. 18(4):1866-78, 1998.
Berg et al. An argument against a role for Oct4 in somatic stem cells. Cell Stem Cell. Oct. 11, 2007;1(4):359-60.
Bibel et al., "Differentiation of mouse embryonic stem cells into a defined neuronal lineage," Nature Neuroscience, 2004, vol. 7, pp. 1003-1009.
Bigdeli et al., Adaptation of Human Embryonic Stem Cells to Feeder-Free and Matrix-Free Culture Conditions Directly on Plastic Surfaces. J. Biotec., 2008, vol. 133, pp. 146-153.
BioPorterTM Gene Therapy System, Inc., Wako Bio Window 40:7, 2002.
BioPorterTM Protein Delivery Reagent From www.biocarta.com.
Birnbaum et al. Slicing across Kingdoms: Regeneration in Plants and Animals. Cell. Feb. 22, 2008; 132(4):697-710.
Birrer et al., L-myc Cooperates With ras to Transform Primary Rat Embryo Fibroblasts, Mol. Cell. Biol. 8(6):2668-73, 1988.
Blackwood et al., Max: A Helix-Loop-Helix Zipper Protein That Forms a Sequence-Specific DNA-Binding Complex With Myc, Science 251(499*):1211-17, 1991.
Blelloch et al. Generation of Induced Pluripotent Stem Cells in the Absence of Drug Selection. Cell Stem Cell. 2007; 1,245-247.
Block et al., Population Expansion, Clonal Growth, and Specific Differentiation Patterns in Primary Cultures of Hepatocytes Induced by HGF/SF, EGF and TGFα in a Chemically Defined (HGM) Medium, J. Cell Biol. 132(6):1133-49, 1996.
Blow, N. Stem cells: in search of common ground. Nature. Feb. 14, 2008;451 (7180):855-8.

(56) References Cited

OTHER PUBLICATIONS

Bonetta, L. European Stem Cell Patents: Taking the moral High Road? Cell. Feb. 22, 2008; 132(4):SI4-S16.
Bongso, A., et al., Isolation and Culture of Inner Cell Mass Cells From Human Blastocysts, Human Reproduction 9(11):2110-2117, 1994.
Boquest et al. Epigenetic programming of mesenchymal stem cells from human adipose tissue. Stem Cell Rev. 2006;2(4):319-29.
Bortvin et al., Incomplete Reactivation of Oct4-Related Genes in Mouse Embryos Cloned From Somatic Nuclei, Development 130:1673-80, 2003.
Boyer et al. Core Transcriptional Regulatory Circuitry in Human Embryonic Stem Cells. Cell. 2005;122(6):947-956.
Brambrink et al. Sequential Expression of Pluripotency Markers during Direct Reprogramming of Mouse Somatic Cells. Cell Stem Cell. 2008; 2, 151-159.
Brena et al. Quantitative assessment of DNA methylation: Potential applications for disease diagnosis, classification, and prognosis in clinical settings. J Mol Med. May 2006;84(5):365-77.
Brough et al., An Essential Domain of the c-Myc Protein Interacts With a Nuclear Factor That Is Also Required for E1A-Mediated Transformation, Mol. Cell. Biol. 15(3):1536-44, 1995.
Brüstle et al. Embryonic stem cell-derived glial precursors: a source of myelinating transplants. Science. Jul. 30, 1999;285(5428):754-6.
Burns et al. Diabetes mellitus: a potential target for stem cell therapy. Curr Stem Cell Res Ther. May 2006; 1 (2):255-66.
Buttery et al. Differentiation of osteoblasts and in vitro bone formation from murine embryonic stem cells. Tissue Eng. Feb. 2001;7(1):89-99.
Cai et al. Directed differentiation of human embryonic stem cells into functional hepatic cells. Hepatology. May 2007;45(5): 1229-39.
Campbell et al. Phosphonate Ester Synthesis Using a Modified Mitsunobu Condensation. J. Org. Chem.1994;59: 658-660.
Carey et al., "Reprogramming of murine and human somatic cells using a single polycistronic vector," Proc. Natl. Acad. Sci. USA, Jan. 6, 2009, vol. 106(1), pp. 157-162, Epub. Dec. 24, 2008. Erratum in: Proc. Natl. Acad. Sci. USA, Mar. 31, 2009, vol. 106(13), p. 5449.
Carpenter et al., "Characterization and Differentiation of Human Embryonic Stem Cells," Cloning and Stem Cells, vol. 5, No. 1, Nov. 1, 2003, pp. 169-176.
Cartwright et al. LIF/STAT3 controls ES cell self-renewal and pluripotency by a Myc-dependent mechanism. Development. Mar. 2005; 132(5):885-96.
Cauffman et al., "Oct-4 mRNA and protein expression during human preimplantation development," Molecular Human Reproduction, vol. 11, No. 3, Feb. 4, 2005, pp. 173-180.
Chadwick et al. Cytokines and BMP-4 promote hematopoietic differentiation of human embryonic stem cells. Blood. Aug. 1, 2003; 102(3):906-15.
Chambers et al., Functional Expression Cloning of Nanog, A Pluripotency Sustaining Factor in Embryonic Stem Cells, Cell 113:643-55, 2003.
Chang et al. The c-Myc transactivation domain is a direct modulator of apoptotic versus proliferative signals. Mol Cell Biol. Jun. 2000;20(12):4309-19.
Chang et al., Embryonic Stem Cells/Induced Pluripotent Stem Cells, Stem Cells, 2009, vol. 27, pp. 1042-1049.
Check, E., Simple Recipe Gives Adult Cells Embryonic Powers, Nature 442:11, Jul. 6, 2006.
Chen et al. Analogous Organic-Synthesis of Small-Compound Libraries—Validation of Combinatorial Chemistry in Small-Molecule Synthesis. Journal of the American Chemical Society. 1994;116(6): 2661-2662.
Chen et al. From stem cells to oligodendrocytes: prospects for brain therapy. Stem Cell Rev. Dec. 2007;3(4):280-8.
Cheng et al., Mammalian Grb2 Regulates Multiple Steps in Embryonic Development and Malignant Transformation, Cell 95:793-803, 1998.
Childs et al. Regression of metastatic renal-cell carcinoma after nonmyeloablative allogeneic peripheral-blood stem-cell transplantation. N Engl J Med. Sep. 14, 2000;343(11):750-8.
Chin et al. Induced pluripotent stem cells and embryonic stem cells are distinguished by gene expression signatures. Cell Stem Cell. Jul. 2, 2009;5(1): 111-23.
Cho et al. An unnatural biopolymer. Science. Sep. 3, 1993;261 (5126): 1303-5.
Cinalli et al. Germ Cells are Forever. Cell. Feb. 22, 2008; 132(4):559-562.
CIRM Public Release. $24 Million in New Stem Cell Research Funding Awarded to 25 California Institutions. California Institute for Regenerative Medicine (4 pages). Jun. 27, 2008.
CIRM: Summaries of Review for Applications to RFA 07-05. California Institute for Regenerative Medicine Web site. 2007. Available at: http://www.cirm.ca.gov/RFAIrfa_07-05/. Accessed Jul. 1, 2008.
Cline et al. Randomize Gene Sequences with New PCR Mutagenesis Kit. Strategies Newsletter. 2000; 13: 157-161.
Cohen et al., "Ooplasmic Transfer in Mature Human Oocytes," Molecular Human Reproduction, 1998, vol. 4, pp. 269-280. Correction printed in Nature 447:897, Jun. 21, 2007.
Cosmo Bio News 49:5, 2005 (catalog of ES cell culture medium).
Coutts et al. Stem cells for the treatment of spinal cord injury. Exp Neurol. Feb. 2008;209(2):368-77.
Cowan et al. Nuclear Reprogramming of Somatic Cells After Fusion with Human Embryonic Stem Cells. Science, 2005, vol. 309, pp. 1369-1374.
Cowan et al., Derivation of Embryonic Stem-Cell Lines From Human Blastocysts, N. Engl. J. Med. 350:1353-56, 2004.
Cowling et al. Mechanism of transcriptional activation by the Myc oncoproteins. Semin Cancer Biol. Aug. 2006; 16(4):242-52.
Crouch, D.H., et al., Multiple Phenotypes Associated With Myc-Induced Transformation of Chick Embryo Fibroblasts Can Be Dissociated by a Basic Region Mutation, Nucleic Acids Research 24(16):3216-3221, 1996.
Cyranoski et al. Simple switch turns cells embryonic. Nature. 2007; 447:618-619.
Cyranoski, D. Stem cells: 5 things to know before jumping on the iPS bandwagon. Nature. 2008;452(7186)406-408.
Cyranoski. Japan ramps up patent effort to keep iPS lead. Nature. 2008; 453(7198):962-3.
Daley et al. Prospects for Stem Cell Based Therapy. Cell. Feb. 22, 2008; 132(4):544-548.
Daley, et al., "Broader implications of defining standards for the pluripotency of iPSCs." Cell Stem Cell. Mar. 6, 2009;4(3):200-1; author reply 202. No abstract available. PMID: 19265657 [PubMed—indexed for MEDLINE]Related citations.
D'Amour et al. Efficient differentiation of human embryonic stem cells to definitive endoderm. Nat Biotechnol. Dec. 2005;23(12):1534-41.
D'Amour et al. Production of pancreatic hormone-expressing endocrine cells from human embryonic stem cells. Nat Biotechnol. Nov. 2006;24(11): 1392-401.
Dang et al., The Biology of the Mammalian Kruppel-Like Family of Transcription Factors, Int. J. Biochem. Cell Biol. 32:1103-21, 2000.
Dani, et al. Differentiation of embryonic stem cells into adipocytes in vitro. J Cell Sci. Jun. 1997;110 (Pt 11):1279-85.
Deb, et al; Embryonic Stem Cells: From Markers to Market. Feb. 2008; 11(1): 19-37.
Denker, H. W. Human embryonic stem cells: the real challenge for research as well as for bioethics is still ahead of us. Cells Tissues Organs. 2008;187(4):250-6.
Dewitt et al. "Diversomers": an approach to nonpeptide, nonoligomeric chemical diversity. Proc Natl Acad Sci USA. Aug. 1, 1993;90(15):6909-13.
Dimos et al. Induced pluripotent stem cells generated from patients with ALS can be differentiated into motor neurons. Science. Aug. 29, 2008;321(5893):1218-21.

(56) References Cited

OTHER PUBLICATIONS

D'Ippolito et al. Marrow-isolated adult multilineage inducible (MIAMI) cells, a unique population of postnatal young and old human cells with extensive expansion and differentiation potential. J Cell Sci. Jun. 15, 2004; 117(Pt 14):2971-81.
Do et al., "Nuclei of Embryonic Stem Cells Reprogram Somatic Cells," Stem Cells, 2004, vol. 22, pp. 941-949.
Durcova-Hills et al. Induced reprogramming of human somatic cells into pluripotency: a new way how to generate pluripotent stem cells. Differentiation. Apr. 2008;76(4):323-5.
Ebert, L. Yamanaka scooped on iPS (stem cell) patent?!. TMCNews reports on Jan. 4, 2009. Available at http://ipbiz.blogspot.com/2009/01/yamanaka-scooped-on-ips-stemcell.html. Accessed May 19, 2009.
Ehrich et al. Quantitative high-throughput analysis of DNA methylation patterns by base-specific cleavage and mass spectrometry. Proc Natl Acad Sci USA. Nov. 1, 2005; 102(44): 15785-90.
Eisen et al. Cluster analysis and display of genome-wide expression patterns. Dec. 8, 1998;95(25): 14863-14868.
Elefanty, A. Ed. In this Issue . . . Stem Cell Research. 2008; 1:87.
Essentials of Stem Cell Biology, R. Lanza et al. Ed., 2006, Elsevier Academic Press, pp. 266-267.
European Examination Report on EP 07 856 194.1, issued Sep. 29, 2011.
European Office Action for Application No. 07856194.1 dated May 9, 2012.
Evans et al. Krüppel-like factor 4 is acetylated by p300 and regulates gene transcription via modulation of histone acetylation. J Biol Chem. Nov. 23, 2007;282(47): 33994-4002.
Evans et al., Establishment in Culture of Pluripotential Cells From Mouse Embryos, Nature 292:154-56, 1981.
Examination Report dated Oct. 15, 2012, issued in connection with European Patent Application No. 10154821.2.
Examination Report dated Oct. 23, 2012, issued in connection with European Patent Application No. 10154819.6.
Examination Report issued in Australian Patent Application No. 2006325975, Apr. 18, 2011.
Examination Report mailed by the New Zealand IP Office on Feb. 9, 2012 in corresponding New Zealand application No. 582018 in 2 pages.
Extended European Search Report issued in connection with European Patent Application No. 10154819.6, Jun. 10, 2010.
Extended European Search Report issued in connection with European Patent Application No. EP 06834636.0, Mar. 11, 2009.
Extended European Search Report issued in connection with European Patent Application No. EP 10154817.0, Jun. 10, 2010.
Extended European Search Report issued in connection with European Patent Application No. EP 10154821.2, Jun. 10, 2010.
Felgner et al. Lipofection: a highly efficient, lipid-mediated DNA-transfection procedure. Proc Natl Acad Sci USA. Nov. 1987;84(21):7413-7.
Feng et al., Reprogramming of Fibroblasts Into Induced Pluripotent Stem Cells With Orphan Nuclear Receptor Esrrb, Nature Cell Biology 11:197-203, 2009.
Ferrer-Costa et al. PMUT: a web-based tool for the annotation of pathological mutations on proteins. Bioinformatics. Jul. 15, 2005;21(14):3176-8.
First Office Action dated Aug. 31, 2012 in corresponding Chinese patent application No. 200880100396.X.
Forsyth et al. Human Embryonic Stem Cell Telomere Length Impacts Directly on Clonal Progenitor Isolation Frequency. Rejuvenation Research. Feb. 2008;11(1):5-17.
Gallop et al. Applications of combinatorial technologies to drug discovery. 1. Background and peptide combinatorial libraries. J Med Chem. Apr. 29, 1994;37(9): 1233-51.
Ghaleb et al. Krüppel-like factors 4 and 5: the yin and yang regulators of cellular proliferation. Cell Res. Feb. 2005; 15(2):92-6.
Goswami et al. Embryonic stem cell therapy. IDrugs. Oct. 2007;10(10):713-9.

Griffiths-Jones et al., miRBase: Tools for microRNA Genomics, Nucleic Acids Research 36:D154-D158, published online Nov. 8, 2007.
Gu et al. Opposite regulation of gene transcription and cell proliferation by c-Myc and Max. Proc Natl Acad Sci USA. Apr. 1, 1993;90(7):2935-9.
Ha et al. Cryopreservation of human embryonic stem cells without the use of a programmable freezer. Hum Reprod. Jul. 2005;20(7): 1779-85.
Hakelien et al. Reprogramming Fibroblasts to Express T-Cell Functions Using Cell Extracts. Nature Biotechnology, May 2002, vol. 20, pp. 460-466.
Hanna et al. Direct Reprogramming of Terminally Differentiated Mature B Lymphocytes to Pluripotency. Cell. Apr. 18, 2008;133: 250-264. Erratum in: Cell. 2008; 134(2):365.
Hanna et al., Direct Reprogramming of Terminally Differentiated Mature B Lymphocytes to Pluripotency, Cell 133:250-264, Apr. 17, 2008.
Hanna et al., Treatment of Sickle Cell Anemia Mouse Model With iPS Cells Generated From Autologous Skin, Science4 318(5858):1920-23, published online Dec. 6, 2007.
Hasegawa et al., Efficient Multicistronic Expression of a Transgene in Human Embryonic Stem Cells, Stem Cells 25:1707-12,. 2007.
Hatfield et al., Stem Cell Division is Regulated by the microRNA Pathway, Nature 435(7044):974-978, 2005.
Heng et al. Incorporating protein transduction domains (PTD) within intracellular proteins associated with the 'stemness' phenotype. Novel use of such recombinant 'fusion' proteins to overcome current limitations of applying autologous adult stem cells in.
Hermann et al. Efficient generation of neural stem cell-like cells from adult human bone marrow stromal cells. J Cell Sci. Sep. 1, 2004; 117(Pt 19):4411-22.
Herold et al., Negative Regulation of the Mammalian UV Response by Myc Through Association with Miz-1, Mol. Cell 10(3):509-21, 2002.
Highfield, R. Dolly creator Proflan Wilmut shuns cloning. Available at http://www.telegraph.co.uk/earth/main.jhtml?xml=/earth/2007/11/16/scidolly116.xml. Accessed Nov. 12, 2008.
Hockemeyer et al. A drug-inducible system for direct reprogramming of human somatic cells to pluripotency. Cell Stem Cell. Sep. 11, 2008;3(3):346-53.
Holt et al., "Regulation of Telomerase Activity in Immortal Cell Lines," Molecular and Cellular Biology, Jun. 1996, pp. 2932-2939.
Hong et al., "Suppression of induced pluripotent stem cell generation by the p53-p21 pathway." Nature. Aug. 27, 2009;460(7259):1132-5. Epub Aug. 9, 2009.PMID: 19668191 [PubMed—indexed for MEDLINE]Free PMC ArticleFree textRelated citations.
Horikawa et al., Differential Cis-Regulation of Human Versus Mouse TERT Gene Expression in vivo: Identification of a Human-Specific Repressive Element, proc. Natl. Acad. Sci. U.S.A. 102(51):18437-42, 2005.
Houbaviy et al., Embryonic Stem Cell-Specific MicroRNAs, Developmental Cell 5(2):351-58, 2003.
Hsiao et al., Marking Embryonic Stem Cells With a 2A Self-Cleaving Peptide: A NKX2-5 Emerald GFP BAC Reporter, PLoS ONE 3(7):e2532, 2008.
http://www.time.com/time/specials/2008/top10/article/0,30583,1855948_1863993,00.html. Accessed Dec. 15, 2008.
Huangfu et al. Efficient Induction of Pluripotent Stem Cells Using Small Molecule Compounds. Companion manuscript to U.S. Appl. No. 61/029,287.
Huangfu et al., Induction of Pluripotent Stem Cells by Defined Factors is Greatly Improved by Small-Molecule Compounds, Nature Biotechnology 26(7):795-97, 2008.
Huangfu et al., Induction of Pluripotent Stem Cells From Primary Human Fibroblasts With Only Oct4 and Sox 2, Nature Biotechnology 26:1269-1275, 2008.
Humphries, C., Reprogrammed Stem Cells Work on Parkinson's: A Study in Rodents Suggests that Skin Cells Can Be Transformed into Neurons to Treat Neurodegeneration, Technology Review, published by MIT, Apr. 8, 2008: http://www.technologyreview.com/printer_friendly_article.aspx?id_20530.

(56) References Cited

OTHER PUBLICATIONS

Hwang et al., Evidence of Pluripotent Human Embryonic Stem Cell Line Derived From a Cloned Blastocyst, Science 303:1669-74, 2004.
Hwang et al., Patient-Specific Embryonic Stem Cells Derived From Human SCNT Blastocysts, Science 308:1777-83, 2005.
Hyun et al. New advances in iPS cell research do not obviate the need for human embryonic stem cells. Cell Stem Cell. Oct. 11, 2007;1(4):367-8.
Ingvarsson, "The myc gene family proteins and their role in transformation and differentiation," Seminars in Cancer Biology, vol. 1, 1990, pp. 359-369.
International Search Report and Written Opinion issued in PCT/JP2011/051685.
International search report dated Jan. 20, 2010 for PCT Application No. US2009/047291.
International search report dated Dec. 15, 2008 for PCT Application No. EP2008/005047.
International search report dated 5/2012008 for PCT Application No. EP2007/010019.
International search report dated Jul. 10, 2009 for PCT Application No. IB2008/002540.
International Search Report issued with respect to PCT/JP2009/058873, mailed Jul. 7, 2009.
Itskovitz-Eldor et al., Differentiation of Human Embryonic Stem Cells Into Embryoid Bodies Comprising the Three Embryonic Germ Layers, Mol. Med. 6(2):88-95, 2000.
Itsykson et al. Derivation of neural precursors from human embryonic stem cells in the presence of noggin. Mol Cell Neurosci. Sep. 2005;30(1):24-36.
Jaenisch et al. Stem Cells, the Molecular Circuitry of Pluripotency and Nuclear Reprogramming. Cell. Feb. 22, 2008; 132(4):567-582.
Jahagirdar et al. Multipotent adult progenitor cell and stem cell plasticity. Stem Cell Rev. 2005;1(1):53-9.
Janssens et al. Autologous bone marrow-derived stem-cell transfer in patients with ST-segment elevation myocardial infarction: double-blind, randomised controlled trial. Lancet. Jan. 14, 2006;367(9505):113-21.
Jiang et al. A core Klf circuitry regulates self-renewal of embryonic stem cells. Nat Cell Biol. Mar. 2008; 10(3):353-60.
Jiang et al. In vitro derivation of functional insulin-producing cells from human embryonic stem cells. Cell Res. Apr. 2007; 17(4):333-44.
Jiang et al. Pluripotency of mesenchymal stem cells derived from adult marrow. Nature. Jul. 4, 2002;418(6893):41-9.
Jikken Igaku (Experimental Medicine) 24:814-19, 2006, along with an English language translation thereof.
Johnston et al. Minimum requirements for efficient transduction of dividing and nondividing cells by feline immunodeficiency virus vectors. J Virol. Jun. 1999;73(6):4991-5000.
Kaji et al., Virus-Free Induction of Pluripotency and Subsequent Excision of Reprogramming Factors, Nature, Mar. 1, 2009, vol. 458, Issue 7239, pp. 771-775.
Kamachi, et at. Mechanism of regulatory target selection by the SOX high-mobility-group domain proteins as revealed by comparison of SOX1/2/3 and SOX9. Mol Cell Biol. Jan. 1999;19(1):107-20.
Kanegae et al. Efficient gene activation in mammalian cells by using recombinant adenovirus expressing site-specific Cre recombinase. Nucleic Acids Res. Oct. 11, 1995;23(19):3816-21.
Kanellopoulou et al., Dicer-Deficient Mouse Embryonic Stem Cells Are Defective in Differentiation and Centromeric Silencing, Genes & Development 19:489-501, 2005.
Kawasaki et al. Induction of midbrain dopaminergic neurons from ES cells by stromal cell-derived inducing activity. Neuron. Oct. 2000;28(1):31-40.
Kehat et al. Human embryonic stem cells can differentiate into myocytes with structural and functional properties of cardiomyocytes. J Clin Invest. Aug. 2001; 108(3):407-14.
Kim et al. Ex vivo characteristics of human amniotic membrane-derived stem cells. Cloning Stem Cells. 2007 Winter;9(4):581-94.
Kim et al., Generation of Human Induced Pluripotent Stem Cells by Direct Delivery of Reprogramming Proteins, Cell Stem Cell 4:472-476, 2009.
Kim et al., Oct4-Induced Pluripotency in Adult Neural Stem Cells, Cell 136:411-419, 2009.
Kim et al., Pluripotent Stem Cells Induced From Adult Neural Stem Cells by Reprogramming with Two Factors, Nature 454:656-650, 2008.
Kitamura et al. Retrovirus-mediated gene transfer and expression cloning: powerful tools in functional genomics. Exp Hematol. Nov. 2003;31(11):1007-14.
Kitamura, T. New experimental approaches in retrovirus-mediated expression screening. Int J Hematol. Jun. 1998;67(4):351-9.
Klingemann, H. Discarded stem cells with a future? Expert Opin Biol Ther. Dec. 2006;6(12): 1251-4.
Knoblich, J.A. Mechanisms of Asymmetric Stem Cell Division. Cell. Feb. 22, 2008; 132(4):583-597.
Koch et al. Transduction of human embryonic stem cells by ecotropic retroviral vectors. Nucl Acids Res. 2006; 34, e120.
Kohge et al. Promotion of antigen-specific antibody production in murine B cells by a moderate increase in histone acetylation. Biochem Pharmacol. Nov. 15, 1998;56(10): 1359-64.
Kohlhase et al., Cloning and Expression Analysis of Sall4, The Murine Homologue of the Gene Mutated in Okihiro Syndrome, Cytogenet. Genome Res. 98:274-77, 2002.
Kopsidas et al. RNA mutagenesis yields highly diverse mRNA libraries for in vitro protein evolution. BMC Biotechnol. Apr. 11, 2007;7:18.
Koyanagi et al., Screening and Functional Analysis of microRNAs which involve in Reprogramming, of Murine Somatic Cells, The Journal of Biochemistry, vol. 79, No. 11, Abstract 1T-7-7 From the 80th Annual Meeting of the Japanese Biochemical Society, Nov. 25, 2007, along with an English language translation thereof.
Kramer et al. Embryonic stem cell-derived chondrogenic differentiation in vitro: activation by BMP-2 and BMP-4. Mech Dev. Apr. 2000;92(2):193-205.
Krausz, E. High-content siRNA screening. Mol Biosyst. Apr. 2007;3(4):232-40.
Krosl et al., In vitro Expansion of Hematopoietic Stem Cells by Recombinant TAT-HOXB4 Protein, Nat. Med 9(11):1428-32, 2003.
Kubicek et al., Reversal of H3K9me2 by a Small-Molecule Inhibitor for the G9a Histone Methyltransferase, Molecular Cell 25:473-81, 2007.
Kunath et al. FGF stimulation of the Erk1/2 signalling cascade triggers transition of pluripotent embryonic stem cells from self-renewal to lineage commitment. Development. Aug. 2007;134(16):2895-902.
Kuroda et al. Octamer and Sox Elements Are Required for Transcriptional cis Regulation of Nanog Gene Expression. Mol Cell Biol. Mar. 2005; 25(6):2475-2485.
Kyoto Shimbun (Japanese Newspaper) article of Apr. 16, 2008, cols. 1-3, along with a partial English language translation thereof.
Laflamme et al, Cardiomyocytes Derived From Human Embryonic Stem Cells in Pro-Survival Factors Enhance Function of Infarcted Rat Hearts, Nat. Biotechnol. 25(9):1015-24, 2007.
Laird et al. Stem Cell Trafficking in Tissue Development, Growth, and Disease. Cell. Feb. 22, 2008; 132(4):612-630.
Lanza et al. (Eds.) Essentials of Stem Cell Biology. Elsevier Academic Press. 2006. (Table of Contents only).
Lebkowski et al., "Human embryonic Stem Cells: Culture, Differentiation, and Genetic Modification for Regenerative Medicine Applications," The Cancer Journal, vol. 7(S.2), 2001, pp. S83-S94.
Lee et al. Efficient generation of midbrain and hindbrain neurons from mouse embryonic stem cells. Nat Biotechnol. Jun. 2000;18(6):675-9.
Lemken et al. Evidence for intercellular trafficking of VP22 in living cells. Mol Ther. Feb. 2007;15(2):310-9.
Lengner et al. The pluripotency regulator Oct4: a role in somatic stem cells? Cell Cycle. Mar. 2008;7(6):725-8.
Lewitzky et al., "Reprogramming somatic cells towards pluripotency by defined factors." Curr Opin Biotechnol. Oct. 2007;18(5):467-73. Review.PMID: 18024106 [PubMed—indexed for MEDLINE]Related citations.

(56) References Cited

OTHER PUBLICATIONS

Li et al. Small dsRNAs induce transcriptional activation in human cells. Proc Natl Acad Sci. 2006; 103, 17337-17342.
Li et al., "Murine embryonic stem cell differentiation is promoted by SOCS-3 and inhibited by the zinc finger transcription factor Klf4," Blood, vol. 105, No. 2, Jan. 15, 2005, pp. 635-637.
Li et al., Leukaemia Disease Genes: Large-Scale Cloning and Pathway Predictions, Nat. Genet. 23(3):348-353, 1999.
Li, H., et al., Pluripotent Stem Cells From the Adult Mouse Inner Ear, Nature Medicine 9(10):1293-1299, Oct. 2003.
Liao et al., Enhanced Efficiency of Generating Induced Pluripotent Stem (iPS) Cells From Human Somatic Cells by a Combination of Six Transcription Factors, Cell Research 18:600-603, doi: 10.1038/cr.2008.51, published online Apr. 15, 2008.
Lieschke et al. Development of functional macrophages from embryonal stem cells in vitro. Exp Hematol. Apr. 1995;23(4):328-34.
Lin et al., Mir-302 Reprograms Human Skin Cancer Cells into a Pluripotent ES-Cell-Like State, RNA 14:1-10, 2008.
Lin-Goerke et al. PCR-based random mutagenesis using manganese and reduced dNTP concentration. Biotechniques. Sep. 1997;23(3):409-12.
Link et al. Therapeutic protein transduction of mammalian cells and mice by nucleic acid-free lentiviral nanoparticles. Nucleic Acids Res. Jan. 30, 2006;34(2):e16.
Littlewood et al. A modified oestrogen receptor ligand-binding domain as an improved switch for the regulation of heterologous proteins. Nucleic Acids Res. May 25, 1995;23(10):1686-90.
Liu, S. iPS Cells: a More Critical Review. Stem Cells Dev. Jun. 2008;17(3):391-7.
Loh et al. The Oct4 and Nanog transcription network regulates pluripotency in mouse embryonic stem cells. Nat Genet. Apr. 2006;38(4):431-40.
Loriot et al., Five New Human Cancer-Germline Genes Identified Among 12 Genes Expressed in Spermatogonia, Int. J. Cancer 105:371-76, 2003.
Loudig et al. Transcriptional co-operativity between distant retinoic acid response elements in regulation of Cyp26A1 inducibility. Biochem J. Nov. 15, 2005;392(Pt 1):241-8.
Lowry et al. Generation of human induced pluripotent stem cells from dermal fibroblasts. Proc Natl Acad Sci USA. Feb. 26, 2008; 105(8):2883-8.
Ludwig et al. Derivation of human embryonic stem cells in defined conditions. Nat Biotechnol. Feb. 2006;24(2):185-7.
Lumelsky et al. Differentiation of embryonic stem cells to insulin-secreting structures similar to pancreatic islets. Science. May 18, 2001;292(5520):1389-94.
Lunde et al. Zebrafish pou5f1/pou2, homolog of mammalian Oct4, functions in the endoderm specification cascade. Curr Biol. Jan. 6, 2004;14(1):48-55.
Lungwitz et al. Polyethylenimine-based non-viral gene delivery systems. Eur J Pharm Biopharm. Jul. 2005;60(2):247-66.
Maherali et al. A high-efficiency system for the generation and study of human induced pluripotent stem cells. Cell Stem Cell. Sep. 11, 2008;3(3):340-5.
Maherali et al. Directly reprogrammed fibroblasts show global epigenetic remodeling and widespread tissue contribution. Cell Stem Cell. Jun. 7, 2007;1(1):55-70.
Mali et al. Improved efficiency and pace of generating induced pluripotent stem cells from human adult and fetal fibroblasts. Stem Cells. Aug. 2008;26(8):1998-2005.
Marchetto et al. Transcriptional signature and memory retention of human-induced pluripotent stem cells. PLoS One. Sep. 18, 2009;4(9):e7076.
Marson et al., Wnt Signaling Promotes Reprogramming of Somatic Cells to Pluripotency, Cell Stem Cell 3:132-35, 2008.
Martin, Isolation of a Pluripotent Cell Line From Early Mouse Embryos Cultured in Medium Conditioned by Teratocarcinoma Stem Cells, Proc. Natl. Acad. Sci. U.S.A. 78(12):7634-38, 1981.
Maruyama et al., Differential Roles for Sox15 and Sox2 in Transcriptional Control in Mouse Embryonic Stem Cells, J. Biol., Chem. 280(26):24371-79, 2005.
Maruyama, "Functional Analysis of Sox15 and Sox2," Ph.D. Thesis, Nara Institute of Science and Technology, Jan. 31, 2005, in 121 pages.
Masaki et al. Heterogeneity of pluripotent marker gene expression in colonies generated in human iPS cell induction culture. Stem Cell Research. 2008; 1:105-115.
Masaki et al. Tendency of Pluripotential marker gene expression in colonies derived from human neonatal fibroblasts induced by the human iPS cell method. Stem Cell Researchr. 2008. doi: 10.1016/j.scr.2008.01.001 (Accepted Manuscript).
Mathe et al. Computational approaches for predicting the biological effect of p53 missense mutations: a comparison of three sequence analysis based methods. Nucleic Acids Res. Mar. 6, 2006;34(5):1317-25.
Matsuda et al. STAT3 activation is sufficient to maintain an undifferentiated state of mouse embryonic stem cells. EMBO J. Aug. 2, 1999;18(15):4261-9.
McMahon et al., The Wnt-1 (int-1) Proto-Oncogene Is Required for Development of a Large Region of the Mouse Brain, Cell 62:1073-85, 1990.
Meiner et al, Disruption of the Acyl-CoA: Cholesterol Acyltransferase Gene in Mice: Evidence Suggesting Multiple Cholesterol Esterification Enzymes in Mammals, Proc. Natl. Acad. Sci. U.S.A. 93:14041-46, 1996.
Meissner et al. Direct reprogramming of genetically unmodified fibroblasts into pluripotent stem cells. Nat Biotech. 2007; 25, 1177-1181.
microRNA Jikken Purotokoru (microRNA Experimental Protocol), pp. 20-35, 2008, Yodosha Co., Ltd.
Mikkelsen et al. Dissecting direct reprogramming through integrative genomic analysis. Nature. Jul. 3, 2008;454(7200):49-55. Erratum in: Nature. 2008;454(7205):794.
Mimeault et al. Concise Review: Recent Advances on the Significance of Stem Cells in Tissue Regeneration and Cancer Therapies. Stem Cells, 2006, vol. 24, pp. 2319-2345.
Mitsui et al., The Homeoprotein Nanog Is Required for Maintenance of Pluripotency in Mouse Epiblast and ES Cells, Cell 113:631-42, 2003.
Miura et al. "Variation in the safety of induced pluripotent stem cell lines." Nat Biotechnol. Aug. 2009;27(8):743-5. Epub Jul. 9, 2009. PMID: 19590502 [PubMed—indexed for MEDLINE]Related citations.
Miyagishi et al. Strategies for generation of an siRNA expression library directed against the human genome. Oligonucleotides. 2003;13(5):325-33.
Miyoshi et al. Development of a self-inactivating lentivirus vector. J Virol. Oct. 1998;72(10):1389-1.
More California Dough—$23 Million—Rolls Out the Door for Stem Cell Research. California Stem Cell Report Web Site. 2005. Available at: http://californiastemcellreport.blogspot.com/2008/06/more-dough-25-million-rolls-out-door-in.html. Accessed Jul. 1.
Morgenstern et al. Advanced mammalian gene transfer: high titre retroviral vectors with multiple drug selection markers and a complementary helper-free packaging cell line. Nucleic Acids Res. Jun. 25, 1990; 18(12):3587-3596.
Morita et al. Plat-E: An Efficient and Stable System for Transient Packaging of Retroviruses, Gene Ther. 7:1063-66, 2000.
Morizane et al. From bench to bed: the potential of stem cells for the treatment of Parkinson's disease. Cell Tissue Res. Jan. 2008;331(1):323-36.
Morling et al. Enhanced transduction efficiency of retroviral vectors coprecipitated with calcium phosphate. Gene Ther. Sep. 1995;2(7):504-8.
Morrison, S.J. Stem Cells and Niches: Mechanisms that Promote Stem Cell Maintenance throughout Life. Cell. Feb. 22, 2008; 132(4):598-611.
Mummery et al. Differentiation of human embryonic stem cells to cardiomyocytes: role of coculture with visceral endoderm-like cells. Circulation. Jun. 3, 2003; 107(21):2733-40.

(56) References Cited

OTHER PUBLICATIONS

Murry et al. Differentiation of Embryonic Stem Cells to Clinically Relevant Populations: Lessons from Embryonic Development. Cell. Feb. 22, 2008; 132(4):661-680.
Nagano et al., "Large-Scale Identification of Proteins Expressed in Mouse Embryonic Stem Cells," Proteomics 5:1346-1361, 2005.
Nagy et al. Embryonic stem cells alone are able to support fetal development in the mouse. Development. Nov. 1990;110(3):815-21.
Nakagawa et al., "Promotion of direct reprogramming by transformation-deficient Myc." Proc Natl Acad Sci U S A. Aug. 10, 2010;107(32):14152-7. Epub Jul. 26, 2010.PMID: 20660764 [PubMed—indexed for MEDLINE]Related citations.
Nakagawa et al., Generation of Induced Pluripotent Stem Cells Without Myc From Mouse and Human Fibroblasts, Nat. Biotechnol. 26(1):101-06, published online Nov. 30, 2007.
Nakatake et al. Klf4 cooperates with Oct3/4 and Sox2 to activate the Lefty1 core promoter in embryonic stem cells. Mol Cell Biol. Oct. 2006;26(20):7772-82.
Naldini et al. In vivo gene delivery and stable transduction of nondividing cells by a lentiviral vector. Science. Apr. 12, 1996;272(5259):263-7.
Needleman et al. A general method applicable to the search for similarities in the amino acid sequence of two proteins. J Mol Biol. Mar. 1970;48(3):443-53.
Négre et al. Lentiviral vectors derived from simian immunodeficiency virus. Curr Top Microbiol Immunol. 2002;261:53-74.
Newton, Attracting World's Attention. Pluripotent Cells Are Generated From Human Skin. What is the 'iPS Cell' That Can Be Used Not Only in the Regeneration Therapy but Also in the Tailor-Made Therapy, pp. 70-75, Feb. 2008, along with a partial English language translation thereof.
Ng et al. Predicting the effects of amino acid substitutions on protein function. Annu Rev Genomics Hum Genet. 2006;7:61-80.
Nichols et al., Formation of Pluripotent Stem Cells in the Mammalian Embryo Depends on the POU Transcription Factor Oct4, Cell 95:379-91, 1998.
Nienhuis et al., Genotoxicity of Retroviral Integration in Hematopoietic Cells, Mol. Ther. 13(6):1031-49, 2006.
Niwa et al. Self-renewal of pluripotent embryonic stem cells is mediated via activation of STAT3. Genes Dev. Jul. 1, 1998;12(13):2048-60.
Niwa et al., Efficient Selection for High-Expression Transfectants With a Novel Eukaryotic Vector, Gene 108(2):193-99,1991.
Nolta et al., Transduction of Pluripotent Human Hematopoietic Stem Cells Demonstrated by Clonal Analysis After Engraftment in Immune-Deficient Mice, Proc. Natl. Acad. Sci. USA 93(6):2414-19, 1996.
Notice of Opposition to a European patent dated May 3, 2012 in corresponding European patent application No. 06834636.0 in 32 pages.
Obinata, "Conditionally immortalized cell lines with differentiated functions established from temperature-sensative T-antigen transgenic mice," Genes to Cells, vol. 2, 1997, pp. 235-244.
Office Action issued in connection with Chinese Patent Application No. 200680048227.7, Sep. 9, 2010.
Office Action issued in connection with European Patent Application No. EP 10154819.6, Nov. 8, 2013.
Office Action issued in connection with European Patent Application No. EP 06834636.0, Apr. 30, 2010.
Office Action issued in connection with European Patent Application No. EP 06834636.0, Oct. 25, 2010.
Office Action issued in connection with Israeli Patent Application No. 191903, Aug. 19, 2010.
Office Action issued in connection with Japanese Patent Application No. JP 2009-056747, mailed Jun. 2, 2009.
Office Action issued in connection with Japanese Patent Application No. JP 2009-056748, mailed Jun. 2, 2009.
Office Action issued in connection with Japanese Patent Application No. JP 2009-056749, mailed Jun. 4, 2009.
Office Action issued in connection with Japanese Patent Application No. JP 2009-056750, mailed Jun. 2, 2009.
Office Action issued in connection with New Zealand Patent Application No. 569530, Apr. 20, 2010.
Office Action issued in connection with Singapore Patent Application No. 200804231-9, Apr. 13, 2010.
Office Action issued in connection with Singapore Patent Application No. 200901803-7, Jan. 22, 2010.
Office Action issued in GB0922013.8.
Official Action issued in connection with Eurasian Patent Application No. 200870046, Nov. 9, 2009.
Official Action issued in connection with Eurasian Patent Application No. 201000858, Jul. 14, 2010.
Official Action issued in connection with Japanese Patent Application No. JP 2009-056748, mailed Nov. 4, 2009.
Official Rejection issued in connection with Japanese Patent Application No. JP 2009-056748, mailed Feb. 23, 2010.
Official Rejection issued in connection with Japanese Patent Application No. JP 2009-056749, mailed Nov. 4, 2009.
Ohnuki et al., "Generation and characterization of human induced pluripotent stem cells." Curr Protoc Stem Cell Biol. Jun. 2009;Chapter 4:Unit 4A.2.PMID: 19536759 [PubMed—indexed for MEDLINE]Related citations.
Okabe et al., Green Mice as a Source of Ubiquitous Green Cells, FEBS Letters, 1997, vol. 407, pp. 313-319.
Okamoto et al., A Novel Octamer Binding Transportation Factor is Differentially Expressed in Mouse Embryonic Cells, Cell 60:461-72, 1990.
Okita et al. Generation of germline-competent induced pluripotent stem cells. Nature Jul. 19, 2007;448(7151)313-17.
Okita et al. Intracellular Signaling Pathways Regulating Pluripotency of Embryonic Stem Cells. Current Stem Cell Research & Therapy. 2006;1:103-111.
Okita et al., "Generation of mouse-induced pluripotent stem cells with plasmid vectors." Nat Protoc. 2010;5(3):418-28. Epub Feb. 11, 2010.PMID: 20203661 [PubMed—indexed for MEDLINE]Related citations.
Okita et al., "Induction of pluripotency by defined factors." Exp Cell Res. Oct. 1, 2010;316(16):2565-70. Epub Apr. 24, 2010. Review. PMID: 20420827 [PubMed—indexed for MEDLINE]Related citations.
Okita et al., Generation of Mouse Induced Pluripotent Stem Cells Without Viral Vectors, Science 322(5903):949-53, published online Oct. 9, 2008.
Okuda et al., UTF1, A Novel Transcriptional Coactivator Expressed in Pluripotent Embryonic Stem Cells and Extra-Embryonic Cells, EMBO J. 17(7):2019-32, 1998.
Okumura-Nakanishi et al., "Oct-3/4 and Sox2 Regulate Oct-3/4 Gene in Embryonic Stem Cells," The Journal of Biological Chemistry 280(7):5307-5317, Feb. 18, 2006.
Onishi et al. Applications of retrovirus-mediated expression cloning. Exp Hematol. Feb. 1996;24(2):324-9.
Orkin et al. Hematopoiesis: An Evolving Paradigm for Stem Cell Biology. Cell. Feb. 22, 2008;132(4):631-644.
Oshima et al., "Mechanosensitive Hair Cell-like Cells from Embryonic and Induced Pluripotent Stem Cells," Cell, vol. 141, pp. 704-716 (May 14, 2010).
Osuna et al. Protein evolution by codon-based random deletions. Nucleic Acids Res. Sep. 30, 2004;32(17):e136.
Padmanabhan et al. Visualization of telomerase reverse transcriptase (hTERT) promoter activity using a trimodality fusion reporter construct. J Nucl Med. Feb. 2006;47(2):270-7.
Park et al. Disease-specific induced pluripotent stem cells. Cell. Sep. 5, 2008; 134(5):877-86.
Park et al. Reprogramming of human somatic cells to pluripotency with defined factors. Nature. 2008;451(7175):141-146.
Park, A. Stem-cell research: The quest resumes. Time Magazine. Feb. 9, 2009. Available at http://www.time.com/time/health/article/0,8599,1874717,00.html. Accessed Jun. 3, 2009.
Parson, A.B. Stem Cell Biotech: Seeking a Piece of the Action. Cell. Feb. 22, 2008; 132(4):511-513.
Pearson et al. Improved tools for biological sequence comparison. Proc Natl Acad Sci USA. Apr. 1988;85(8):2444-8.

(56) References Cited

OTHER PUBLICATIONS

Pearson, W.R. Rapid and sensitive sequence comparison with FASTP and FASTA. Methods Enzymol. 1990;183:63-98.
Peister et al., Gene Ther, Jan. 2004, vol. 11, Issue 2, pp. 224-228.
Pera, M.F. On the Road to Reprogramming. Stem Cell Research. 2008; 1:103-104.
Pomp et al. Generation of peripheral sensory and sympathetic neurons and neural crest cells from human embryonic stem cells. Stem Cells. Aug. 2005;23(7):923-30.
Postic et al., Dual Roles for Glucokinase in Glucose Homeostasis as Determined by Liver and Pancreatic β Cell-Specific Gene Knockouts Using Cre Recombinase, J. Biol. Chem 274(1):305-15.
Pralong et al. Cell fusion for reprogramming pluripotency: toward elimination of the pluripotent genome. Stem Cell Rev. 2006;2(4):331-40.
Prelle et al. Overexpression of insulin-like growth factor-II in mouse embryonic stem cells promotes myogenic differentiation. Biochem Biophys Res Commun. Nov. 2, 2000;277(3):631-8.
Qin et al., Direct Generation of ES-Like Cells From Unmodified Mouse Embryonic Fibroblasts by Oct4/Sox2/Myc/Klf4, Cell Res. 17(11):959-62, 2007.
Quenneville et al., Mol. Ther., Oct. 2004, vol. 10, Issue 4, pp. 679-687.
Rambhatla et al. Generation of hepatocyte-like cells from human embryonic stem cells. Cell Transplant. 2003;12(1):1-11.
Rao, M. Conserved and divergent paths that regulate self-renewal in mouse and human embryonic stem cells. Dev Biol. Nov. 15, 2004;275(2):269-86.
Ratajczak et al. Bone-marrow-derived stem cells—our key to longevity? J. Appl. Genet. 2007;48(4):307-319.
Reubinoff et al. Neural progenitors from human embryonic stem cells. Nat Biotechnol. Dec. 2001;19(12):1134-40.
Riviére et al. Effects of retroviral vector design on expression of human adenosine deaminase in murine bone marrow transplant recipients engrafted with genetically modified cells. Proc Natl Acad Sci USA. Jul. 18, 1995;92(15):6733-7.
Rodda et al. Transcriptional regulation of nanog by OCT4 and SOX2. J Biol Chem. Jul. 1, 2005;280(26):24731-7.
Rodriguez et al. Manipulation of OCT4 levels in human embryonic stem cells results in induction of differential cell types. Exp Biol Med (Maywood). Nov. 2007;232(10):1368-80.
Root et al. Genome-scale loss-of-function screening with a lentiviral RNAi library. Nat Methods. Sep. 2006;3(9):715-9.
Rosenfeld et al. Adenovirus-mediated transfer of a recombinant alpha 1-antitrypsin gene to the lung epithelium in vivo. Science. Apr. 19, 1991;252(5004):431-4.
Rossant, J. Stem Cell and Early Lineage Development. Cell. Feb. 22, 2008; 132(4):527-531.
Rossant, J. Stem Cells: The Magic Brew. Nature. Jul. 19, 2007;448, 260-262.
Rossi et al. Stem Cells and the Pathways to Aging and Cancer. Cell. Feb. 22, 2008; 132(4):681-696.
Rubin, L. Stem Cell and Drug Discovery: The Beginning of a New Era? Cell. Feb. 22, 2008;132(4):549-552.
Ryan et al., POU Domain Family Values: Flexibility, Partnerships, and Developmental Codes, Genes Dev. 11:1207-25, 1997.
Rybouchkin, A., et al., Role of Histone Acetylation in Reprogramming of Somatic Nuclei Following Nuclear Transfer, Biology of Reproduction 74:1083-1089, 2006.
Sadowski et al. GAL4-VP16 is an unusually potent transcriptional activator. Nature. Oct. 6, 1988;335(6190):563-;4.
Sakai et al., A Transgenic Mouse Line That Retains Cre Recombinase Activity in Mature Oocytes Irrespective of the cre Transgene Transmission, Biochem. Biophys. Res. Commun. 237(2):318-24, 1997.
Saldanha et al. Assessment of telomere length and factors that contribute to its stability. Eur J Biochem. Feb. 2003;270(3):389-403.
Salmon et al., Reversible Immortalization of Human Primary Cells by Lentivector-Mediated Transfer of Specific Genes, Mol. Ther. 2(4):404-14, 2000.
Sarid, J., et al., Evolutionarily Conserved Regions of the Human c-Myc Protein Can Be Uncoupled From Transforming Activity, Proc. Natl. Acad. Sci. USA 84(1):170-173, 1987.
Sato et al., Maintenance of Pluripotency in Human and Mouse Embryonic Stem Cells Through Activation of Wnt Signaling by a Pharmacological GSK-3-Specific Inhibitor, Nat. Med. 10(1):55-63, 2004.
Schepers et al., Twenty Pairs of Sox: Extent, Homology, and Nomenclature of the Mouse and Human Sox Transcription Factor Gene Families, Dev. Cell 3:167-70, 2002.
Scherr et al. Gene silencing by small regulatory RNAs in mammalian cells. Cell Cycle. Feb. 1, 2007;6(4):444-9.
Schuldiner et al. Induced neuronal differentiation of human embryonic stem cells. Brain Res. Sep. 21, 2001;913(2):201-5.
Schwenk et al. Hybrid embryonic stem cell-derived tetraploid mice show apparently normal morphological, physiological, and neurological characteristics. Mol Cell Biol. Jun. 2003;23(11):3982-9.
Science magazine names top 10 breakthroughs of 2008. Available at http://arstechnica.com/old/content/2008/12/isciencei-names-top-10-scientific-breakthroughs-of-2008.ars. Accessed May 19, 2009.
Shah, R. Pharmacogenetics in drug regulation: promise, potential and pitfalls. Philos Trans R Soc Lond B Biol Sci. Aug. 29, 2005; 360(1460):1617-1638.
Shao et al., Generation of iPS Cells Using Defined Factors Linked via the Self-Cleaving 2A Sequences in a Single Open Reading Frame, Cell Res., Mar. 2009, vol. 19, Issue 3, pp. 296-312.
Shi et al., A Combined Chemical and Genetic Approach for the Generation of Induced Pluripotent Stem Cells, Cell Stem Cell 2:525-28, 2008.
Shi et al., Induction of Pluripotent Stem Cells From Mouse Embryonic Fibroblasts by Oct4 and Klf4 With Small-Molecule Compounds, Cell Stem Cell 3:568-74, 2008.
Silva et al. Capturing Pluripotericy. Cell. Feb. 22, 2008; 132(4):532-536.
Silva et al. Profiling essential genes in human mammary cells by multiplex RNAi screening. Science. Feb. 1, 2008;319(5863):617-20.
Silva et al., Promotion of Reprogramming to ground State Pluripotency by Signal Inhibition, PLoS Biology 6910):2237-47, 2008.
Sinkkonen et al., MicroRNAs Control de novo DNA Methylation Through Regulation of Transcriptional Repressors in Mouse Embryonic Stem Cells, Nat. Struct. Mol. Biol. 15(3):259-267, published online Mar. 2, 2008.
Skottman et al. Culture conditions for human embryonic stem cells. Reproduction. Nov. 2006;132(5):691-8.
Soldner et al., Parkinson's Disease Patient-Derived Induced Pluripotent Stem Cells Free of Viral Reprogramming Factors, Cell, Mar. 6, 2009, vol. 136, Issue 5, pp. 964-977.
Sottile et al. In vitro osteogenic differentiation of human ES cells. Cloning Stem Cells. 2003;5(2):149-55.
Spencer et al., E-Cadherin Inhibits Cell Surface Localization of the Pro-Migratory 5T4 Oncofetal Antigen in Mouse Embryonic Stem Cells, Mol. Biol. Cell 18:2838-51, 2007.
Spivakov et al., Epigenetic Signatures of Stem-Cell Identify, Nat. Rev. Genet. 8(4):263-271, 2007.
Stadler et al. Small RNAs: Keeping Stem Cells in Line. Cell. Feb. 22, 2008; 132(4):563-566.
Stadtfeld et al., "Induced pluripotency: history, mechanisms, and applications," Genes & Development, vol. 24, 2010, pp. 2239-2263.
Stadtfeld et al., Induced Pluripotent Stem Cells Generated Without Viral Integration, Science 322(5903):945-49, published online Sep. 25, 2008.
Stadtfeld, M. Defining molecular cornerstones during fibroblast to iPS cell reprogramming in mouse. Cell Stem Cell. Mar. 6, 2008;2(3):230-40.
Stem Cells Made to Mimic Disease, BBC News, http://newsvote.bbc.co.uk/mpapps/pagetools/print/news.bbc.co.uk/2/hi/health/7334365.stm, Apr. 7, 2008.

(56) References Cited

OTHER PUBLICATIONS

Stewart et al. Mechanisms of self-renewal in human embryonic stem cells. Eur J Cancer. Jun. 2006;42(9):1257-72.
Stojkovic et al. Derivation, growth and applications of human embryonic stem cells. Reproduction. Sep. 2004;128(3):259-67.
Strelchenko et al. Embryonic stem cells from morula. Methods Enzymol. 2006;418:93-108.
Suh et al., Human Embryonic Stem Cells Express a Unique Set of microRNAs, Developmental Biology 270:488-498, 2004.
Sumi et al. Apoptosis and differentiation of human embryonic stem cells induced by sustained activation of c-Myc. Oncogene. Aug. 16, 2007;26(38):5564-76.
Surani et al., A New Route to Rejuvenation, nature 443:284-285, Sep. 21, 2006.
Tada et al., Nuclear Reprogramming of Somatic Cells by in vitro Hybridization With ES Cells, Current Biology 11(19):1553-58, 2001.
Takahashi et al. Induction of pluripotent stem cells from adult human fibroblasts by defined factors. Cell. Nov. 30, 2007;131(5):861-72.
Takahashi et al. Induction of pluripotent stem cells from fibroblast cultures. Nat Protoc. 2007;2(12):3081-9.
Takahashi et al. Induction of pluripotent stem cells from mouse embryonic and adult fibroblasts by defined factors. Cell. Aug. 25, 2006; 126(4):663-676.
Takahashi et al., Induced Pluripotent Stem Cells, Jikken Igaku (Experimental Medicine) 26(5):35-40, 2008.
Takahashi et al., Role of ERas in Promoting Tumour-Like Properties in Mouse Embryonic Stem Cells, Nature 423:541-45, 2003.
Takahashi, K. et al. "Human induced pluripotent stem cells on autologous feeders." PLoS One. Dec. 2, 2009;4(12):e8067.PMID: 19956543 [PubMed—indexed for MEDLINE]Free PMC ArticleFree textRelated citations.
Takeda et al., Characterization of Dental Pulp Stem Cells of Human Tooth Germs, Journal of Dental Research, 2008, vol. 87, pp. 676-681.
Takeda et al., Human Oct3 Gene Family: cDNA Sequences, Alternative Splicing, Gene Organization, Chromosomal Location, and Expression at Low Levels in Adult Tissues, Nucleic Acids Research 20(17):4613-4620, 1992.
Tan et al. Changing viral tropism using immunoliposomes alters the stability of gene expression: implications for viral vector design. Mol Med. Mar.-Apr. 2007; 13(3-4):216-26.
Tantin et al. High-throughput biochemical analysis of in vivo location data reveals novel distinct classes of POU5FI(Oct4)/DNA complexes. Genome Res. Apr. 2008;18(4):631-9.
Taranger et al., Induction of Dedifferentiation, Genomewide Transcriptional Programming, and Epigenetic reprogramming by Extracts of Carcinoma and Embryonic Stem Cells, Mol. Biol. Cell 16:5719-35, 2005.
Tateno et al., Heterogeneity of Growth Potential of Adult Rat Hepatocytes in vitro, Hepatology 31(1):65-74, 2000.
The Japan Times. Bayer team makes stem cells from skin. Apr. 12, 2008. Available at http://search.japantimes.co.jp/cgi-bin/nn20080412a5.html. Accessed May 19, 2009.
Thomson et al. Embryonic Stem Cell Lines Derived from Human Blastocysts. Science. Nov. 1998;282(5391):1145.
Time. The Top 10 Everything of 2008—1. First Neurons Created from ALS Patients. Available at http://www.time.com/time/specials/2008/top10/article/0,30583,1855948_1863993,00.html. Accessed Dec. 15, 2008.
Tokuzawa et al. Utilization of Digital Differential Display to Identify Novel Targets of Oct3/4. In: Turksen, K., ed. Embryonic Stem Cell Protocols: vol. I: Isolation and Characterization. Humana Press; 2nd ed. Edition. Feb. 15, 2006: 223-231.
Tokuzawa et al., Fbx15 Is a Novel Target of Oct3/4 but is Dispensable for Embryonic Stem Cell Self-Renewal and Mouse Development, Mol. Cell Biol. 23(8):2699-718, 2003.
Trompeter, et. al. Rapid and highly efficient gene transfer into natural killer cells by nucleofection. J Immunol Methods. Mar. 1, 2003 ;274(1-2):245-56.
Troyanskaya et al. Nonparametric methods for identifying differentially expressed genes in microarray data. Bioinformatics. 2002;18(11): 1454-1461.
Tsai et al. In vivo immunological function of mast cells derived from embryonic stem cells: an approach for the rapid analysis of even embryonic lethal mutations in adult mice in vivo. Proc Natl Acad Sci Aug. 1, 2000;97(16):9186-90.
Tsubooka et al. "Roles of Sall4 in the generation of pluripotent stem cells from blastocysts and fibroblasts." Genes Cells. Jun. 2009;14(6):683-94. Epub May 19, 2009.PMID: 19476507 [PubMed—indexed for MEDLINE]Related citations.
Tsunoda, Y., et al., The Recent Progress on Nuclear Transfer in Mammals, Zoological Science 17:1177-1184, 2000.
Tzukerman et al. Identification of a novel transcription factor binding element involved in the regulation by differentiation of the human telomerase (hTERT) promoter. Mol Biol Cell. Dec. 2000;11(12):4381-91.
Ulloa-Montoya et al., "Culture Systems for Pluripotent Stem Cells," *Journal of Bioscience and Bioengineering*, vol. 100(1), pp. 12-27 (2005).
Ulloa-Montoya et al. Comparative transcriptome analysis of embryonic and adult stem cells with extended and limited differentiation capacity. Genome Biol. 2007;8(8):R163.
Vallier et al. Activin/Nodal and FGF pathways cooperate to maintain pluripotency of human embryonic stem cells. J Cell Sci. Oct. 1, 2005;118(Pt 19):4495-509.
Vermeesch et al. Guidelines for molecular karyotyping in constitutional genetic diagnosis. Eur J Hum Genet. Nov. 2007;15(11):1105-14.
Verrey et al., CATs and HATs: The SLC7 Family of Amino Acid Transporters, Pflugers Archive—European Journal of Physiology, DOI 10.1007/s00424-003-1086-Z, pp. 1-23, published online Jun. 11, 2003.
Vintersten et al., Mouse in Red: Red Fluorescent Protein Expression in Mouse ES Cells, Embryos, and Adult Animals, Genesis 4041-46, 2004.
Viswanathan et al., Selective Blockade of MicroRNA Processing by Lin28, Science 320:97-100, 2008.
Vogel, G. Breakthrough of the year. Reprogramming Cells. Science. Dec. 19, 2008;322(5909): 1766-7.
Wadia et al., Protein Transduction Technology, Curr. Opin. Biotechnol. 13:52-56, 200.
Wagner et al. Mesenchymal stem cell preparations—comparing apples and oranges. Stem Cell Rev. Dec. 2007;3(4):239-48.
Wakao et al., "Multilineage-Differentiating Stress-Enduring (Muse) Cells Are a Primary Source of Induced Pluripotent Stem Cells in Human Fibroblasts," PNAS Early Edition, pp. 1-6, May 31, 2011, available at www.pnas.org/cgi/content/short/1100816108.
Wakayama et al., Differentiation of Embryonic Stem Cell Lines Generated From Adult Somatic Cells by Nuclear Transfer, Science 292:740-43, 2001.
Wakayama et al., Full-Term Development of Mice From Enucleated Oocytes Injected With Cumulus Cell Nuclei, Nature 394:369-74, 1998.
Wang et al. Inhibition of caspase-mediated anoikis is critical for bFGF-sustained culture of human pluripotent stem cells. J Biol Chem. Oct. 16, 2009. [Epub ahead of print].
Wang et al., A Protein Interaction Network for Pluripotency of Embryonic Stem Cells, Nature 444:364-68, 2006.
Watanabe et al. A ROCK inhibitor permits survival of dissociated human embryonic stem cells. Nat Biotechnol. 2007; 25, 681-686.
Watson et al. Identifying Genes Regulated in a Myc-dependent Manner. J Biol Chem. Oct. 4, 2002;277(40):36921-30.
Werbowetski-Ogilvie et al. Characterization of human embryonic stem cells with features of neoplastic progression. Nat Biotechnol. Jan. 2009;27(1):91-7.
Wernig et al. c-Myc is dispensable for direct reprogramming of mouse fibroblast. Cell Stem Cell. 2008; 2, 10-12.
Wernig et al. In vitro reprogramming of fibroblasts into a pluripotent ES-cell-like state. Nature. Jul. 19, 2007;448:318-324.

(56) References Cited

OTHER PUBLICATIONS

Wernig et al., Neurons Derived From Reprogrammed Fibroblasts Functionally Integrate Into the Fetal Brain and Improve Symptoms of Rats With Parkinson's Disease, Proc. Natl. Acad. Sci. U.S.A. 105(15):5856-5861, 2008.
What are adult stem Cells? Stem Cell Information. The National Institutes of Health resource for stem cell research. 2007. Available at: http://stemcells.nih.gov/info/basics/basics4.asp. Accessed Jun. 4, 2007.
Wilmut et al., Viable Offspring Derived From Fetal and Adult Mammalian Cells, Nature 385:810-13, 1997.
Woltjen et al., PiggyBac Transposition Reprograms Fibroblasts to Induced Pluripotent Stem Cells, Nature, Mar. 1, 2009, vol. 458, Issue 7239, pp. 766-770.
Wu et al. Origins and Fates of Cardiovascular Progenitor Cells. Cell. Feb. 22, 2008; 132(4):537-543.
Wu et al., Sall4 Interacts With Nanog and Co-Occupies Nanog Genomic Sites in Embryonic Stem Cells, J. Biol., Chem., 281(34):24090-24094, 2000.
Xu et al. BMP4 initiates human embryonic stem cell differentiation to trophoblast. Nat Biotechnol. Dec. 2002;20(12):1261-4.
Xu et al. Random mutagenesis libraries: optimization and simplification by PCR. Biotechniques. Dec. 1999;27(6):1102, 1104, 1106, 1108.
Xu et al., Basic FGF and Suppression of BMP Signaling Sustain Undifferentiated Proliferation of Human ES Cells, Nat. Methods 2(3):185-90, 2005.
Yamanaka et al., "Nuclear reprogramming to a pluripotent state by three approaches." Nature. Jun. 10, 2010;465(7299):704-12. Review.PMID: 20535199 [PubMed—indexed for MEDLINE]Related citations.
Yamanaka et al., Mouse Sen'iga Saibo Kara Yudo Tansosei Kansaibo o Tsukuru (Induction of Pluripotent Stem Cells From Mouse Fibroblast Cultures) Tanpakushitsu Kakusan Koso (Protein, Nucleic Acid and Enzyme) 51(15):2346-51, 2006.
Yamanaka S., "An interview with . . . Shinya Yamanaka. Interview by Mary Muers." Nat Rev Genet. Jun. 2010;11(6):390. Epub May 5, 2010. No abstract available. PMID: 20442716 [PubMed—indexed for MEDLINE]Related citations.
Yamanaka S., "Patient-specific pluripotent stem cells become even more accessible" Cell Stem Cell. Jul. 2, 2010;7(1):1-2.PMID: 20621038 [PubMed—in process]Related citations.
Yamanaka S., "Pluripotency and nuclear reprogramming." Philos Trans R Soc Lond B Biol Sci. Jun. 27, 2008;363(1500):2079-87. Review.PMID: 18375377 [PubMed—indexed for MEDLINE]Free PMC ArticleFree textRelated citations.
Yamanaka S., "Symposium: Nuclear reprogramming and the control of differentiation in mammalian embryos. Introduction." Reprod Biomed Online. Jan. 2008;16(1):11-2. No abstract available. PMID: 18252042 [PubMed—indexed for MEDLINE]Related citations.
Yamanaka, Pluripotency of Differentiation and miRNA, The Journal of Biochemistry, vol. 79, No. 11, Abstract 3BT17 From the 80th Annual Meeting of the Japanese Biochemical Society, Nov. 25, 2007, along with an English language translation thereof.
Yamanaka, S. Induction of Pluripotent stem cells from mouse fibroblasts by four transcription factors. Cell Prolif. 2008;41 (Suppl. 1): 51-56.
Yamanaka, S. Strategies and new developments in the generation of patient-specific pluripotent stem cells. Cell Stem Cell. Jun. 7, 2007;1(1):39-49.
Yamanaka, S., "A fresh look at iPS cells." Cell. Apr. 3, 2009;137(1):13-7.PMID: 19345179 [PubMed—indexed for MEDLINE]Related citations.
Yamanaka, S., "Ekiden to iPS Cells." Nat Med. Oct. 2009;15(10):1145-8. No abstract available. PMID: 19812575 [PubMed—indexed for MEDLINE]Related citations.
Yamanaka, S., "Elite and stochastic models for induced pluripotent stem cell generation." Nature. Jul. 2, 2009;460(7251):49-52.PMID: 19571877 [PubMed—indexed for MEDLINE]Related citations.
Yamanaka, S., "Induction of Pluripotency by Defined Factors—The History of iPS Cells", Gairdner Award acceptance speech, presented on or about Oct. 29, 2009.
Yamanaka, S., "Induction of Pluripotency by Defined Factors", lecture presented on or about Oct. 29, 2009.
Yamanaka, S., Induction of Pluripotent Stem Cells From Mouse Fibroblasts by Four Transcription Factors, Cell Proliferation, 2008, vol. 41, Issue (Suppl. 1), pp. 51-56.
Yamane et al. Derivation of melanocytes from embryonic stem cells in culture. Dev. Dyn. 1999;216:450-458.
Yamashita et al. Flk1-positive cells derived from embryonic stem cells serve as vascular progenitors. Nature. Nov. 2, 2000;408(6808):92-6.
Yang et al., Nuclear Reprogramming of Cloned Embryos and Its Implications for Therapeutic Cloning, Nat. Genet. 39(3):295-302, 2007.
Yee et al. Generation of high-titer pseudotyped retroviral vectors with very broad host range. Methods Cell Biol. 1994;43 Pt A:99-112.
Ying et al., BMP Induction of ID Proteins Suppresses Differentiation and Sustains Embryonic Stem Cell Self-Renewal in Collaboration With STAT3, Cell 115:281-92, 2003.
Ying et al., The MicroRNA: Overview of the RNA Gene That Modulates Gene Functions, Methods in Molecular Biology, MicroRNA Protocols, vol. 342, pp. 1-18, Humana Press, 2006.
Yoshida et al. "Hypoxia enhances the generation of induced pluripotent stem cells." Cell Stem Cell. Sep. 4, 2009;5(3):237-41. Epub Aug. 27, 2009. No abstract available. PMID: 19716359 [PubMed—indexed for MEDLINE]Related citations.
Yoshida et al., "Recent stem cell advances: induced pluripotent stem cells for disease modeling and stem cell-based regeneration." Circulation. Jul. 6, 2010;122(1):80-7. Review. No abstract available. PMID: 20606130 [PubMed—indexed for MEDLINE]Related citations.
Yu et al. Induced pluripotent stem cell lines derived from human somatic cells. Science. Dec. 21, 2007;318(5858):1917-20.
Yu et al., Human Induced Pluripotent Stem Cells Free of Vector and Transgene Sequences, Science 324:797-801, 2009.
Yuasa et al. Transient inhibition of BMP signaling by Noggin induces cardiomyocyte differentiation of mouse embryonic stem cells. Nat Biotechnol. May 2005;23(5):607-11.
Zhan et al. Conservation and variation of gene regulation in embryonic stem cells assessed by comparative genomics. Cell Biochem Biophys. 2005;43(3):379-405.
Zhang et al. In vitro differentiation of transplantable neural precursors from human embryonic stem cells. Nat Biotechnol. Dec. 2001;19(12):1129-33.
Zhang et al., MicroRNA: A New Player in Stem Cells, Journal of Cellular Physiology 209:266-269, 2006.
Zhao et al., "A human peripheral blood monocyte-derived subset acts as pluripotent stem cells," PNAS, vol. 100(5), pp. 2426-2431 (Mar. 4, 2003).
Zhao et al. Mechanisms and Functional Implications of Adult Neurogenesis. Cell. Feb. 22, 2008;132(4):645-660.
Zhao et al., "Two Supporting Factors Greatly Improve the Efficiency of Human iPSC Generation" Cell Stem Cell 3:475-79, 2008.
Zhou et al., Generation of Induced Pluripotent Stem Cells Using Recombinant Proteins, Cell Stem Cell 4:381-384, 2009.
Ziegler et al., The Cationic Cell-Penetrating Peptide CPPTAT Derived From the HIV-1 Protein TAT is Rapidly Transported into Living Fibroblasts: Optical, Biophysical, and Metabolic Evidence, Biochemistry 44:138-148, published online Dec. 14, 2004.
Extended European Search Report for European Patent Application No. 09738908.4, dated Jan. 28, 2013.
Extended European Search Report mailed on Feb. 21, 2012 in corresponding European patent app. No. 09763772.2 in 6 pages.
Office Action dated Feb. 10, 2012, issued in connection with Canadian Patent Application No. 2,632,142.
Notification of the Second Office Action dated Feb. 24, 2012, issued in connection with Chinese Patent Application No. 200880000834.5, 9 pages.
Examination report dated Dec. 11, 2012 and issued to related European application No. 10154817.0.

(56) References Cited

OTHER PUBLICATIONS

Office Action issued in European Patent Application No. 10154821.2, on Jun. 1, 2016.
Office Action mailed on Mar. 13, 2012, issued in connection with Japanese Patent Application No. 2007-550210.
Office Action issued in Japanese Patent Application No. 2010-506477, on Apr. 9, 2013.
Office Action dated Jun. 20, 2007, issued in connection with U.S. Appl. No. 10/861,040.
Office Action dated Oct. 4, 2010, issued in connection with U.S. Appl. No. 12/157,967.
Alberts, et al., Molecular Biology of the Cell, Fourth Ed., Garland Science, 2002, p. 22.
Aoi, T., et al., Generation of Pluripotent Stem Cells From Adult Mouse Liver and Stomach Cells, Science, vol. 321, pp. 699-702, Corrected Aug. 1, 2008.
Asai, et al., Modulation of Tumor Immunogenicity of Rat Glioma Cells by s-Myc Expression: Eradication of Rat Gliomas in Vivo, Cell Growth & Differentiation 5(11):1153-1158, Nov. 1984.
Bosman et al., Progress Toward the Clinical Application of Autologous Induced Pluripotent Stem Cells and Gene Repair Therapy for Treatment of Familial Hypercholesterolemia. The International Liver Congress 2011, 2011, abstract.
Brimble, et al., Karyotypic Stability, Genotyping, Differentiation, Feeder-Free Maintenance, and Gene Expression Sampling in Three Human Embryonic Stem Cell Lines Derived Prior to Aug. 9, 2001, Stem Cells Develop. 13:585-596, 2004.
Catalog of ES Cell Culture Medium, Cosmo Bio News 49:5, 2005.
Chiba Medical Journal 84(1):17, Feb. 2006.
Clerc, et al., The B-cell-Specific Oct-2 Protein Contains POU box- and Homeo Box-Type Domains, Genes Dev. 2(12A):1570-1581, Dec. 1988.
Cowan et al., Nuclear Reprogramming of Somatic Cells After Fusion With Human Embryonic Stem Cells, Science 309:1369-73, 2005.
Cyranoski et al., Simple Switch Turns Cells Embryonic (Correction), Nature, Jun. 21, 2007, vol. 447, pp. 897.
Doetschman, et al., Establishment of Hamster Blastocyst-Derived Embryonic Stem Cells, 127 Development 224 (1988).
Duinsbergen (Experimental Cell Res. Jul. 9, 2008, vol. 314, p. 3255-3263).
Ebert, et al., Induced Pluripotent Stem Cells from a Spinal Muscular Atrophy Patient, Nature 457(7227):277280, Jan. 15, 2009.
Ekwall et al., "Toxicity Tests with Mammalian Cell Cultures," Short-term Toxicity Tests for Non-genotoxic Effects, Edited by P. Bourdeau et al., SCOPE, John Wiley & Sons Ltd., pp. 75-97 (1990).
Eminli (Stem Cells, Jul. 17, 2008, vol. 26, p. 2467-2474).
Feng (Cell Stem Cell, Apr. 3, 2009, vol. 4, p. 301-312).
Furler, et al., Recombinant AAV Vectors Containing the Foot and Mouth Disease Virus 2A Sequence Confer Efficient Bicostronic Gene Expression in Cultured Cells and Rat Substantia Nigra Neurons, Gene Therapy 8:864-873, 2001.
Fusaki, N., et al., Efficient Induction of Transgene-Free Human Pluripotent Stem Cells Using a Vector Based on Sendai Virus, an RNA Virus That Does Not Integrate Into the Host Genome, Proc. Jpn. Acad., Ser. B, 85:348-362, 2009.
Gandarillas et al., "c-Myc promotes differentiation of human epidermal stem cells," Genes & Dev., vol. 11, pp. 2869-2882 (1997). (Retrieved from the Internet: URL:http://genesdev.cshlp.org/content/11/21/2869.full [retrieved on May 18, 2016]).
Gonzalez, et al., "Generation of mouse-induced pluripotent stem cells by transient expression of a single nonviral polycistronic vector," PNAS, vol. 106(22), pp. 8919-8922 (Jun. 2, 2009).
Grignani et al., "Negative autoregulation of c-myc gene expression is inactivated in transformed cells," The EMBO Journal, vol. 9(12), pp. 3913-3922 (1990).
Hoffman, L., and M. Carpenter, Characterization and Culture of Human Embryonic Stem Cells, Nature Biotechnology 23:699, 2005.
Hotta et al., "Retroviral Vector Silencing During iPS Cell Induction: An Epigenetic Beacon that Signals Distinct Pluripotent States," Journal of Cellular Biochemistry, vol. 105, pp. 940-948 (2008).
Iannaccone, et al., Pluripotent Embryonic Stem Cells From the Rat Are Capable of Producing Chimeras, Developmental Biology 163(288), 1994.
Ingvarsson, et al., Structure and Expression of B-myc, A New Member of the myc Gene Family, Mol. Cell. Biol. 8(8):3168-3174, Aug. 1988.
Kanai-Azuma, et al., "Depletion of Definitive Gut Endoderm in Sox17-Null Mutant Mice" Development (2002) 129: 2367-2379.
Kim et al., Pluripotent Stem Cells Induced From Adult Neural Stem Cells by Reprogramming with Two Factors, Nature 454:646-650, 2008.
Kishi et al., Requirement of Sox2-Mediated Signaling for Differentiation of Early Xenopus Neuroectoderm, Development 127:791-800, 2000.
Klf1 description, Wikipedia, 2014.
Kozarsky et al., Adenovirus-Mediated Correction of the Genetic Defect in Hepatocytes from Patients with Familial Hypercholesterolemia Somatic Cell Molecular Genetics, 1993, vol. 19 pp. 449-458.
Lee, Molecular and Cell. Biol., Oct. 2004, vol. 24, No. 19, p. 8428-8436.
Li, Yan, Expansion of Human Embryonic Stem Cells in Defined Serum-Free Medium Devoid of Animal-Derived Products, published online Jun. 21, 2005 in Wiley InterScience, www.interscience.wiley.com.
Li, Ying et al., Transduction of Passaged Human Articular Chondrocytes with Adenoviral, Retroviral, and Lentiviral Vectors and the Effects of Enhanced Expression of Sox9, Tissue Eng. 10:575-584, 2004.
Luke, G.A., 2012, Translating 2A Research into Practice, Innovations in Biotechnology, Agbo, E.C. (Ed.), InTech, available from: http://www.intechopen.com/booksinnovations-in-biotechnology/translating/translating-2a-research, 2012.
Miyamoto, et al., Reprogramming Events of Mammalian Somatic Cells Induced by Xenopus Laevis Egg Extracts Molecular Reproduction and Development 74:1268-1277, 2007.
Nakagawa et al., "Generation of induced pluripotent stem cells without Myc from mouse and human fibroblasts," Nature Biotechnology, vol. 26(1), pp. 101-106 (Jan. 2008).
Niwa, et al., Phenotypic Complementation Establishes Requirements for Specific POU Domain and Generic Transactivation Function of Oct-3/4 in Embryonic Stem Cells, Molecular and Cellular Biology, 22:1526-1536, 2002.
Park, In-Hyun, et al., "Reprogramming of Human Somatic Cells to Pluripotency With Defined Factors," Nature 451:141-146, 2008.
Pear et al. Production of high-titer helper-free retroviruses by transient transfection. Proc. Natl. Acad. Sci. USA, vol. 90, pp. 8392-8396 (1993).
Rybkin, et al., Journal of Biological Chemistry 278:15927-15934, 2003.
Schöler, et al., A Family of Octamer-Specific Proteins Present During Mouse Embryogenesis: Evidence for Germline-Specific Expression of an Oct Factor, EMBO J. 8(9):2543-2550, Sep. 1989.
Stoykova, et al., Mini-Oct and Oct-2c: Two Novel, Functionally Diverse murine Oct-2 Gene Products are Differentially Expressed in the CNS, Neuron 8(3):541-58, Mar. 1992.
Strelchenko, N., Bovine Pluripotent Stem Cells, Theriogenology 45:131, 1996.
Swift, et al., Rapid Production of Retroviruses for Efficient Gene Delivery to Mammalian Cells Using 293T Cell-Based System, Current Protocols in Immunology 31(Supp.):10.17.1410.17.29, 1999.
Szymczak, A., et al., Correction of Multi-Gene Deficiency in vivo Using a Single 'Self-Cleaving' 2A Peptide-Based Retroviral Vector, Nature Biotechnology 22:589-594, 2002.
Takahashi et al., "Induction of Pluripotent Stem Cells from Mouse Embryonic and Adult Fibroblast Cultures by Defined Factors," Cell, vol. 126, pp. 663-676 (Aug. 25, 2006).
Thomson, et al., Isolation of a Primate Embryonic Stem Cell Line, 92 Proc. Natl. Acad. Sci. 7844 (1995).

(56) References Cited

OTHER PUBLICATIONS

Tokusumi, T., et al., Recombinant Sendai Viruses Expressing Different Levels of a Foreign Reporter Gene, Virus Research 86:33-38, 2002.

Tomioka et al., "Identification of Sox-2 regulatory region which is under the control of Oct-3/4-Sox-2 complex," Nucleic Acids Research, vol. 30(14), pp. 3202-3213 (2002).

van Viet, et al., Human KLF17 is a New Member of the Sp/KLF Family of Transcription Factors, Genomics 87(4):474-482, Apr. 2006; Epub Feb. 7, 2006.

Vector (in biotechnology), IUPAC Compendium of Chemical Terminology, 2nd Edition (1997).

Vennstrom, et al., Isolation and Characterization of c-myc, a Cellular Homolog of the Oncogene (v-myc) of Avian Myelocytomatosis Virus Strain 29, J. of Virol. 42(3):773-779, Jun. 1982.

Wei et al., "Sumoylation of Oct4 Enhances Its Stability, DNA Binding, and Transactivation," Journal of Biological Chemistry, vol. 282(29), pp. 21551-21560 (2007).

Wernig et al., c-Myc is Dispensable for Direct Reprogramming of Mouse Fibroblasts, Cell Stem Cell 2(1):10-12 (Jan. 2008), published online Dec. 13, 2007.

Yamanaka, et al. "Kekkan," Japanese Journal of Circulation Research, vol. 28(2), pp. 33-38 (2005).

Ying, microRNA, Jikken Purotokoru (microRNA Experimental Protocol), Yodosha Col. Ltd. 2008 pp. 2035.

Zhou et al., "Adenoviral Gene Delivery Can Reprogram Human Fibroblasts to Induced Pluripotent Stem Cells," Stem Cells, vol. 27, pp. 2667-2674 (2009).

Zhu et al., "Three-Color Flow Cytometry Analysis of Tricistronic Expression of eBFP, eGFP, and eYFP Using EMCV-IRES Linkages," Cytometry, vol. 37, pp. 51-59 (1999).

Office Action issued in Indian Patent Application No. 3564/CHENP/2008, dated Dec. 27, 2016.

Sperger et al., "Gene expression patterns in human embryonic stem cells and human pluripotent germ cell tumors," PNAS, vol. 100(23), pp. 13350-13355 (Nov. 11, 2003).

\* cited by examiner

FIG. 4 Morphology and expansion culture of human iPS clone 1-8

Surface antigen and gene expression analysis of clone 1-8

Gene expression analysis by RT-PCR in clone 1-8

FIG. 7 Global gene expression analysis – scatter plot

Global gene expression analysis – gene tree (1)

Global gene expression analysis – gene tree (2)

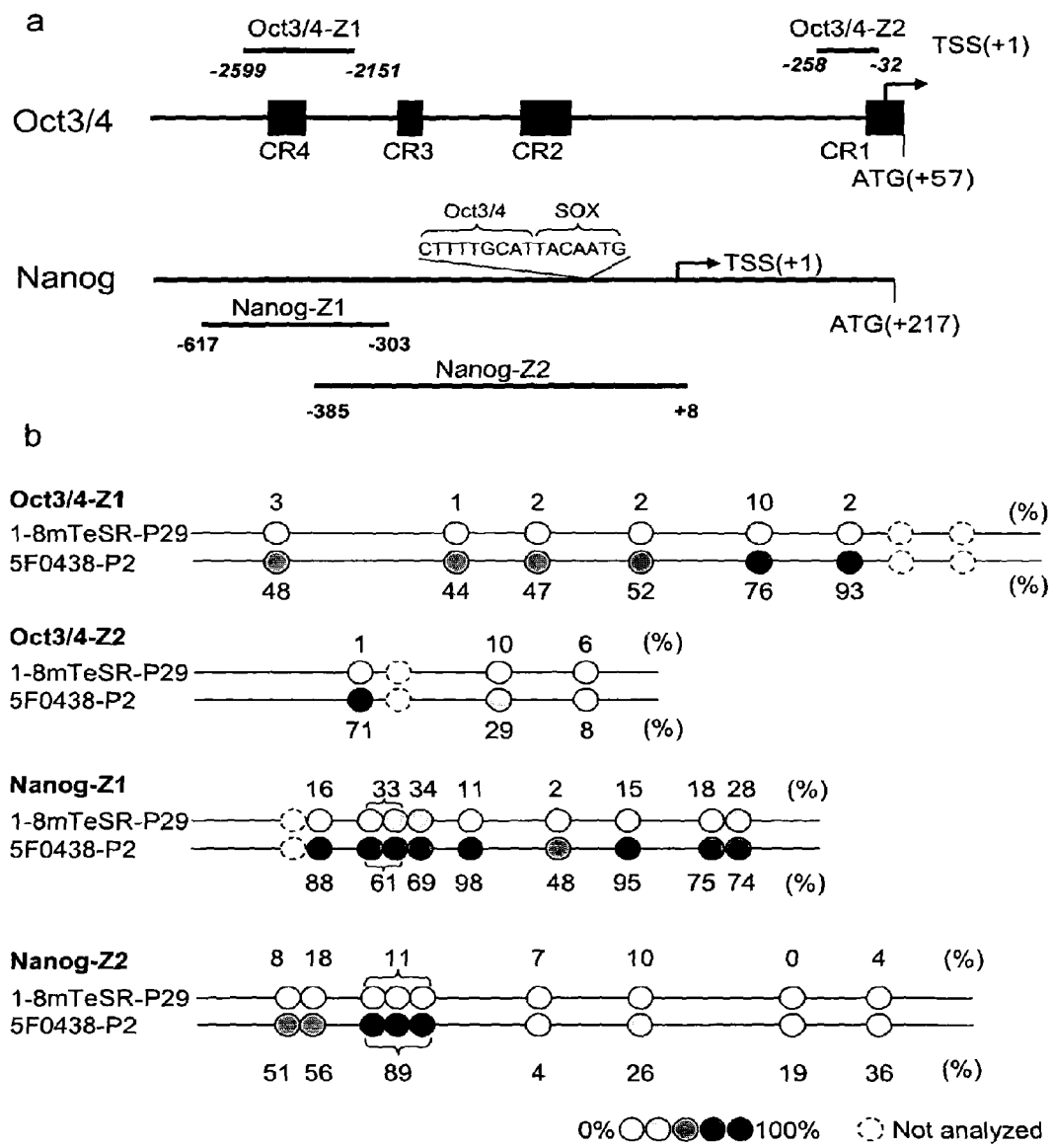
FIG.10 Methylation analysis of promoter regions in human iPS 1-8

FIG. 11 Teratoma formation (1)
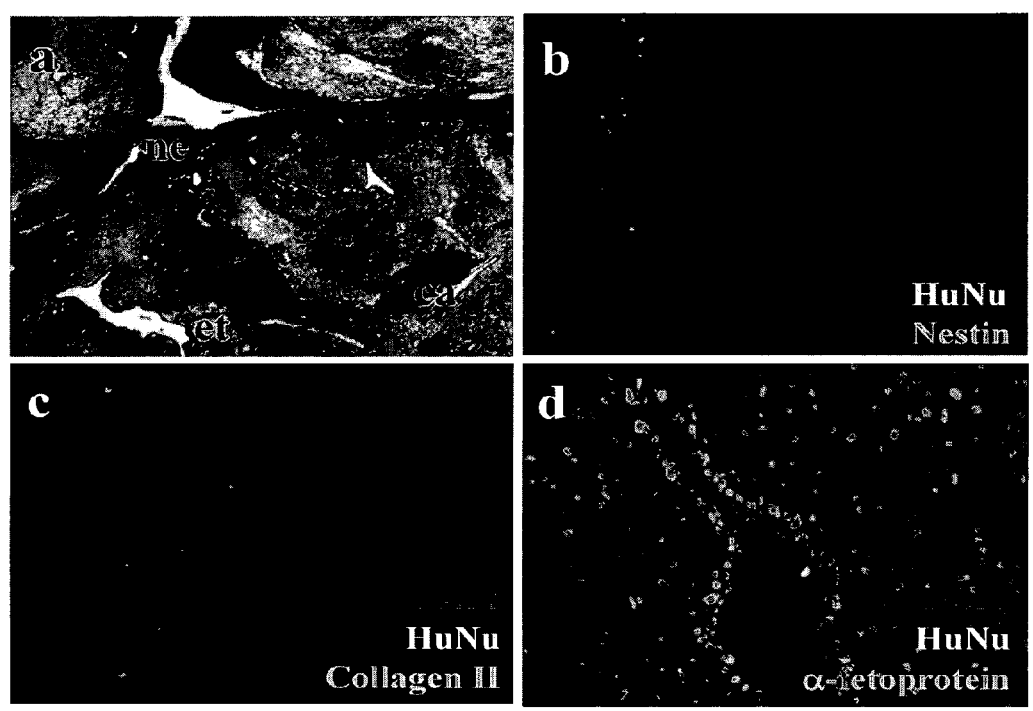
(T1, 56 d.p.i)

FIG. 12 Teratoma formation (2)
T-1
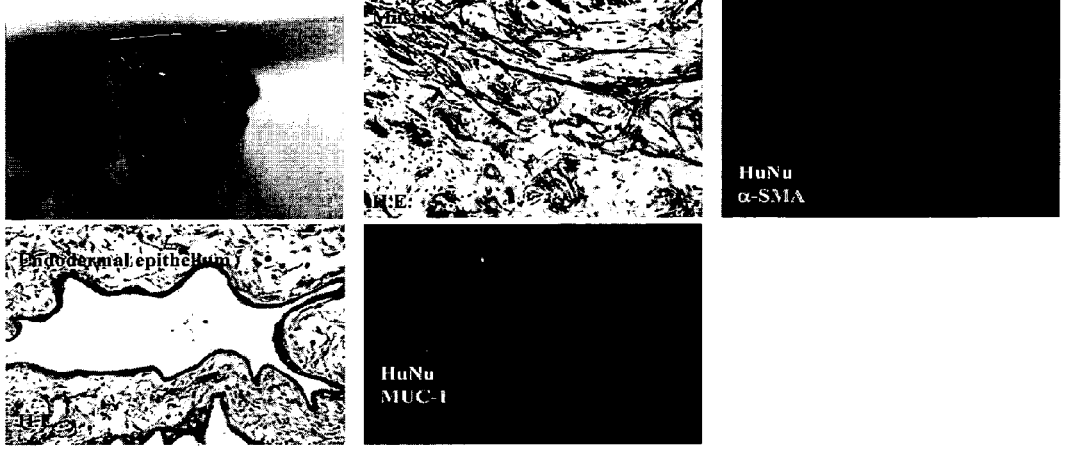
T-2
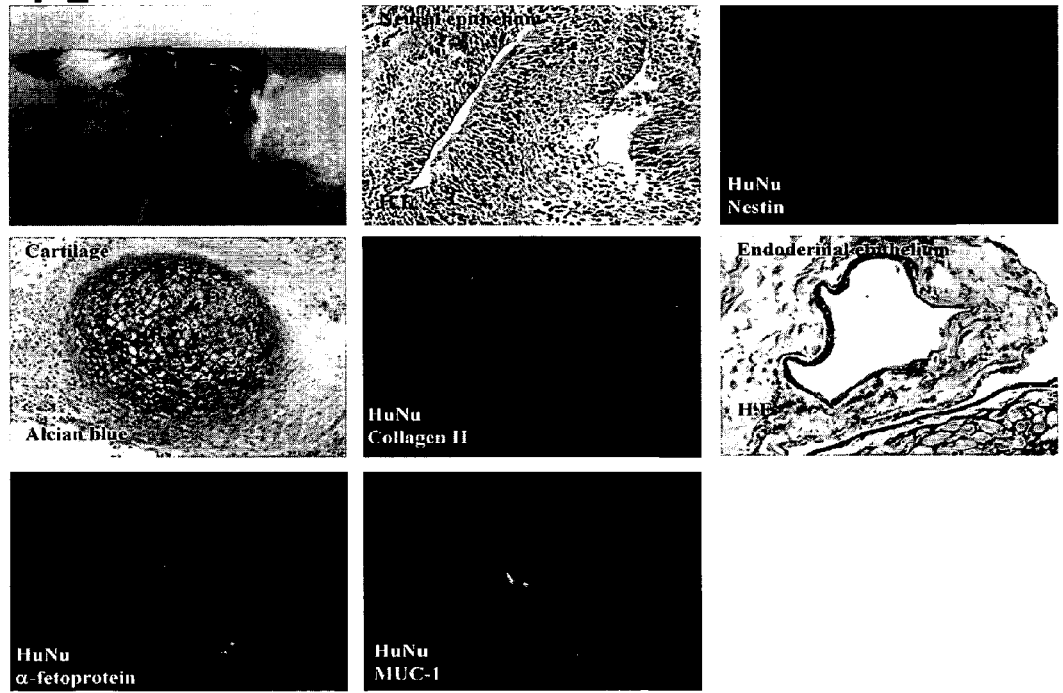

FIG. 13 Teratoma formation (3)
T-3
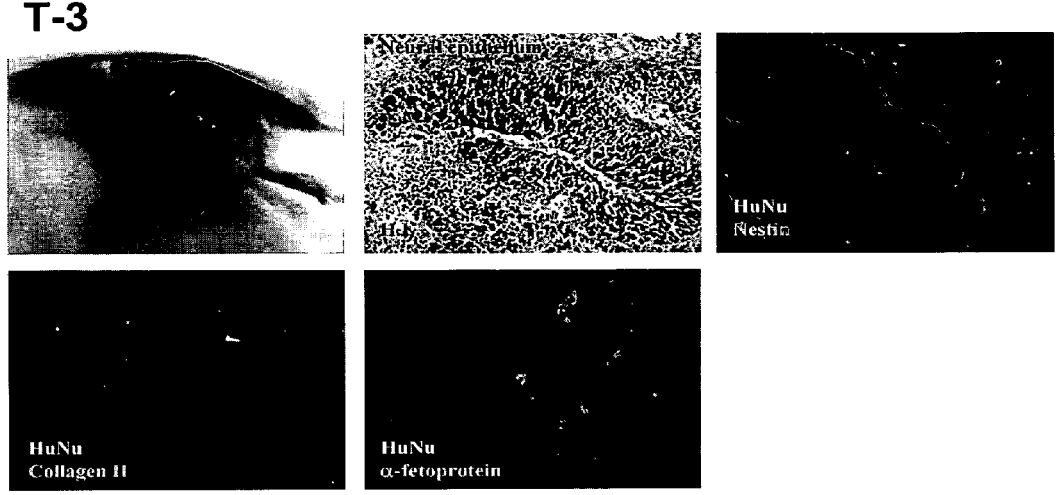
T-F1 and F2
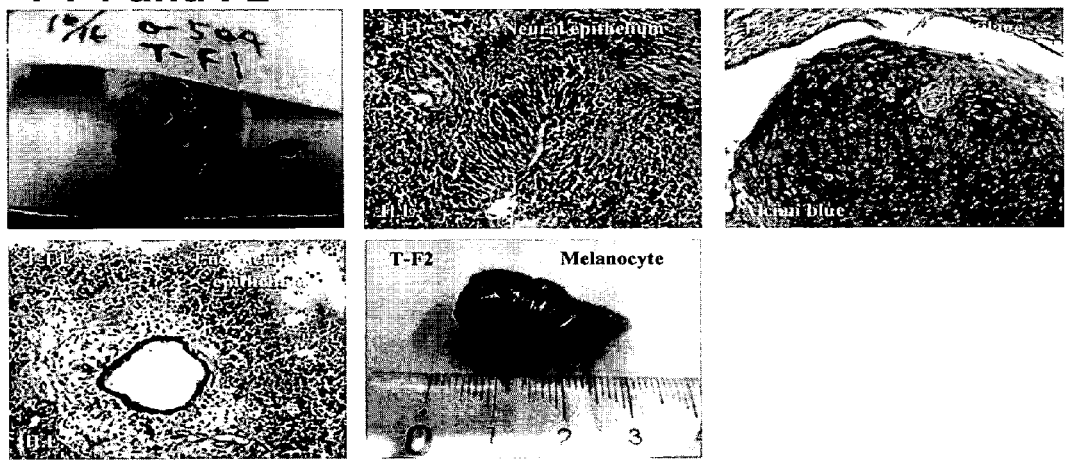

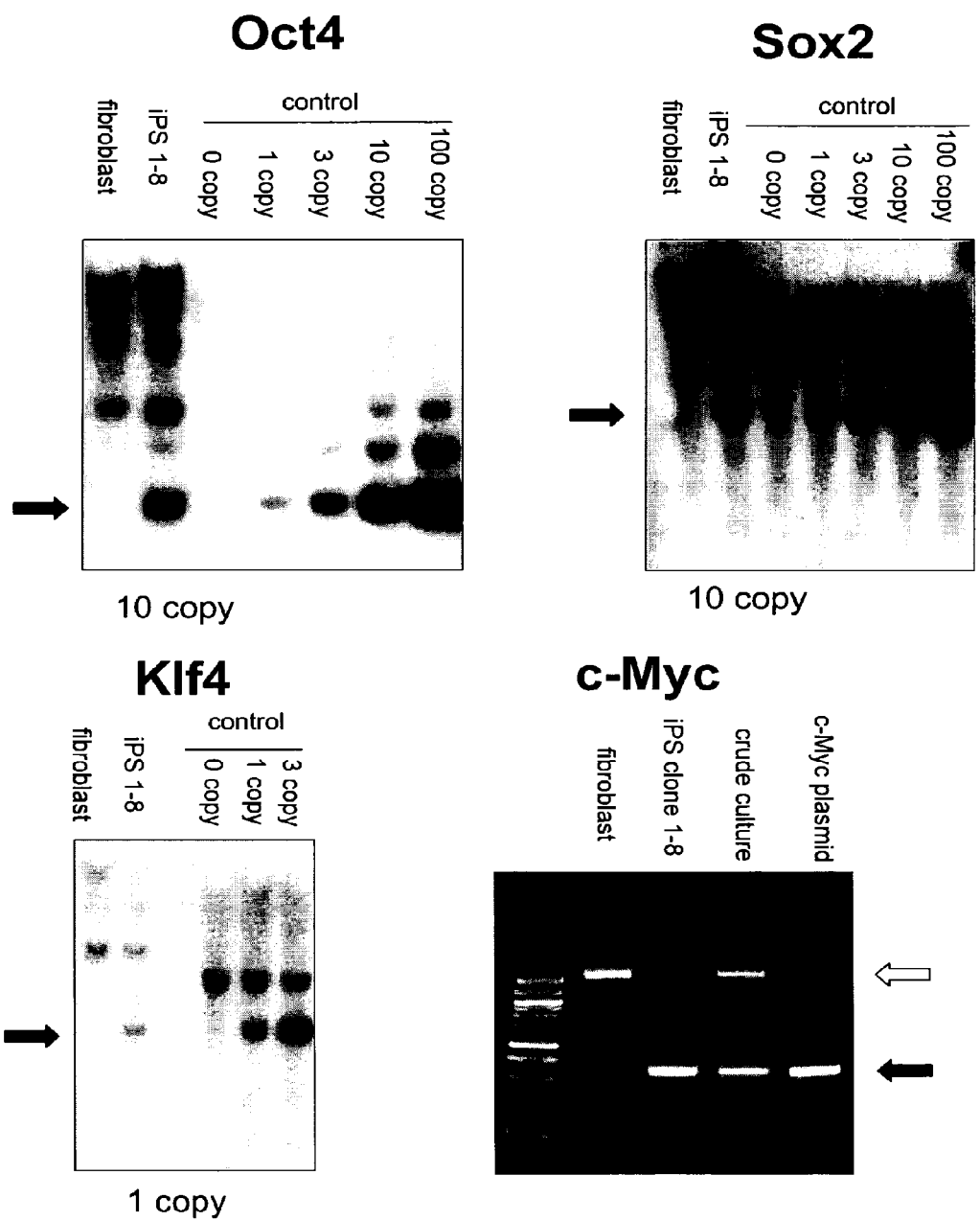
FIG. 14 Southern blot analysis

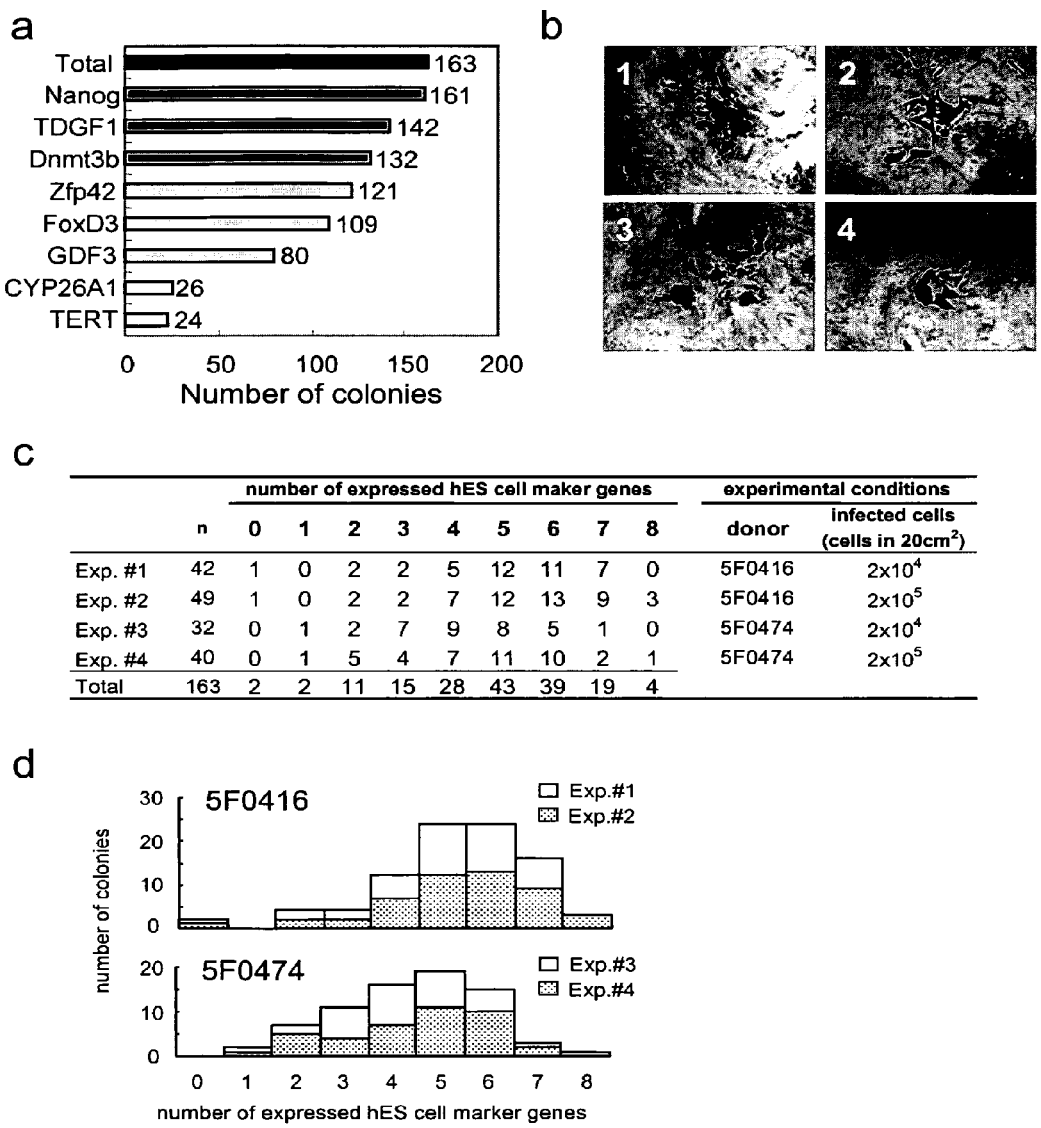
FIG. 15 hES maker gene expression in ALP positive colonies

FIG. 16 Morphologies of analyzed ALP positive colonies (1)
Group #1 (8 gene positive)
Group #2 (7 gene positive)
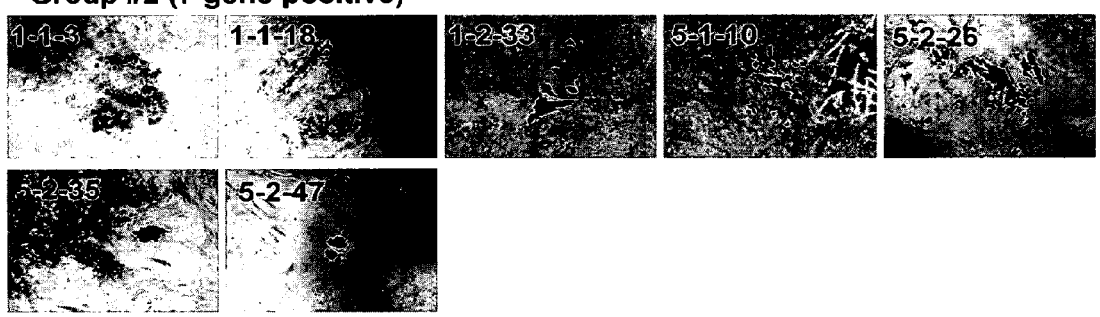
Group #3 (7 gene positive)
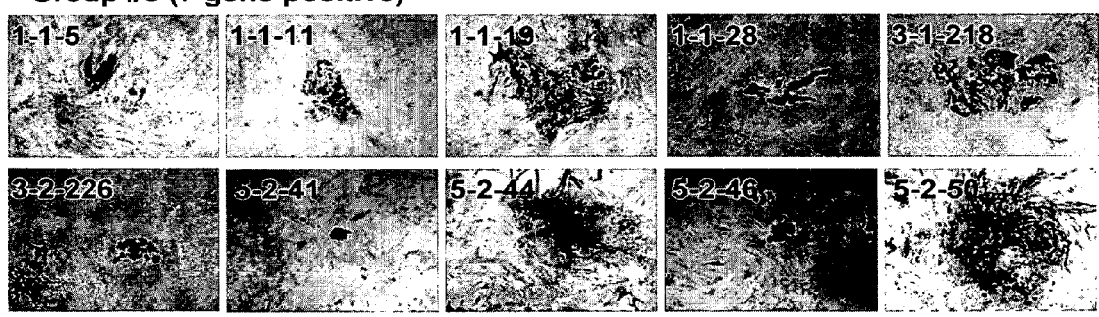
Group #4 (7 gene positive)

FIG. 17 Morphologies of analyzed ALP positive colonies (2)
Group #5 (6 gene positive)
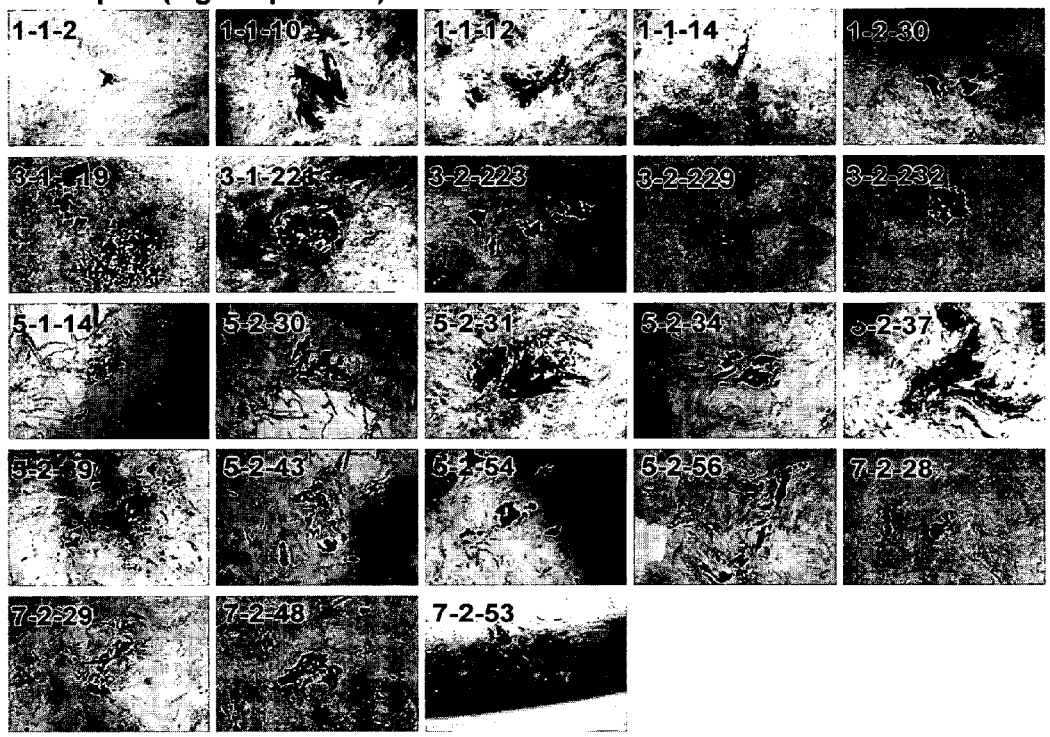
Group #6 (6 gene positive)
Group #7 (6 gene positive)
Group #8 (6 gene positive)

FIG. 18 Morphologies of analyzed ALP positive colonies (3)
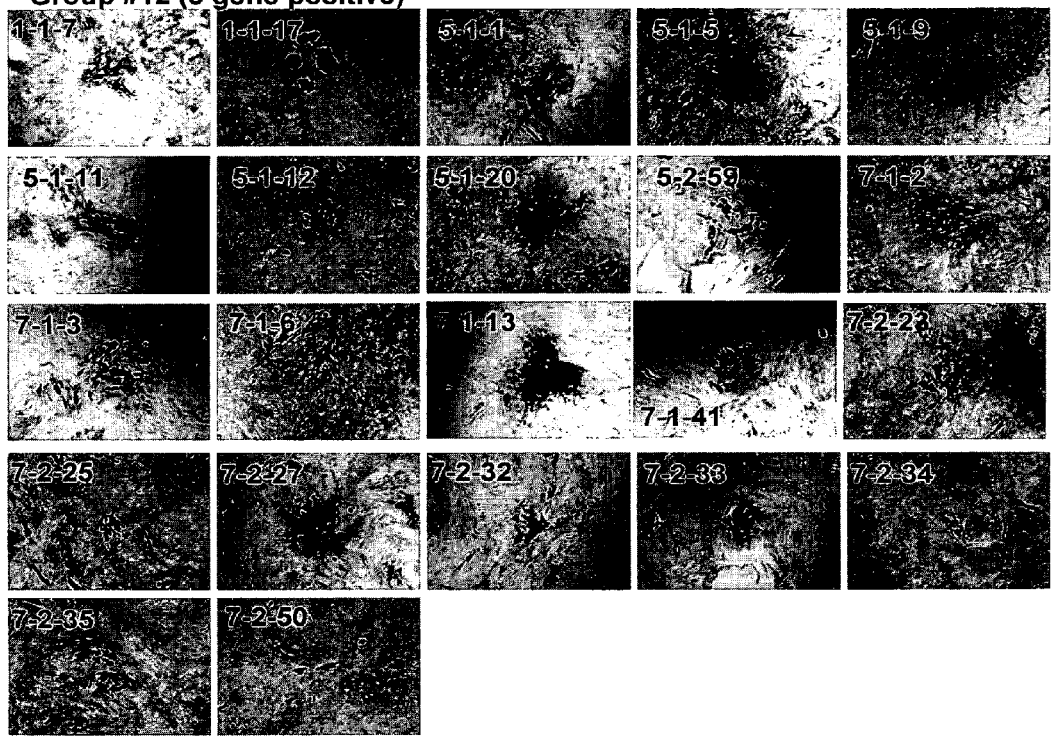
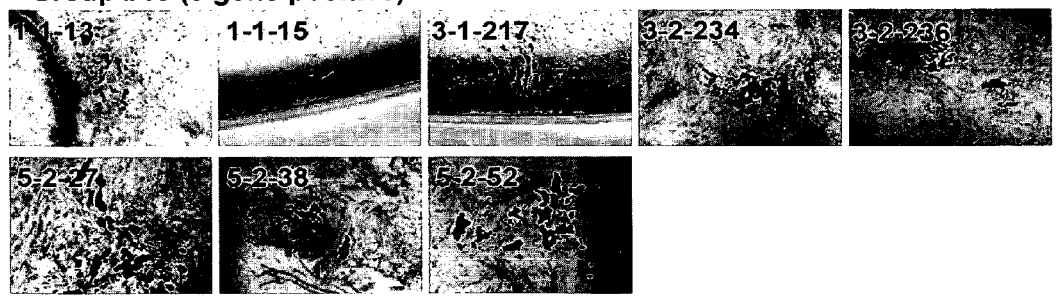

FIG. 19 Morphologies of analyzed ALP positive colonies (4)
Group #14 (5 gene positive)
Group #15 (5 gene positive)
Group #16 (5 gene positive)     Group #17 (5 gene positive)
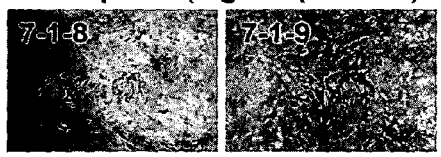 
Group #18 (5 gene positive)     Group #19 (5 gene positive)
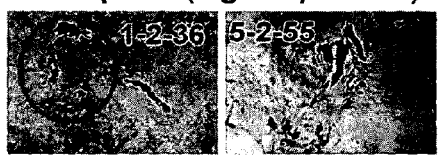 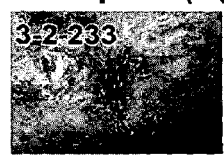
Group #20 (4 gene positive)
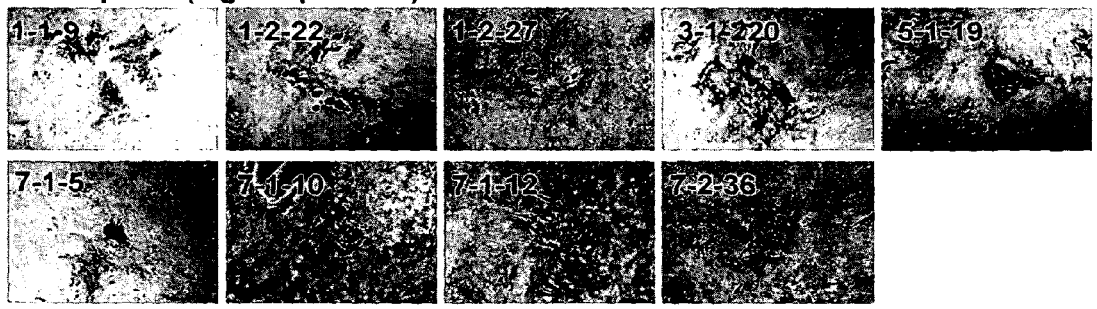

FIG. 20 Morphologies of analyzed ALP positive colonies (5)
Group #21 (4 gene positive)
Group #22 (4 gene positive)
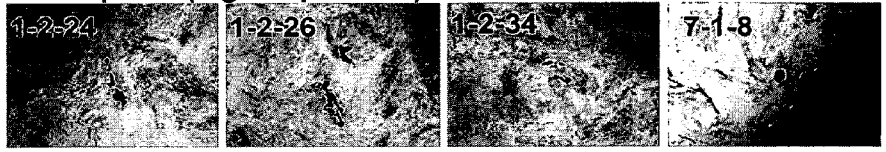
Group #23 (4 gene positive)
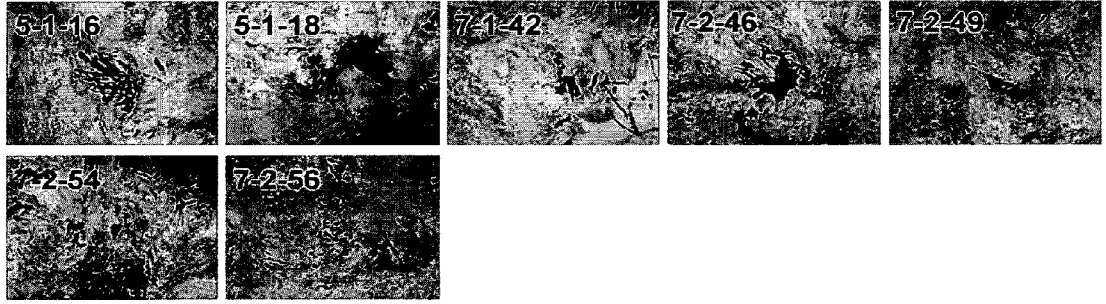
G-#24 (4 genes)   Group #25 (4 gene positive)   G-#26 (4 genes)
 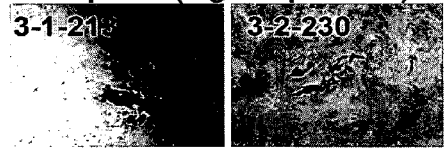 
G-#27 (3 genes)   Group #28 (3 gene positive)
 

FIG. 21 Morphologies of analyzed ALP positive colonies (6)
Group #29 (3 gene positive)
G-#30 (3 genes)    G-#31 (3 genes)    Group #32 (3 gene positive)
  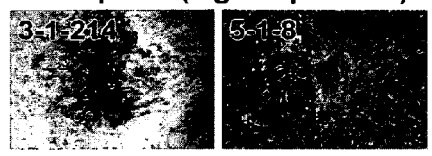
G-#33 (3 genes)    G-#34 (3 genes)    G-#35 (3 genes)
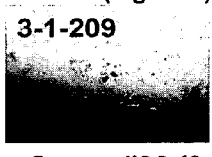 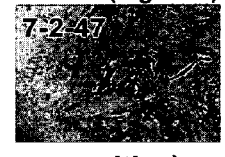 
Group #36 (2 gene positive)
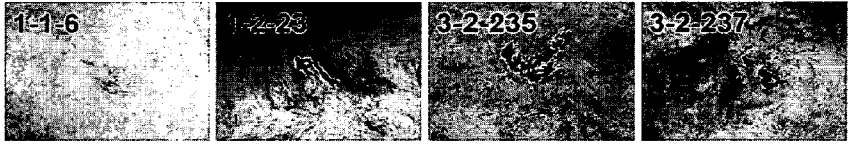
Group #37 (2 gene positive)
Group #38 (2 gene positive)
Group #39 (1 gene positive)    Group #40 (0 gene positive)
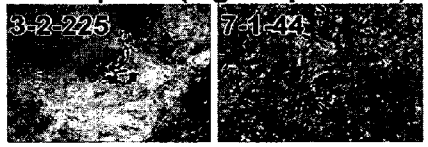 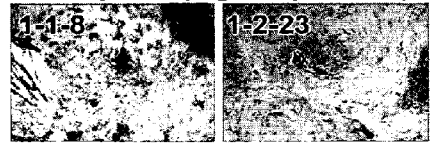

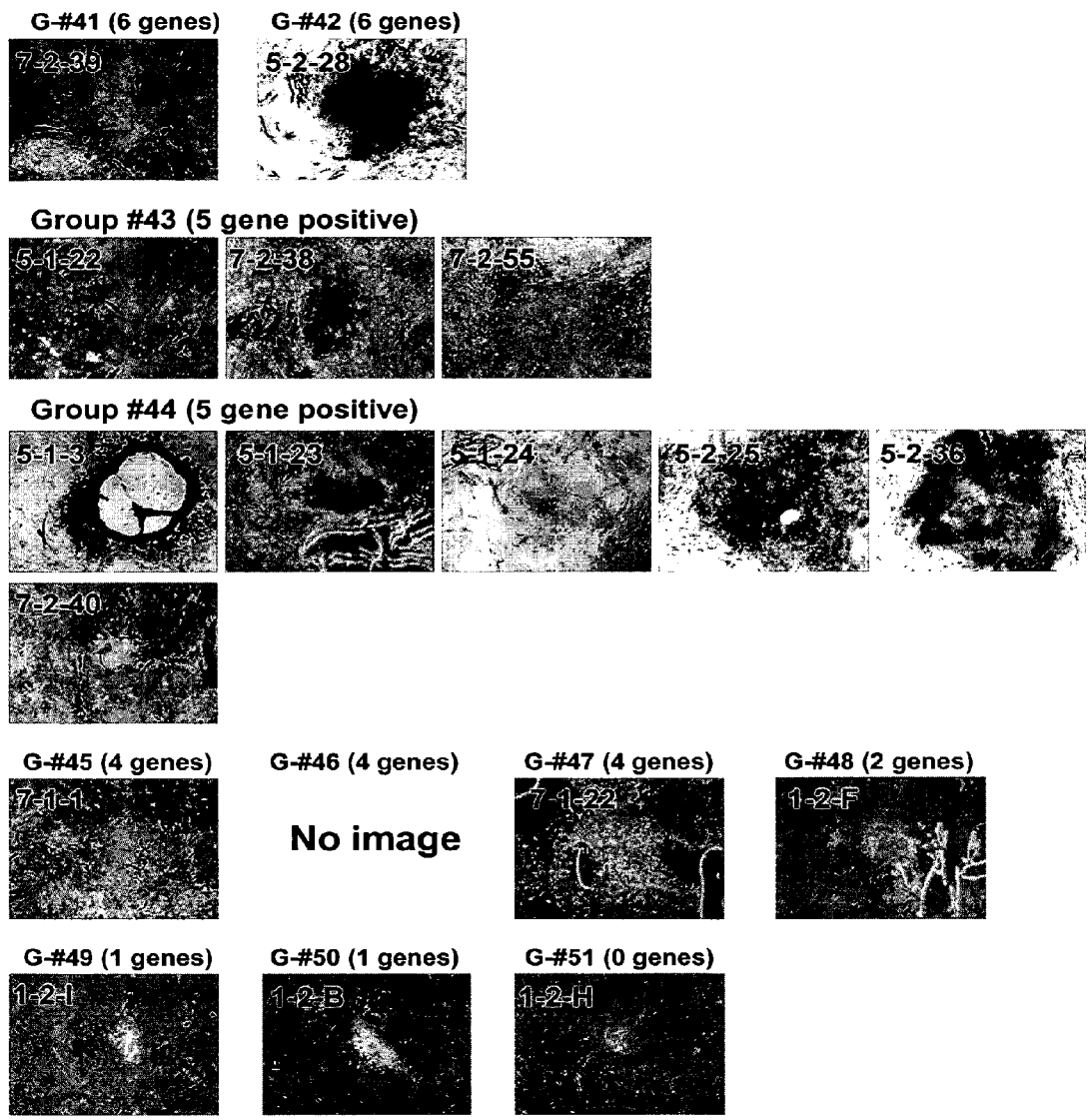
FIG. 22 Morphologies of analyzed ALP negative colonies

HUMAN PLURIPOTENT STEM CELLS INDUCED FROM UNDIFFERENTIATED STEM CELLS DERIVED FROM A HUMAN POSTNATAL TISSUE

TECHNICAL FIELD

The present invention relates to human pluripotent stem cells induced from stem cells present in a human postnatal tissue and its inducing method.

BACKGROUND ART

With the rapid aging of the society, diseases associated with tissue degeneration and tissue injury are rapidly increasing. Said diseases include cerebral infarction, myocardial infarction and renal failure that develop in an age-dependent manner due to the metabolic syndrome, Alzheimer's disease, Parkinson's disease and osteoporosis that are induced by age-related internal changes of the tissue, and the like. Type I diabetes, multiple sclerosis and rheumatoid arthritis induced by autoimmune diseases as well as burns and spinal injuries induced by wounds are also diseases characterized by tissue degeneration and tissue injury. As methods of treating such diseases resulting from tissue degeneration and injury, various regenerative medical techniques are being developed now.

Regenerative medicine is roughly divided into two methods: the induced regeneration method in which endogenous stem cells in patients are activated with a drug etc., and the cell replacement therapy in which stem cells or somatic cells induced from stem cells or tissues are transplanted. Specifically, in diseases accompanied by chronic inflammation and diseases in elderly individuals, the induced regeneration method does not work well due to reduced function of stem cells from the patient per se, and thus the development of the cell replacement therapy is imperative. In order to treat diseases resulting from tissue degeneration and injury by a cell replacement therapy, a large amount of stem cells or somatic cells induced from stem cells generally need to be prepared as materials for transplantation. For this purpose, stem cells that can differentiate into various tissues and that can self-replicate for a long time are indispensable for the development of a cell replacement therapy.

As stem cells that satisfy these conditions, there have been reported ES cells or EG cells that can be induced from fertilized eggs or primordial germ cells. However, in order to perform the cell replacement therapy safely and efficiently, it is necessary to prepare ES cells or EG cells comprising the genome of the patient per se that can circumvent the immunological rejection of transplanted cells.

As a method of preparing ES cells comprising the genome of the patient per se, a method of nuclear transplantation in which the nucleus of an egg is replaced with that of a somatic cell of the recipient has been investigated in animals such as mice. However, the success rate of nuclear transplantation is still low, and no success has been made in humans. Separately, there is a report on establishment of the iPS (induced pluripotent stem) cells having a property close to that of ES cells by introducing four genes of Oct3/4, Sox2, Klf4 and c-Myc into fibroblasts derived from mouse skin (Cell 126: 1-14, Aug. 25, 2006). However, the rate of iPS induction is low, and it has not been successful in humans.

DISCLOSURE OF THE INVENTION

Problems to be Solved by the Invention

Thus, it is an object of the present invention to establish human pluripotent stem cells from cells derived from a human postnatal tissue, said stem cells having properties close to that of ES cells and comprising the genome of the patient per se thereby circumventing immunological rejection of transplanted cells.

Means to Solve the Problems

The present inventors have found that human pluripotent stem cells can be induced by introducing three genes of Oct3/4, Sox2 and Klf4 or three genes of Oct3/4, Sox2 and Klf4 plus the c-Myc gene or a histone deacetylase (HDAC) inhibitor into undifferentiated stem cells present in a human postnatal tissue in which each gene of Tert, Nanog, Oct3/4 and Sox2 has not undergone epigenetic inactivation. Furthermore, we have discovered a method of efficiently inducing human pluripotent stem cells by introducing three genes of Oct3/4, Sox2 and Klf4 or three genes of Oct3/4, Sox2 and Klf4 plus the c-Myc gene or a histone deacetylase inhibitor into undifferentiated stem cells after the undifferentiated stem cells were amplified by a primary culture or a second subculture, or a subculture in a low density and low subculturing in a culture medium comprising a low-concentration serum.

Human postnatal tissues are preferably tissues immediately after birth (various tissues of neonates), umbilical cord tissues (the umbilical cord, cord blood), the amnion, the placenta etc., and more preferably various neonatal tissues and umbilical cord tissues. Post-natal tissues include tissues of various timings during the period from the birth of an individual to its death. The undifferentiated stem cells refer to stem cells in which at least four genes of Nanog, Oct3/4, Sox2 and Tert have not undergone epigenetic modification by heterochromatin formation due to DNA methylation or histone modification, among the primordial cells in the tissue of somatic stem cells established in vitro, such as mesenchymal stem cells (Science, 1999, Apr. 2; 284 (5411): 143-7) and MAPCs (multipotent adult progenitor cells) (Stem Cell Rev. 2005; 1(1): 53-9), and MIAMI (marrow-isolated adult multilineage inducible) cells (J. Cell Sci. 2004 Jun. 15; 117 (Pt 14): 2971-81).

ES cell-like pluripotent stem cells refer to cells having an in vitro long-term self-renewal ability and the pluripotency of differentiating into three germ layers, and said pluripotent stem cells may form teratoma when transplanted into a test animal such as mouse. The present invention is thought to provide a useful technique for the cell replacement therapy for the treatment of diseases resulting from tissue degeneration or injury.

After extensive and intensive investigation on methods of establishing ES cell-like pluripotent stem cells from human postnatal tissues, the present inventors have obtained the following three major findings:

(1) Among the cells derived from human postnatal tissues, cells that can be transformed into ES cell-like pluripotent stem cells by introducing four genes of Oct3/4, Sox2, Klf4 and c-Myc are undifferentiated stem cells in which each gene of Tert, Nanog, Oct3/4 and Sox2 has not undergone epigenetic inactivation;

(2) Undifferentiated stem cells in which each gene of Tert, Nanog, Oct3/4 and Sox2 has not undergone epigenetic inactivation are mostly present in postnatal tissues immediately after birth (various neonatal tissues), cord tissues (the umbilical cord, cord blood), the amnion, the placenta and the like; and (3) When cultured under a high-concentration serum or subcultured for a long time even under a low serum concentration, undifferentiated stem cells in which each gene of Tert, Nanog, Oct3/4 and Sox2 has not undergone epigenetic inactivation lose its property of being transformed into ES cell-like pluripotent stem cells by the introduction of four genes of Oct3/4, Sox2, Klf4 and c-Myc. By applying said findings, we have completed the present invention that establishes ES cell-like pluripotent stem cells efficiently from human tissue-derived cells.

Since the c-Myc gene has a risk of inducing cancer, we have then investigated its alternatives, and have found that by adding a histone deacetylase inhibitor in stead of the c-Myc gene to undifferentiated stem cells in mice, ES cell-like pluripotent stem cells can be induced from undifferentiated stem cells in which the Tert, Nanog, Oct3/4 and Sox2 genes have not undergone epigenetic inactivation present in postnatal tissues, and thus, it is expected that, in the case of humans as well, by adding a histone deacetylase inhibitor in stead of the c-Myc gene to undifferentiated stem cells in which the Tert, Nanog, Oct3/4 and Sox2 genes have not undergone epigenetic inactivation, they could be transformed into ES cell-like pluripotent stem cells.

Furthermore, it was found, in mice, that transformation into ES cell-like pluripotent stem cells can be effected by introducing only three genes of Oct3/4, Sox2 and Klf4 except the c-Myc gene to undifferentiated stem cells, and thus it is expected in the case of humans as well, by adding three genes of Oct3/4, Sox2 and Klf4 to undifferentiated stem cells in which the Tert, Nanog, Oct3/4 and Sox2 genes have not undergone epigenetic inactivation, transformation into ES cell-like pluripotent stem cells could be effected.

Thus, the present invention provides the following (1) to (35):

(1) A human pluripotent stem cell having an in vitro long-term self-renewal ability and the pluripotency of differentiating into ectoderm, mesoderm and endoderm, that was induced from an undifferentiated stem cell present in a human postnatal tissue in which each gene of Tert, Nanog, Oct3/4 and Sox2 has not undergone epigenetic inactivation.

(2) The human pluripotent stem cell according to the above (1) induced from an undifferentiated stem cell present in a human postnatal tissue, wherein said undifferentiated stem cell present in the human postnatal tissue was subjected to a primary culture or a second subculture, or a subculture in a low serum concentration.

(3) The human pluripotent stem cell according to the above (1) induced by the forced expression of each of three genes of Oct3/4, Sox2 and Klf4 in an undifferentiated stem cell present in a human postnatal tissue, wherein said undifferentiated stem cell present in the human postnatal tissue was subjected to a primary culture or a second subculture or to a subculture in a low serum concentration.

(4) The human pluripotent stem cell according to the above (1) induced by the forced expression of each of four genes of Oct3/4, Sox2, Klf4 and c-Myc in an undifferentiated stem cell present in a human postnatal tissue, wherein said undifferentiated stem cell present in the human postnatal tissue was subjected to a primary culture or a second subculture or to a subculture in a low serum concentration.

(5) The human pluripotent stem cell according to the above (1) induced by combining the forced expression of each of three genes of Oct3/4, Sox2 and Klf4 and a histone deacetylase inhibitor treatment in an undifferentiated stem cell present in a human postnatal tissue, wherein said undifferentiated stem cell present in the human postnatal tissue was subjected to a primary culture or a second subculture or to a subculture in a low serum concentration.

(6) The human pluripotent stem cell according to the above (1) induced by combining the forced expression of each of three genes of Oct3/4, Sox2 and Klf4 and a MS-275 treatment in an undifferentiated stem cell present in a human postnatal tissue, wherein said undifferentiated stem cell present in the human postnatal tissue was subjected to a primary culture or a second subculture or to a subculture in a low serum concentration.

(7) The human pluripotent stem cell according to any one of the above (2) to (6) wherein FGF-2 is further used in the culture of said undifferentiated stem cell.

(8) The human pluripotent stem cell according to any one of the above (2) to (6) wherein PDGF and FGF are further used in the culture of said undifferentiated stem cell.

(9) The human pluripotent stem cell according to any one of the above (2) to (8) wherein the culture of said undifferentiated stem cell is further conducted in a lower density.

(10) The human pluripotent stem cell according to any one of the above (1) to (9) wherein said human pluripotent stem cell is positive for Nanog.

(11) The human pluripotent stem cell according to any one of the above (1) to (10) wherein said human pluripotent stem cell is positive for alkaline phosphatase staining.

(12) The human pluripotent stem cell according to any one of the above (1) to (11) wherein said human pluripotent stem cell is positive for Tert.

(13) The human pluripotent stem cell according to any one of the above (1) to (12) wherein said human pluripotent stem cell comes to have teratoma-forming potential when it is transplanted into a test animal.

(14) The human pluripotent stem cell according to any one of the above (1) to (13) wherein said human postnatal tissue is a tissue immediately after birth.

(15) The human pluripotent stem cell according to any one of the above (1) to (13) wherein said human postnatal tissue is a tissue immediately after birth and is a tissue derived from a neonatal tissue or an umbilical cord tissue.

(16) The human pluripotent stem cell according to any one of the above (1) to (13) wherein said human postnatal tissue is a tissue immediately after birth and is a tissue derived from a neonatal skin or a blood vessel derived from the umbilical cord.

(17) The human pluripotent stem cell according to any one of the above (1) to (16) wherein said human pluripotent stem cell further has an in vitro potential of differentiating into a primordial germ cell.

(18) An undifferentiated stem cell present in a human postnatal tissue, in which each gene of Tert, Nanog, Oct3/4 and Sox2 has not undergone epigenetic inactivation and which can be induced into a human pluripotent stem cell having an in vitro long-term self-renewal ability and the pluripotency of differentiating into ectoderm, mesoderm and endoderm by the forced expression of each of three genes of Oct3/4, Sox2 and Klf4.

(19) An undifferentiated stem cell present in a human postnatal tissue, in which each gene of Tert, Nanog, Oct3/4 and Sox2 has not undergone epigenetic inactivation and which can be induced into a human pluripotent stem cell having an in vitro long-term self-renewal ability and the pluripotency of differentiating into ectoderm, mesoderm and endoderm by the forced expression of each of four genes of Oct3/4, Sox2, Klf4 and c-Myc.

(20) An undifferentiated stem cell present in a human postnatal tissue, in which each gene of Tert, Nanog, Oct3/4 and Sox2 has not undergone epigenetic inactivation and which can be induced into a human pluripotent stem cell having an in vitro long-term self-renewal ability and the pluripotency of differentiating into ectoderm, mesoderm and endoderm by combining the forced expression of each of three genes of Oct3/4, Sox2 and Klf4 and a histone deacetylase inhibitor treatment.

(21) An undifferentiated stem cell present in a human postnatal tissue, in which each gene of Tert, Nanog, Oct3/4 and Sox2 has not undergone epigenetic inactivation and which can be induced into a human pluripotent stem cell having an in vitro long-term self-renewal ability and the pluripotency of differentiating into ectoderm, mesoderm and endoderm by combining the forced expression of each of three genes of Oct3/4, Sox2 and Klf4 and a MS-275 treatment.

(22) The undifferentiated stem cell present in a human postnatal tissue according to any one of the above (18) to (21), wherein said human postnatal tissue is a tissue immediately after birth.

(23) The undifferentiated stem cell present in a human postnatal tissue according to any one of the above (18) to (21), wherein said human postnatal tissue is a tissue immediately after birth and is a tissue derived from a neonatal tissue or an umbilical cord tissue.

(24) The undifferentiated stem cell present in a human postnatal tissue according to any one of the above (18) to (21), wherein said human postnatal tissue is a tissue immediately after birth and is a tissue derived from a neonatal skin or a blood vessel of the umbilical cord.

(25) The undifferentiated stem cell present in a human postnatal tissue according to any one of the above (18) to (24), wherein said human pluripotent stem cell further has an in vitro potential of differentiating into a primordial germ cell.

(26) A method of inducing a human pluripotent stem cell wherein an undifferentiated stem cell present in a human postnatal tissue, in which each gene of Tert, Nanog, Oct3/4 and Sox2 has not undergone epigenetic inactivation, is subjected to a primary culture or a second subculture or to a third or fourth subculture in a low serum concentration at 0 to 5%, and then each of three genes of Oct3/4, Sox2 and Klf4 is subjected to forced expression.

(27) The method of inducing a human pluripotent stem cell according to the above (26), wherein each of four genes comprising each of three genes of Oct3/4, Sox2 and Klf4 plus c-Myc is subjected to forced expression.

(28) The method of inducing a human pluripotent stem cell according to the above (26), wherein the forced expression of each of three genes of Oct3/4, Sox2 and Klf4 is combined with a histone deacetylase inhibitor treatment.

(29) The method of inducing a human pluripotent stem cell according to the above (26), wherein the forced expression of each of three genes of Oct3/4, Sox2 and Klf4 is combined with a MS-275 treatment.

(30) The method of inducing a human pluripotent stem cell according to any one of the above (26) to (29), wherein said undifferentiated stem cell is cultured in the presence of FGF-2.

(31) The method of inducing a human pluripotent stem cell according to any one of the above (26) to (29), wherein said undifferentiated stem cell is cultured in the presence of PDGF and EGF

(32) The method of inducing a human pluripotent stem cell according to any one of the above (26) to (31), wherein said human postnatal tissue is a tissue immediately after birth.

(33) The method of inducing a human pluripotent stem cell according to any one of the above (26) to (31), wherein said human postnatal tissue is a tissue immediately after birth and is a tissue derived from a neonatal tissue or an umbilical cord tissue.

(34) The method of inducing a human pluripotent stem cell according to any one of the above (26) to (31), wherein said human postnatal tissue is a tissue immediately after birth and is a tissue derived from a neonatal skin or a blood vessel of the umbilical cord.

(35) A method of culturing a human pluripotent stem cell according to any one of the above (1) to (17) in a culture medium comprising an inhibitor of Rho associated kinase as an active ingredient.

(36) The human pluripotent stem cell according to anyone of the above (1) to (17) on which cell surface antigens SSEA-3, SSEA-4, TRA-1-60, TRA-1-81, CD9, CD24, and CD90 are expressed.

The undifferentiated stem cells of the present invention present in a human postnatal tissue refer to stem cells that have not undergone epigenetic modification by heterochromatin formation due to DNA methylation or histone modification of at least four genes of Nanog, Oct3/4, Sox2 and Tert among the primordial cells in the tissue of various somatic stem cells established in vitro, such as mesenchymal stem cells, MAPCs and MIAMI cells. When human pluripotent stem cells are induced from undifferentiated stem cells present in a human postnatal tissue, each gene of Tert, Nanog, Oct3/4 and Sox2 is activated (expressed).

Mesenchymal stem cells refer to those cells having the potential of differentiating into mesenchymal cells (bone, cartilage, fat) among the cells (interstitial cells) obtained as nonhematopoietic cells that are adherent to a plastic culture tray when tissues of bone marrow, fat, muscle, skin etc. are cultured in a culture medium containing a high-concentration serum (5% or more). Thus, mesenchymal stem cells are the cells obtained by the above culturing, and thus their properties are different from those of the undifferentiated cells (stem cells in which at least four genes of Nanog, Oct3/4, Sox2 and Tert have not undergone epigenetic modification by heterochromatin formation due to DNA methylation or histone modification, among the primordial cells in the tissue of somatic stem cells established in vitro, such as mesenchymal stem cells, MAPCs and MIAMI cells) immediately after isolation from human postnatal tissues.

However, even under the condition of culturing mesenchymal stem cells, MAPCs and MIAMI cells, a very small number of the undifferentiated cells can be maintained depending on the culture conditions of a small passage number or low-density culturing. As the human postnatal tissues of the present invention, there can be mentioned each tissue at various timings during the period from the birth of an individual to its death (bone marrow fluid, muscle, adipose tissue, peripheral blood, skin, skeletal muscle etc.) and tissues concomitant to birth such as cord tissues (umbilical cord, cord blood), the amnion, the placenta and the like, preferably there can be mentioned tissues (bone marrow fluid, muscle, adipose tissue, peripheral blood, skin, skeletal muscle etc.) immediately after birth such as various neonatal tissues, and more preferably there can be mentioned various neonatal tissues such as neonatal skin and cord tissues (umbilical cord, cord blood) such as tissues derived from cord-derived blood vessels.

Undifferentiated stem cells present in the human postnatal tissues of the present invention can be cultured for a certain period from a primary culture in a culture medium containing or not containing a low concentration serum (preferably 2% or less) and to which cell growth factors (PDGF, EGF, FGF-2 etc.) have been added or not added, and have properties different from those of mesenchymal stem cells that are characterized by a long time culturing in the serum (concentrations exceeding 5%).

As the above cell growth factors, there can be mentioned FGF-2, PDGF, EGF, IGF, insulin, TGFb-1, activin A, noggin, BDNF, NGF, NT-1, NT-2, NT-3 and the like, and the addition of FGF-2 alone or the addition of both PDGF and EGF is preferred. The above FGF-2 stands for basic fibroblast growth factor, PDGF stands for platelet-derived growth factor, EGF stands for epidermal growth factor, IGF stands for insulin-like growth factor, TGF β-1 stands for transforming growth factor β-1, BDNF stands for brain-derived neurotrophic factor, NGF stands for nerve growth factor, NT-1 stands for neurotrophin-1, NT-2 stands for neurotrophin-2, and NT-3 stands for neurotrophin-3.

The above primary culture represents immediately after isolation from a human, the primary culture cells subcultured once represent the second subculture, the primary culture cells subcultured twice represent the third subculture, and the primary culture cells subcultured three times represent the fourth subculture. Culturing for a certain period from the above primary culture generally means from the primary culture to the fourth subculture, preferably from the primary culture to the second subculture.

Human pluripotent stem cells induced from undifferentiated stem cells present in a human postnatal tissue in which the Tert, Nanog, Oct3/4 and Sox2 genes have not undergone epigenetic inactivation represent stem cells that have a long-term self-renewal ability under the condition for culturing human ES cells and an in vitro pluripotency of differentiating into ectoderm, mesoderm and endoderm under the condition for inducing in vitro differentiation of human ES cells, and the above human pluripotent stem cells may further have a potential of differentiating into primordial germ cells under the condition for inducing in vitro differentiation of human ES cells. Also human pluripotent stem cells of the present invention induced from undifferentiated stem cells present in a human postnatal tissue in which the Tert, Nanog, Oct3/4 and Sox2 genes have not undergone epigenetic inactivation may be stem cells that have an ability of forming teratoma when transplanted into a test animal such as mouse.

The low concentration serum encompassed by the present invention is generally serum at a concentration of 5% or less, preferably serum at a concentration of 2% or less, and the low density as used herein is a concentration of about 10% or less.

As the method of alkaline phosphatase staining, the following method may be mentioned. Thus, after removing the culture liquid from each well, the cells are fixed in a 10% formaldehyde solution at room temperature for 2 to 5 minutes, washed with a phosphate buffer etc., a solution of nitroblue tetrazolium chloride/5-bromo-4-chloro-3'-indolyl phosphate p-toluidine salt (hereinafter referred to as the NBT/BCIP solution), a chromogenic substrate of alkaline phosphatase, is added, and reacted at room temperature for 20-30 minutes.

The human pluripotent stem cells were expressed cell surface antigens SSEA-3, SSEA-4, TRA-1-60, TRA-1-81, CD9, CD24, and CD90, and ES cell marker genes Nanog, Oct3/4, TDGF1, Dnmt3b, GABRB3, GDF3, Zfp42, ALP, CD9, and Thy-1. The promoter regions of Nanog and Oct3/4 in the human pluripotent stem cells were demethylated compared to the parental fibroblasts. The human pluripotent stem cells carries at least a single copy of Oct3/4, Sox2, Klf4, and c-Myc transgene. The induced human pluripotent stem cells and the parental cells (undifferentiated stem cell present in a human postnatal tissue) had almost the same SNP genotype each other, and HLA type of the induced human pluripotent stem cell was completely identical to that of the parental cell (undifferentiated stem cell present in a human postnatal tissue).

A histone deacetylase inhibitor and MS-275 and a treatment method using them are as describe later:

The method of forced expression as used herein comprises a method for external expression in which a gene is expressed by introducing it with a vector etc. and a method for internal expression in which internal expression is promoted by the stimulation of a drug etc. Furthermore, forced expression as used herein also encompasses a method in which the genes of Oct3/4, Sox2, Klf4 and c-Myc are extracellularly expressed, and then the proteins produced of Oct3/4, Sox2, Klf4 and c-Myc are introduced directly into the cell using a method for introducing protein. As the method for introducing protein, there can be mentioned in case of a method that employs a commercially available carrier reagent (Chariot, BioPorter, GenomONE), the PTD (protein transduction domain) fusion protein method, the electroporation method, the microinjection method and the like. The external expression method in which each gene of Oct3/4, Sox2, Klf4 and c-Myc is introduced into a vector etc. for forced expression is as follows:

The present invention will now be explained in detail below.

1. A Method of Separating a Cell Fraction that Contains Undifferentiated Stem Cells from Human Postnatal Bone Marrow As a method of obtaining the undifferentiated stem cells of the present invention present in human postnatal tissue from human bone marrow, the following method may be mentioned.

In order to harvest a bone marrow fluid from human bone marrow, the donor is given a general anesthetic, then placed on a prone position, and from the posterior border of the ilium, a needle called the bone marrow collection needle is stuck directly into the skin to lead the needle through the iliac surface to the bone marrow, and the liquid of the bone marrow is aspirated with a syringe. In order to obtain undifferentiated stem cells from the bone marrow fluid, the mononuclear cell fraction separated by density centrifugation is collected. The collected cell fraction, as crude purified cells containing the undifferentiated stem cells, is cultured according to the method described in 6., and used for the induction of human pluripotent stem cells of the present invention.

2. A Method of Separating a Fraction that Contains Undifferentiated Stem Cells from Human Postnatal Skin As a method of obtaining the undifferentiated stem cells of the present invention present in human postnatal tissue from human skin, the following method may be mentioned.

From the back of a human knee or the buttock, a skin tissue containing the epidermis and the dermis is harvested. This skin tissue is immersed in 0.6% trypsin (manufactured by Invitrogen)/DMEM (Dulbecco's Modified Eagle's Medium)/F-12 (manufactured by Invitrogen)/1% antibiotics, antimycotics (manufactured by Invitrogen) with the inner side of the skin facing downward, and treated at 37° C. for 30 minutes.

After the skin tissue is turned over to scrub slightly the inner side with tweezers, the skin tissue is finely cut into about 1 mm² sections using scissors, which are then centrifuged at 1200 rpm and room temperature for 10 minutes. The supernatant is removed, and to the tissue precipitate is added 25 ml of 0.1% trypsin/DMEM/F-12/1% antibiotics, antimycotics, and stirred using a stirrer at 37° C. and 200-300 rpm for 40 minutes. After confirming the tissue precipitate was fully digested, 3 ml fetal bovine serum (FBS) (manufactured by JRH) is added, and filtered sequentially with gauze (Type I manufactured by PIP), a 100 μm nylon filter (manufactured by FALCON) and a 40 μm nylon filter (manufactured by FALCON). After centrifuging at 1200 rpm and room temperature for 10 minutes to remove the supernatant, DMEM/F-12/1% antibiotics, antimycotics is added to wash the precipitate, and then centrifuged at 1200 rpm and room temperature for 10 minutes. The cell faction thus obtained may be cultured according to the method described in 6. below as crude purified cells containing undifferentiated stem cells, and used for the induction of human pluripotent stem cells of the present invention.

3. A Method of Separating a Fraction that Contains Undifferentiated Stem Cells from a Human Postnatal Skeletal Muscle As a method of obtaining the undifferentiated stem cells of the present invention present in human postnatal tissue from human skeletal muscle, the following method may be mentioned.

After the epidermis and a connective tissue containing muscle such as a lateral head of biceps brachii muscle and a sartorius muscle of the leg is cut and the muscle is excised, it is sutured. The whole muscle obtained is minced with scissors or a scalpel, and then suspended in DMEM (high glucose) containing 0.06% collagenase type IA (manufactured by SIGMA) and 10% FBS, and incubated at 37° C. for 2 hours.

By centrifugation, cells are collected from the minced muscle, and suspended in DMEM (high glucose) containing 10% FBS. After passing the suspension through a microfilter with a pore size of 40 μm and then a microfilter with a pore size of 20 μm, the cell fraction obtained may be cultured according to the method described in 6. below as crude purified cells containing undifferentiated stem cells, and used for the induction of human pluripotent stem cells of the present invention.

4. A Method of Separating a Cell Fraction that Contains Undifferentiated Stem Cells from a Human Postnatal Adipose Tissue As a method of obtaining the undifferentiated stem cells of the present invention present in human postnatal tissue from human postnatal adipose tissue, the following method may be mentioned.

Cells derived from adipose tissue for use in the present invention may be isolated by various methods known to a person skilled in the art. For example, such a method is described in U.S. Pat. No. 6,153,432, which is incorporated herein in its entirety. A preferred source of adipose tissue is omental adipose tissue. In humans, adipose cells are typically isolated by fat aspiration.

In one method of isolating cells derived from adipose cells, adipose tissue is treated with 0.01% to 0.5%, preferably 0.04% to 0.2%, and most preferably about 0.1% collagenase, 0.01% to 0.5%, preferably 0.04%, and most preferably about 0.2% trypsin and/or 0.5 ng/ml to 10 ng/ml dispase, or an effective amount of hyaluronidase or DNase (DNA digesting enzyme), and about 0.01 to about 2.0 mM, preferably about 0.1 to about 1.0 mM, most preferably 0.53 mM concentration of ethylenediaminetetraacetic acid (EDTA) at 25 to 50° C., preferably 33 to 40° C., and most preferably 37° C. for 10 minutes to 3 hours, preferably 30 minutes to 1 hour, and most preferably 45 minutes.

Cells are passed through nylon or a cheese cloth mesh filter of 20 microns to 800 microns, more preferably 40 microns to 400 microns, and most preferably 70 microns. Then the cells in the culture medium are subjected to differential centrifugation directly or using Ficoll or Percoll or another particle gradient. The cells are centrifuged at 100 to 3000×g, more preferably 200 to 1500×g, most preferably 500×g for 1 minute to 1 hours, more preferably 2 to 15 minutes and most preferably 5 minutes, at 4 to 50° C., preferably 20 to 40° C. and more preferably about 25° C.

The adipose tissue-derived cell fraction thus obtained may be cultured according to the method described in 6. below as crude purified cells containing undifferentiated stem cells, and used for the induction of human pluripotent stem cells of the present invention.

5. A Method of Separating a Cell Fraction that Contains Undifferentiated Stem Cells from a Human Postnatal Peripheral Blood or Human Cord Blood As a method of obtaining the undifferentiated stem cells of the present invention present in human postnatal tissue from human postnatal peripheral blood or human cord blood, the following method may be mentioned.

First, from the vein or cord blood, about 50 ml to 500 ml of blood is harvested to collect cells, and mononuclear cells are collected by the Ficoll-Hypaque method [Kanof, M. E. and Smith, P. D. 1993 Isolation of whole mononuclear cells from peripheral blood. in Current Protocols in Immunology (J. E. Coligan, A. M. Kruisbeek, D. H. Margulies, E. M. Shevack, and W. Strober, eds.), pp. 7.1.1.-7.1.5, John Wiley & Sons, New York].

Then, about $1 \times 10^7$ to $1 \times 10^8$ human peripheral blood mononuclear cells are suspended in a RPMI 1640 medium (manufactured by Invitrogen) (hereinafter referred to as an essential medium for culturing peripheral blood stem cells) containing 10% fetal bovine serum (manufactured by JRH Biosciences), 100 μg/ml streptomycin and 100 units/ml penicillin (manufactured by Invitrogen), and after washing twice, the cells are recovered. The recovered cells are suspended again in the essential medium for culturing peripheral blood stem cells, which is then plated in a 100 mm plastic culture dish at $1 \times 10^7$ cells/dish, and incubated in a 37° C. incubator under a condition of 8% $CO_2$. After 10 hours, suspended cells are removed and the attached cells are only harvested by pipetting.

The peripheral blood-derived or cord blood-derived adherent cell fraction thus obtained may be cultured according to the method described in 6. below as crude purified cells containing undifferentiated stem cells, and used for the induction of human pluripotent stem cells of the present invention.

6. A Method of Culturing Undifferentiated Stem Cells Present in a Human Postnatal Tissue Examples of culture media useful in culturing the undifferentiated stem cells of the present invention present in a human postnatal tissue include the ES medium [40% Dulbecco's Modified Eagle's Medium (DMEM), 40% F12 medium, 2 mM L-glutamine, 1% non-essential amino acids, 0.1 mM β-mercaptoethanol (the above are manufactured by SIGMA), 20% Knockout Serum Replacement (manufactured by Invitrogen), 10 μg/ml gentamycin (manufactured by Invitrogen)] (hereinafter referred to as the ES medium), the MAPC medium [60% Dulbecco's Modified Eagle's Medium-low glucose (manufactured by Invitrogen), 40%

MCDB 201 (manufactured by Invitrogen), 1×ITS medium supplement (manufactured by SIGMA), 1× linolenic acid albumin (manufactured by SIGMA), 1 nM dexamethasone (manufactured by SIGMA), $10^{-4}$ M ascorbic acid (manufactured by SIGMA), 10 µg/ml gentamycin (manufactured by Invitrogen), 2% fetal bovine serum (manufactured by Invitrogen)] (hereinafter referred to as the MAPC medium), the FBM medium (manufactured by Lonza) [MCDB202 modified medium, 2% fetal bovine serum, 5 µg/ml insulin, 50 µg/ml gentamycin, 50 ng/ml amphotericin-B] (hereinafter referred to as the FBM medium), and the like.

As "growth factors, cytokines, hormones" to be added to the above culture medium, there can be mentioned FGF-2, PDGF, EGF, IGF, insulin, TGFb-1, activin A, Noggin, BDNF, NGF, NT-1, NT-2, NT-3 and the like.

In order to induce human pluripotent stem cells of the present invention efficiently form the undifferentiated stem cells of the present invention present in a human postnatal tissue, preferably the cell fraction obtained by the above methods 1. to 5. is cultured in a medium containing the above additives for about 1 to 12 days at a low density of about $10^3$ cells/cm$^2$ to $10^4$ cells/cm$^2$.

7. A Method of Inducing Human Pluripotent Stem Cells from Undifferentiated Stem Cells Present in a Human Postnatal Tissue In order to induce the human pluripotent stem cells of the present invention from the undifferentiated stem cells of the present invention present in a human postnatal tissue cultured according to the method described in 6., it is necessary to introduce the c-Myc gene or a histone deacetylase inhibitor, in addition to the three genes of Oct3/4, Sox2 and Klf4, to the undifferentiated stem cells of the present invention present in a human postnatal tissue cultured according to the method described in 6.

As virus vectors that can be used for introducing a gene into the undifferentiated stem cells of the present invention present in a human postnatal tissue, there can be mentioned retrovirus vectors (including lentivirus vectors), adenovirus vectors and the like, and preferably adenovirus vectors are used to introduce a mouse-derived cationic amino acid transporter (mCAT) gene, and then a retrovirus vector is used to introduce the Oct3/4, Sox2, Klf4 and c-Myc genes.

As virus vector plasmids, there can be mentioned pMXs, pMXs-IB, pMXs-puro, pMXs-neo (pMXs-IB is a vector carrying the blasticidin-resistant gene in stead of the puromycin-resistant gene of pMXs-puro) [Experimental Hematology, 2003, 31 (11): 1007-14], MFG [Proc. Natl. Acad. Sci. U.S.A. 92, 6733-6737 (1995)], pBabePuro [Nucleic Acids Research 18, 3587-3596 (1990)], LL-CG, CL-CG, CS-CG, CLG [Journal of Virology 72: 8150-8157 (1998)] and the like as the retrovirus system, and pAdex1 [Nucleic Acids Res. 23: 3816-3821 (1995)] and the like as the adenovirus system.

As packaging cells, any cells may be used that can supply a lacking protein of a recombinant virus vector plasmid deficient in at least one gene encoding a protein required for virus packaging. For example, there can be used HEK-293 cells derived from human kidney, packaging cells based on a mouse fibroblast NIH3T3, and the like.

As proteins to be supplied by packaging cells, there can be used retrovirus-derived proteins such as gag, pol, and env in the case of retrovirus vectors, HIV-derived proteins such as gag, pol, env, vpr, vpu, vif, tat, rev, and nef in the case of lentivirus vectors, and adenovirus-derived proteins such as E1A and E1B in the case of adenovirus vectors.

By introducing any of the above recombinant virus vector plasmid into the above packaging cells, recombinant virus vectors can be produced. As methods of introducing the above virus vector plasmid into the above packaging cells, various gene introduction methods are known including, but not limited to, the calcium phosphate method [Kokai (Japanese Unexamined Patent Publication) No. 2-227075], the lipofection method [Proc. Natl. Acad. Sci. U.S.A. 84: 7413 (1987)], the electroporation method and the like, and any suitable method may be used from the known gene introduction methods.

As histone acetylase inhibitors, there can be mentioned those described in the following A to E, and among them MS-275 is preferred.

A. Trichostatin A and its analogs, for example: trichostatin A (TSA); and trichostatin C (Koghe et al. 1998, Biochem. Pharmacol. 56: 1359-1364).

B. Peptides, for example: oxamflatin [(2E)-5-[3-[(phenylsulfonyl)aminophenyl]-pent-2-ene-4-inohydroxamic acid (Kim et al., Oncogene 18: 2461-2470 (1999)); Trapoxin A (cyclo-(L-phenylalanyl-L-phenylalanyl-D-pipecolinyl-L-2-amino-8-oxo-9,10-epoxy-decanoyl (Kijima et al., J. Biol. Chem. 268: 22429-22435 (1993)); FR901228, depsipeptide (Nakajima et al., Ex. Cell RES. 241: 126-133 (1998)); FR225497, cyclic tetrapeptide (H. Mori et al., PCT International Patent Publication WO 00/08048 (Feb. 17, 2000)); apicidin, cyclic tetrapeptide [cyclo-(N—O-methyl-L-tryptophanyl-L-isoleucinyl-D-pipecolinyl-L-2-amino-8-oxodecanoyl)] (Darkin-Rattray et al., Proc. Natl. Acad. Sci. U.S.A. 93: 13143-13147 (1996); apicidin Ia, apicidin Ib, apicidin Ic, apicidin IIa, and apicidin IIb (P. Dulski et al., PCT International Patent Publication WO 97/11366); HC-toxin, cyclic tetrapeptide (Bosch et al., Plant Cell 7: 1941-1950 (1995)); WF27082, cyclic tetrapeptide (PCT International Patent Publication WO 98/48825); and chlamydocin (Bosch et al., supra).

C. Hybrid polar compounds (HPC) based on hydroxamic acid, for example: salicyl hydroxamic acid (SBHA) (Andrews et al., International J. Parasitology 30: 761-8 (2000)); suberoylanilide hydroxamic acid (SAHA) (Richon et al., Proc. Natl. Acad. Sci. U.S.A. 95: 3003-7 (1998)); azelaic bishydroxamic acid (ABHA) (Andrews et al., supra); azelaic-1-hydroxamate-9-anilide (AAHA) (Qiu et al., Mol. Biol. Cell 11: 2069-83 (2000)); M-carboxy cinnamic acid bishydroxamide (CBHA) (Ricon et al., supra); 6-(3-chlorophenylureido) carpoic hydroxamic acid, 3-Cl-UCHA) (Richon et al., supra); MW2796 (Andrews et al., supra); and MW2996 (Andrews et al., supra).

D. Short chain fatty acid (SCFA) compounds, for example: sodium butyrate (Cousens et al., J. Biol. Chem. 254: 1716-23 (1979)); isovalerate (McBain et al., Biochem. Pharm. 53: 1357-68(1997)); valproic acid; valerate (McBain et al., supra); 4-phenyl butyric acid (4-PBA) (Lea and Tulsyan, Anticancer RESearch 15: 879-3 (1995)); phenyl butyric acid (PB) (Wang et al., Cancer RESearch 59: 2766-99 (1999)); propinate (McBain et al., supra); butylamide (Lea and Tulsyan, supra); isobutylamide (Lea and Tulsyan, supra); phenyl acetate (Lea and Tulsyan, supra); 3-bromopropionate (Lea and Tulsyan, supra); tributyrin (Guan et al., Cancer RESearch 60: 749-55 (2000)); arginine butyrate; isobutyl amide; and valproate.

E. Benzamide derivatives, for example: MS-275 [N-(2-aminophenyl)-4-[N-(pyridine-3-yl-methoxycarbonyl)aminomethyl]benzamide] (Saito et al., Proc. Natl. Acad. Sci. U.S.A. 96: 4592-7 (1999)); and a 3'-amino derivative of MS-275 (Saito et al., supra); and CI-994.

A histone deacetylase inhibitor treatment may be carried out, for example, as follows:

The concentration of the histone deacetylase inhibitor used depends on a particular inhibitor, but is preferably 0.001 nM to about 10 mM, and more preferably about 0.01 nM to about 1000 nM. The effective amount or the dosage of a histone deacetylase inhibitor is defined as the amount of the histone deacetylase inhibitor that does not significantly decrease the survival rate of cells, specifically undifferentiated stem cells. Cells are exposed for 1 to 5 days or 1 to 3 days. The exposure period may be less than one day. In a specific embodiment, cells are cultured for about 1 to 5 days, and then exposed to an effective amount of a histone deacetylase inhibitor. However, the histone deacetylase inhibitor may be added at the start of culturing. Within such a time frame, a gene-carrying vehicle such as a vector containing a nucleic acid encoding three genes (Oct3/4, Sox2 and Klf4) is introduced into cultured cells by a known method.

8. A Method of Culturing Human Pluripotent Stem Cells Induced from Undifferentiated Stem Cells Present in a Human Postnatal Tissue Examples of culture media useful for culturing human pluripotent stem cells induced from undifferentiated stem cells present in a human postnatal tissue of the present invention include, but not limited to, the ES medium, and a culture medium suitable for culturing human ES cells such as MEF-conditioned ES medium (hereinafter referred to as the MEF-conditioned ES medium) which is a supernatant obtained by adding 10 ng/ml FGF-2 to the ES medium and then mouse embryonic fibroblasts (hereinafter referred to as MEF) were added thereto and cultured for 24 hours to obtain the supernatant.

As "growth factors, cytokines, hormones" to be added to the above culture media, there can be mentioned ingredients involved in the growth and maintenance of human ES cells including FGF-2, TGFb-1, activin A, Nanoggin, BDNF, NGF, NT-1, NT-2, NT-3 and the like. The addition of Y-27632 (Calbiochem; water soluble) or Fasudil (HA1077: Calbiochem), an inhibitor of Rho associated kinase (Rho associated coiled coil-containing protein kinase) is also useful for culturing the human pluripotent stem cells of the present invention.

In order to culture and grow human pluripotent stem cells induced from the undifferentiated stem cells of the present invention present in a human postnatal tissue, it is preferred that the cells are subcultured every 5 to 7 days in a culture medium containing the above additives on a MEF-covered plastic culture dish or a matrigel-coated plastic culture dish to 1:3 to 1:6 or plated at $10^3$ cells/cm$^2$ to $3\times10^4$ cells/cm$^2$.

9. A Method of Storing Human Pluripotent Stem Cells Induced from Undifferentiated Stem Cells Present in a Human Postnatal Tissue for a Long Time In order to store human pluripotent stem cells induced from the undifferentiated stem cells of the present invention present in a human postnatal tissue for a long time, the following method may be mentioned.

After suspending the cells in the Cryopreservation Medium For Primate ES Cells (manufactured by Repro-CELL), they are rapidly frozen in liquid nitrogen, and stored in a liquid nitrogen storage vessel for a long time.

10. A Method of Treating Diseases Using Human Pluripotent Stem Cells Induced from Undifferentiated Stem Cells Present in a Human Postnatal Tissue In order to apply human pluripotent stem cells induced from the undifferentiated stem cells of the present invention present in a human postnatal tissue to treatment of diseases, the following method may be mentioned.

In order to apply human pluripotent stem cells induced from the undifferentiated stem cells of the present invention present in a human postnatal tissue to treatment of diseases caused by degeneration or insufficient functions of various tissues, it is desirable to harvest a tissue from an individual who wishes a future treatment, and to construct a cell bank system for storing stably undifferentiated stem cells present in a human postnatal tissue or the human pluripotent stem cells of the present invention induced from the undifferentiated stem cells.

Since undifferentiated stem cells present in a human postnatal tissue are detected at high rates in young individuals, preferred undifferentiated stem cells for the cell bank are cord blood, the umbilical cord, the placenta, skin obtained from neonates and the like. Even in adults, undifferentiated stem cells for the cell bank may be harvested from the bone marrow, adipose tissue, peripheral blood, skin and the like depending on the physical status of the donor. The undifferentiated stem cells of the present invention obtained from each donor may be stored frozen as they are, or may be transformed into human pluripotent stem cells according to the above-mentioned method of the present invention prior to storing frozen.

The undifferentiated stem cells of the present invention or the human pluripotent stem cells of the present invention thus stored may be used for the treatment of the donor per se or of immunohistologically compatible recipients as well. In treatment, depending on the amount of cell replacement required for the treatment of the subject disease, the human pluripotent stem cells of the present invention must be subcultured according to the method of the above 8. The required number of the human pluripotent stem cells of the present invention obtained by subculturing can be used for the treatment of various diseases by a method described below.

Diseases of the central nervous system using the human pluripotent stem cells of the present invention include Parkinson's disease, Alzheimer's disease, multiple sclerosis, cerebral infarction, spinal injury and the like. For the treatment of Parkinson's disease, a therapeutic method is possible in which human pluripotent stem cells are differentiated into dopamine-acting neurons and then transplanted into the striate body of the patient with Parkinson's disease. Differentiation into dopamine-acting neurons can be effected by coculturing the PA6 cell which is a mouse stromal cell line and the human pluripotent stem cells of the present invention under a serum-free condition. For the treatment of Alzheimer's disease, cerebral infarction and spinal injury, a therapeutic method in which the human pluripotent stem cells of the present invention are induced to differentiate into neural stem cells followed by transplantation into the injured site is effective.

In order to induce differentiation from the human pluripotent stem cells of the present invention to neural stem cells, three methods may be mentioned. In a first method, the human pluripotent stem cells of the present invention are cultured in suspension to form an embryoid body, and the embryoid body obtained is cultured in a serum-free medium containing FGF-2 for use in the culture of neural stem cells. In a second method, the human pluripotent stem cells of the present invention are cocultured with the PA6 cell which is a mouse stromal cell line, and then cultured in a serum-free medium containing FGF-2 for use in the culture of neural stem cells.

In a third method, the human pluripotent stem cells of the present invention are transferred to a serum-free medium containing FGF-2 to directly induce differentiation. In the treatment of multiple sclerosis, treatment can be effected by further inducing the differentiation of neural stem cells induced from the human pluripotent stem cells of the present invention into oligodendrocytes or progenitors of oligodendrocytes, which are then transplanted to the injured site. As a method of inducing oligodendrocytes or progenitors of oligodendrocytes from neural stem cells induced from the human pluripotent stem cells of the present invention, there can be mentioned a method of culturing said neural stem cells in the presence of a fusion protein between a soluble interleukin-6 receptor and interleukin-6.

The human pluripotent stem cells of the present invention can be used for the treatment of hepatic diseases such as hepatitis, cirrhosis and liver failure. In order to treat these diseases, the human pluripotent stem cells of the present invention are preferably differentiated to hepatic cells or hepatic stem cells, and then are transplanted. Hepatic cells or hepatic stem cells may be obtained by culturing the human pluripotent stem cells of the present invention in the presence of activin A for 5 days, and then culturing in the presence of the hepatocyte growth factor (HGF) for about a week to obtain hepatic cell or hepatic stem cells.

The human pluripotent stem cells of the present invention can be used for the treatment of pancreatic diseases such as type I diabetes mellitus. In the case of type I diabetes mellitus, the human pluripotent stem cells of the present invention are preferably differentiated to pancreatic beta cells, and then are transplanted to the pancreas. The human pluripotent stem cells of the present invention can be differentiated to pancreatic beta cells in following six steps of culturing: (1) culturing in the presence of a serum-free medium, activin A and Wnt protein for 1 to 2 days; (2) culturing in the presence of 0.2% FBS and activin A for 1 to 2 days; (3) culturing in the presence of 2% FBS, FGF-10 and KAAD-cyclopamine (keto-N-aminoethylaminocaproyl dihydrocinnamoylcyclopamine) for 2 to 4 days; (4) culturing in the presence of 1% B27 (manufactured by Invitrogen), FGF-10, KAAD-cyclopamine and retinoic acid for 2 to 4 days; (5) culturing in the presence of 1% B27, gamma secretase inhibitor and extendin-4 for 2 to 3 days; (6) culturing in the presence of 1% B27, extendin-4, IGF-1 and HGF for 3 days.

The human pluripotent stem cells of the present invention can be used for the treatment of heart failure associated with ischemic heart diseases. In treating heart failure, the human pluripotent stem cells of the present invention are preferably differentiated into cardiac muscle cells prior to transplanting to the injured site. By adding noggin to the medium from three days before forming an embryoid body, cardiac muscle cells can be obtained from the human pluripotent stem cells of the present invention in about 2 weeks after forming the embryoid body.

Effect of the Invention

The present invention provides for the first time human pluripotent stem cells induced from undifferentiated stem cells present in a human postnatal tissue and having an in vitro long-term self-renewal ability and the pluripotency of differentiating into ectoderm, mesoderm and endoderm, and further said human pluripotent stem cells may have a potential of differentiating into primordial germ cells.

Cells in a tissue that was lost in diseases etc. can be supplied by inducing human pluripotent cells from the undifferentiated stem cells harvested from a patient by using the induction method of the present invention, followed by inducing to differentiate into a necessary cell depending on diseases and then transplanting the cells to the patient. The undifferentiated stem cells of the present invention present in a human postnatal tissue can be used to search drugs that promote the induction from said undifferentiated stem cells to human pluripotent stem cells by using markers such as Tert, Nanog, Sox2, Oct3/4 and alkaline phosphatase that direct the induction to human pluripotent stem cells. Said drugs can be used in stead of gene introduction and can enhance the induction efficiency of human pluripotent stem cells.

In the figure, W1, W2, W3, W4, W5 and W6 represent the number of each well of the 6-well plate used in Example 12.

Figure 4:
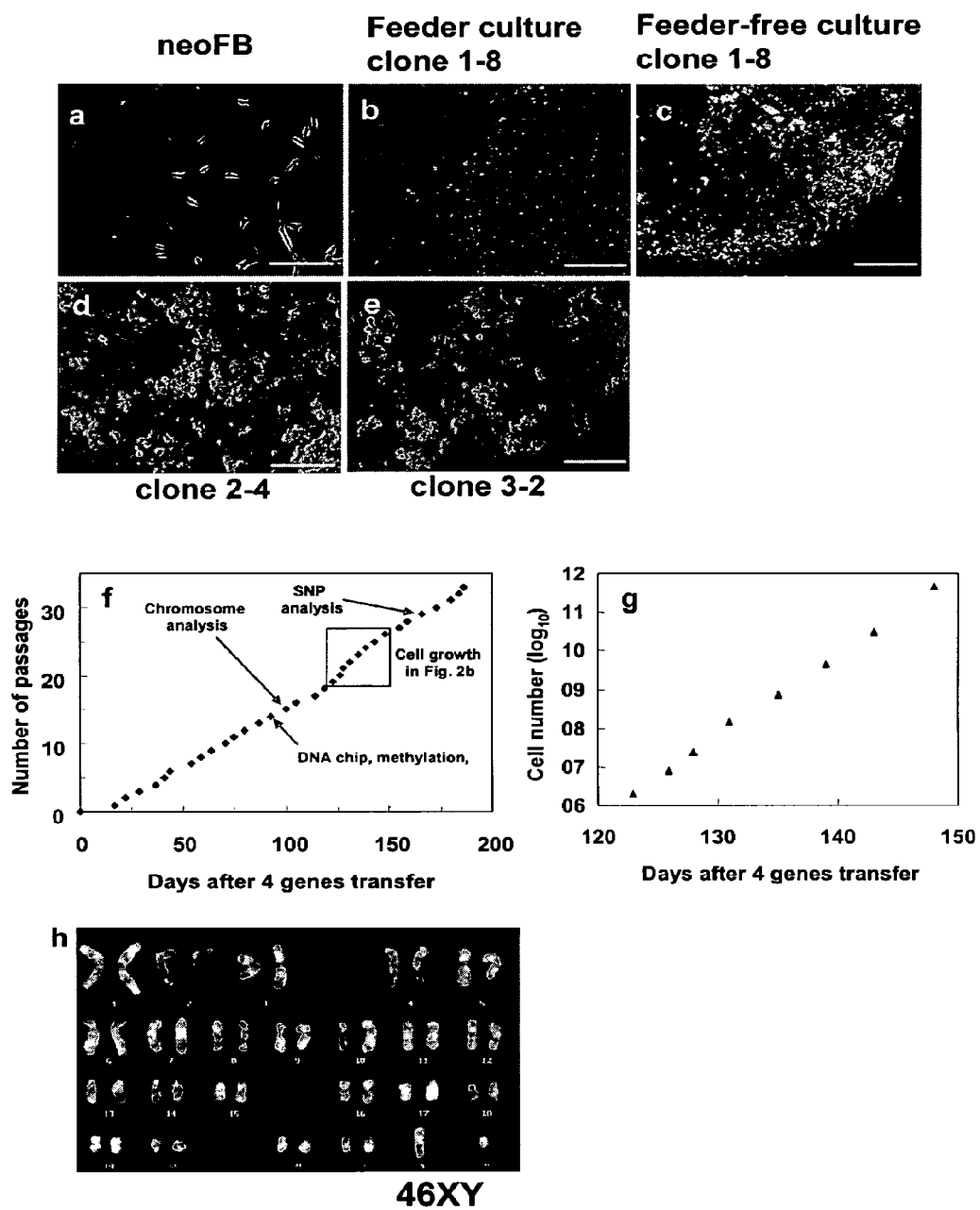

FIG. 4: Figure shows the characterization of human iPS clone 1-8. a-e, Morphology of its parental fibroblast (lot. 5F0438) (a), human iPS clone 1-8 cells cultured on MEF feeder cells (b), human iPS clone 1-8 cells in mTeSR1 medium (c), clone 2-4 cells (d), and clone 3-2 cells (e) in mTeSR1 medium. f-g, Growth curve of clone 1-8. Arrows indicate the dates of examinations. Square indicates the period for counting cell numbers to estimate cell proliferation rate. h, Multicolor karyogram image indicates normal karyotype of iPS clone 1-8 derived cell at day 101.

Figure 5:
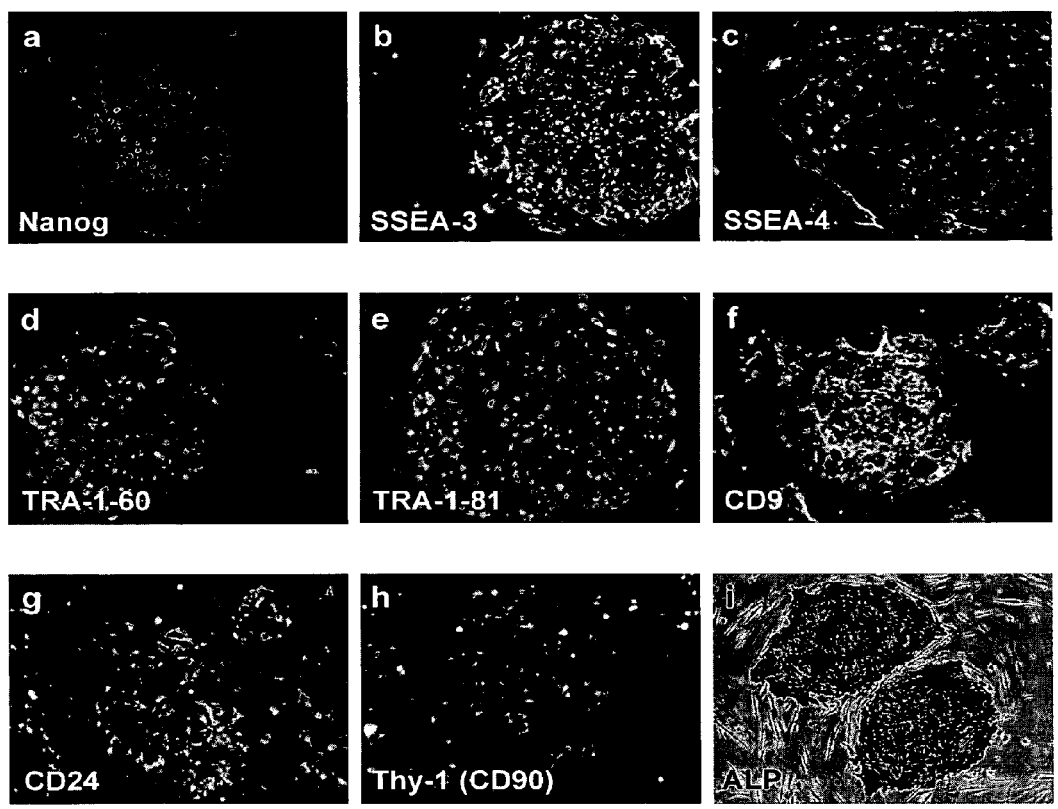

FIG. 5: Figure shows characterization of transcription factor, cell surface antigens and alkaline phosphatase activity in human iPS clone 1-8 cell. a-h, Immunohistochemical staining of human iPS cells (clone 1-8) with Nanog (a), SSEA-3 (b), SSEA-4 (c), TRA-1-60 (d), TRA-1-81 (e), CD9 (f), CD24 (g), Thy-1 (also called CD90) (h). Green fluorescent staining indicates that human iPS clone 1-8 expresses all of these surface antigens. i, Alkaline phosphatase staining indicates that iPS clone 1-8 is alkaline phosphatase positive.

Figure 6:
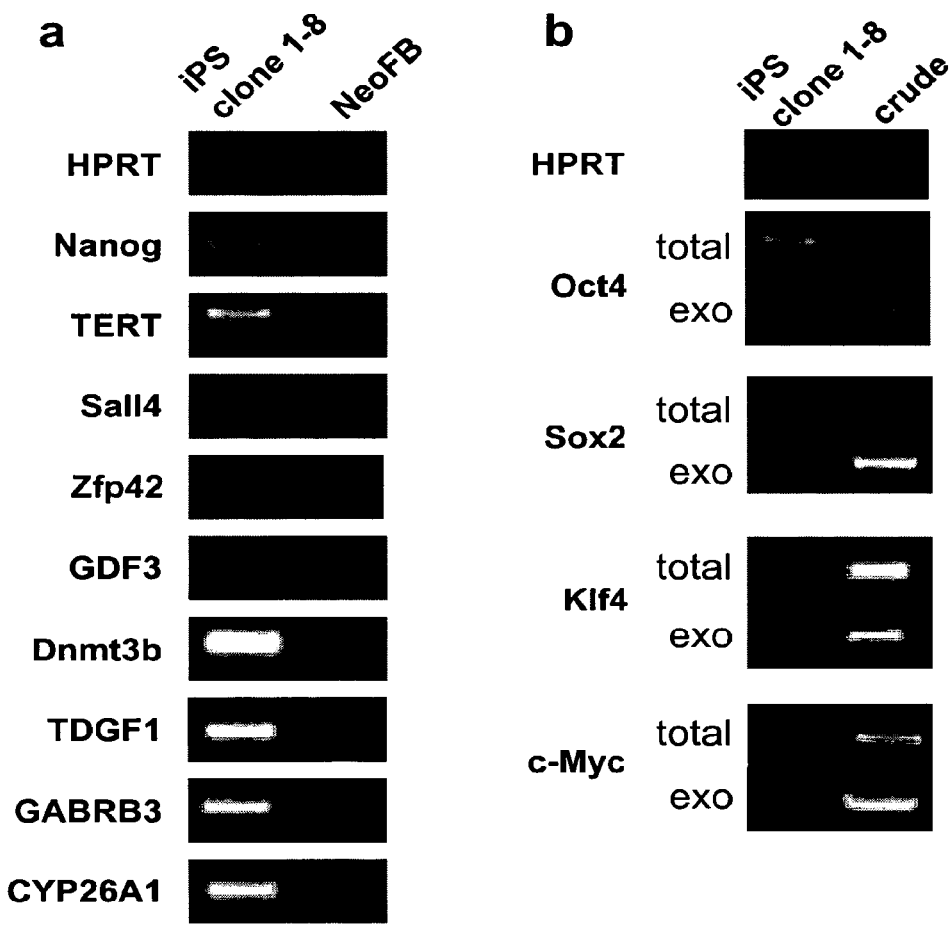

FIG. 6: Figure shows gene expression analysis of human iPS clone 1-8 cells. a, RT-PCR analysis of hES marker gene expression in clone 1-8 and its parental fibroblast (NeoFB). Genes were detected at 30 cycles except for CYP26A1 (35 cycles). b, Silencing of four transgenes in clone 1-8. Crude fibroblasts obtained on 17 days after gene transduction were used as control. "exo" primer sets selectively detected exogenous expression and "total" primer sets included endogenous expression.

Figure 7:
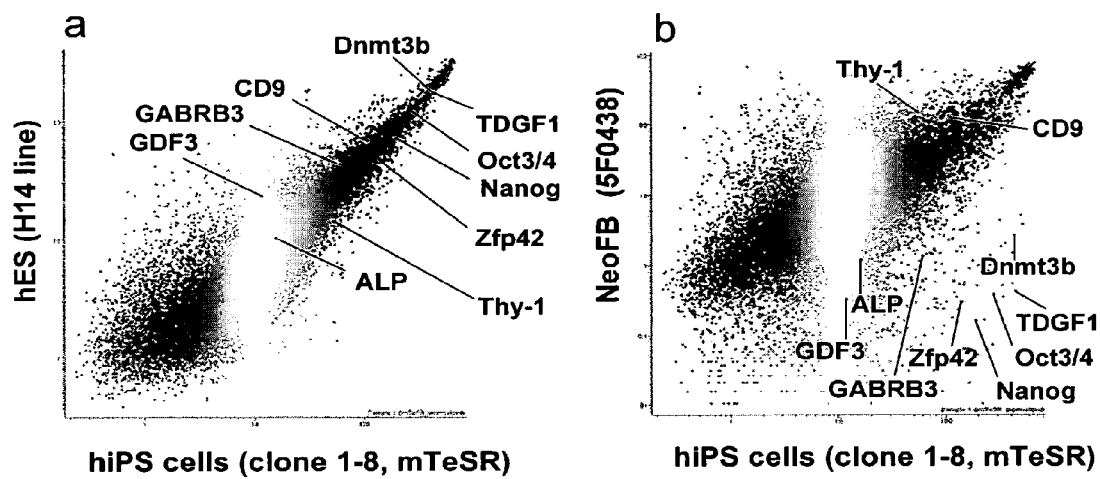

FIG. 7: Figure shows global gene expression analysis of human iPS clone1-8 cells. Scatter plots show comparison of global gene expression between human iPS clone-1-8 cells cultured in mTeSR and H14 hES cells with MEFs (GSM151741 from public database GEO) (a), or between clone 1-8 and its parental fibroblasts (b). Symbols of ES cell specific genes were pointed with lines in both scatter plots. Expression intensity was shown in colorimetric order from red (high) to green (low).

Figure 8:
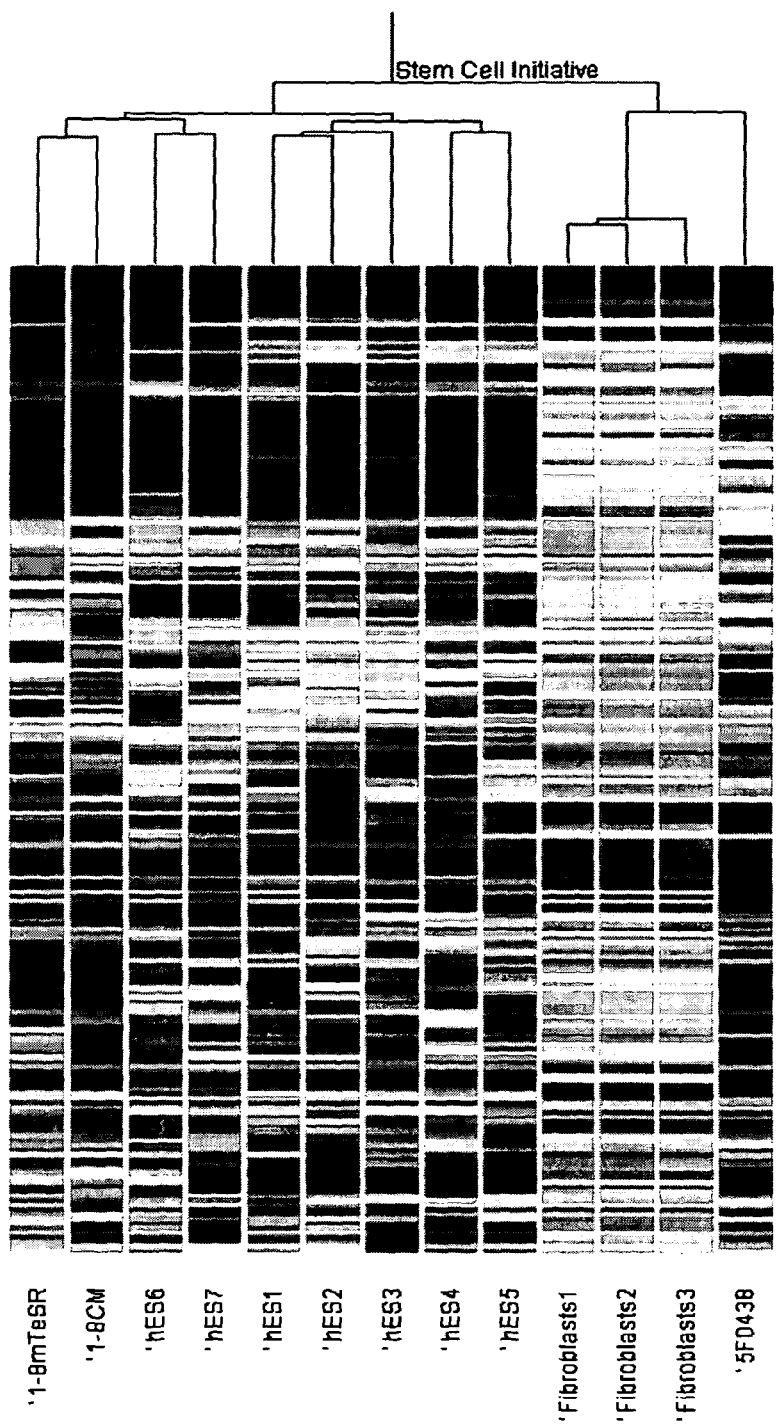

FIG. 8: Figure shows global gene expression analysis by gene trees. Cells were clustered in the gene tree based on a set of genes by the International Stem Cell Initiative (except PTF1A because of no array in the chip). Samples were designated 1-8 mTeSR for clone-1-8 cultured in mTeSR, 1-8CM for clone 1-8 cultured in MEF-conditioned medium, 5F0438 for the parental fibroblasts, hES1, hES2, hES3 (GSM194307, GSM194308, GSM194309) for Sheff 4 line cultured on MEF, hES4, hES5 (GSM194313, GSM194314) for Sheff 4 line cultured on matrigel, hES6, hES7 (GSM151739, GSM151741) for H14 line cultured on MEF, Fibroblasts1 for GSM96262, Fibroblasts2 for GSM96263, and Fibroblasts3 for GSM96264, respectively. Expression intensity was shown in colorimetric order from red (high) to green (low).

Figure 9:
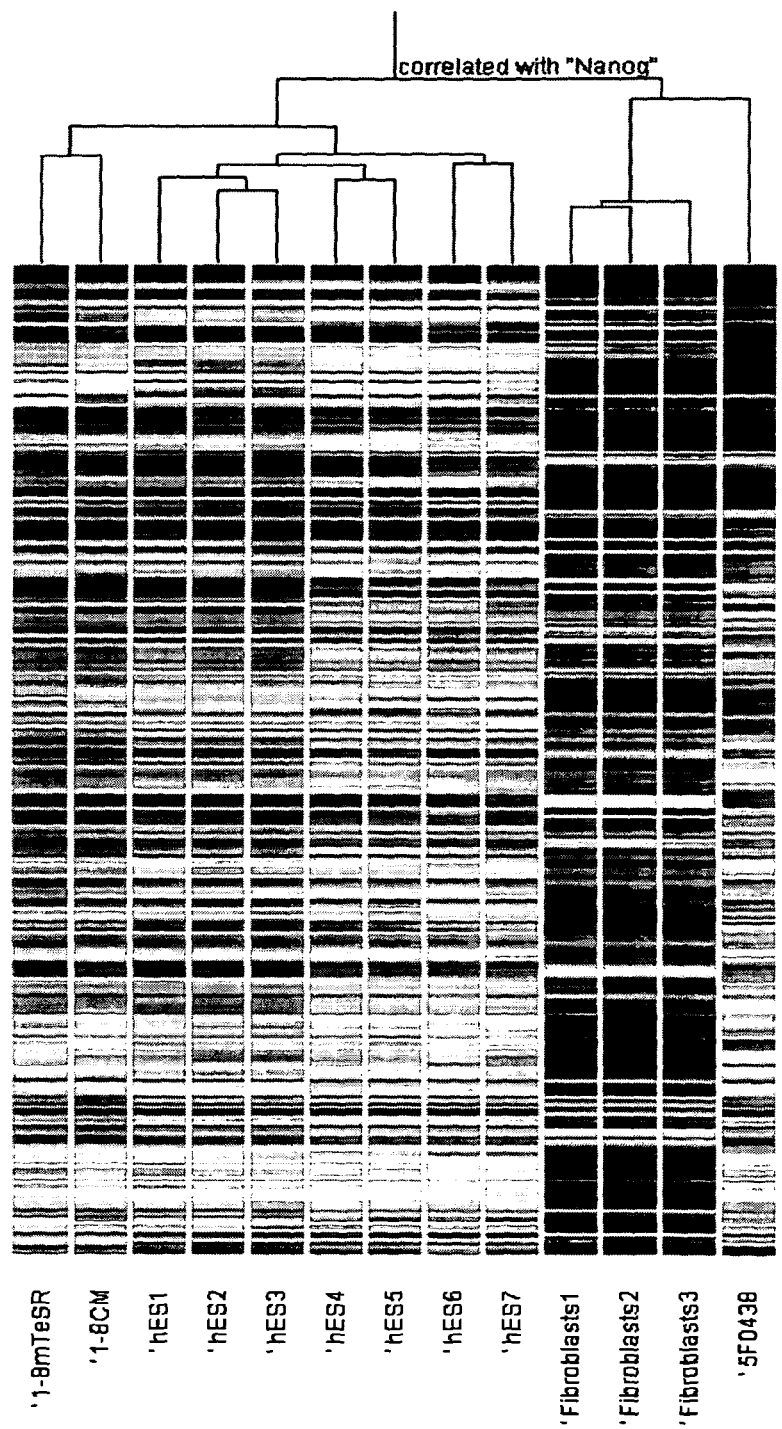

FIG. 9: Figure shows global gene expression analysis by gene trees. Cells were clustered in the gene tree based on a set of genes correlated with Nanog gene expression in human ES cells (seven GEO data) between the ratio of 0.99 and 1 when compared with fibroblasts (three GEO data). Samples were designated 1-8 mTeSR for clone-1-8 cultured in mTeSR, 1-8CM for clone 1-8 cultured in MEF-conditioned medium, 5F0438 for the parental fibroblasts, hES1, hES2, hES3 (GSM194307, GSM194308, GSM194309) for Sheff 4 line cultured on MEF, hES4, hES5 (GSM194313, GSM194314) for Sheff 4 line cultured on matrigel, hES6, hES7 (GSM151739, GSM151741) for H14 line cultured on MEF, Fibroblasts1 for GSM96262, Fibroblasts2 for GSM96263, and Fibroblasts3 for GSM96264, respectively. Expression intensity was shown in colorimetric order from red (high) to green (low).

FIG. 10: The parts of the Oct3/4 promoter including the distal enhancer (Oct3/4-Z1) and the proximal promoter region (Oct3/4-Z2) and the parts of the Nanog promoter including the proximal promoter region (Nanog-Z1, -Z2) were analyzed for the methylation of CpG (a). Ratio of methylation on CpG shown by circle is indicated by the percentage (b).

FIG. 11: Figure shows teratoma that was derived from human iPS-1-8 mTeSR cells cultured for 94 days. Human iPS-1-8 mTeSR cells were injected into SCID mouse testes and analyzed 56 days after injection. a, HE and alcian blue staining of formaldehyde fixed teratoma tissues. The teratomas contained tissues representative of the three germ layers. ne: neural epitherium, ca: cartilage, et: endodermal tract. b-d, tissues originated from transplant were distinguished from host tissues by HuNu staining. Nestin expressing neural epitherium (b), Collagen II expressing chondrocyte (c), alpha-fetoprotein expressing endodermal tract (d).

FIG. 12: Figure shows teratoma formation. Teratoma 1 (T-1) was derived from human iPS-1-8 mTeSR cells cultured for 94 days. The human iPS-1-8 mTeSR cells were injected into SCID mouse testes and analyzed 56 days after injection. Teratoma 2 (T-2) was derived from human iPS-1-8 mTeSR cells cultured for 102 days. The human iPS-1-8 mTeSR cells were injected into SCID mouse testes and analyzed 48 days after injection. In teratoma-1 (T-1), smooth muscle cells (positive for α-SMA) and secretary epithelium (positive for MUC-1) were observed in addition to three germ layers observed in FIG. 11.

FIG. 13: Figure shows teratoma formation. Teratoma 3 (T3) was derived from human iPS-1-8 mTeSR cells cultured for 114 days. Human iPS-1-8 mTeSR cells were injected into SCID mouse testis and analyzed 42 days after injection. Three germ layers similar to FIGS. 11 and 12 were observed. T-F1 and F2 figure shows teratoma that were derived from freeze-thawed iPS-1-8 mTeSR cells cultured for 134 days (passage 19). Human iPS-1-8 mTeSR cells were injected into SCID mouse testes and analyzed 46 days (T-F1) and 48 days (T-F2) after injection. Tissues consisting of three germ layers were observed. Melanocytes were also observed in T-F2 experiment. Pluripotency were maintained even via freezing and thawing.

FIG. 14: Figure shows the existence of four transgenes in human iPS clone 1-8. Oct3/4, Sox2, and Klf4 transgenes were detected by Southern blot analysis. Human iPS clone-1-8 was estimated to have approximately ten copies of both Oct3/4 transgenes and Sox2 transgenes, and a single copy of Klf4 transgene. Genomic PCR proved c-Myc transduction. Primer set was designed to include whole second intron. Black arrows indicate the position of transgene. White arrow indicates the position of endogenous c-Myc.

FIG. 15: Figure shows hES maker gene expression profile in ALP positive colonies induced by four genes (Oct4, Sox2, Klf4 and c-Myc). Colonies were stained for alkaline phosphatase at 17 days post 4 genes transduction. All ALP(+) colonies were dissected and determined their hES marker gene expressions. a, the number of colonies expressing Nanog, TDGF1, Dnmt3b, Zfp42, FoxD3, TERT, CYP26A1, and GDF3. b, morphologies of octa-positive colonies. c-d, the number of hES cell marker genes categorized by individual experiments.

FIG. 16-FIG. 22: Figure shows morphologies of four gene (Oct4, Sox2, Klf4 and c-Myc) induced colonies categorized by gene expression profile of ES cell related 8 genes (Nanog, TDGF1, Dnmt3b, Zfp42, FoxD3, TERT, CYP26A1, and GDF3) as well as alkaline phosphatase activity. Circles indicate the picked-up colony.

BEST MODE FOR CARRYING OUT THE INVENTION

Undifferentiated stem cells present in a human postnatal tissues are undifferentiated stem cells which are present in human postnatal skin, bone marrow, adipose tissue, skeletal muscle tissue, and peripheral blood, and tissues concomitant to birth such as placenta, umbilical cord and cord blood and in which the Tert, Nanog, Oct3/4 and Sox2 genes have not undergone epigenetic inactivation, and, by using a combination of induced expression of the three genes of Oct3/4, Sox2 and Klf4 and the induced expression of c-Myc or the addition of a histone deacetylase inhibitor, can induce human pluripotent stem cells having a long-term self-renewal ability and the pluripotency of differentiating into ectoderm, mesoderm and endoderm. The above human pluripotent stem cells may further have a potential of differentiating into primordial germ cells.

Undifferentiated stem cells present in a human postnatal tissue can be cultured using a plastic culture dish. When a 2% serum is used, PDGF and EGF or FGF-2 may be added to the culture medium, to which IGF or insulin may further be added. In this case, when a culture medium containing serum is used for a long term culture, properties of undifferentiated stem cells present in a human postnatal tissue may change, and thus it is important to limit the serum concentration to 2% or less and the number of passages to about twice. When a 2% low concentration serum is used, the MAPC medium or the FBM medium, for example, is used as the culture medium. As the culture condition, an incubator at 37° C. and 5% $CO_2$ is used similarly to common culture cells. It is also possible to use low concentration oxygen, for example a 3% oxygen concentration. Culture plates are preferably coated with fibronectin etc.

The human pluripotent stem cells of the present invention induced from undifferentiated stem cells present in a human postnatal tissue may be cultured using a plastic culture dish. In the primary culture, cells after the four genes of Oct3/4, Sox2, Klf4 and c-Myc were introduced therein are cultured in a MEF-conditioned human ES cell medium to which 10 ng/ml bFGF and 10 ng/ml activin A had been added, and the medium is changed every 1 to 2 days. The pluripotent stem cells induced are detached with dispase, collagenase, trypsin or the like, and subcultured. When MEF is used as a supporting layer after the primary culture, the induced human pluripotent stem cells are plated on a MEF-covered plastic culture dish, and cultured in a human ES cell medium supplemented with 10 ng/ml bFGF. When the supporting cells are not used, the induced human pluripotent stem cells are plated on a matrigel-coated plastic culture dish, and cultured in a MEF-conditioned human ES cell medium supplemented with 10 ng/ml bFGF and 10 ng/ml activin A. In either of the culture methods, the medium is changed every 1 to 2 days.

In order to induce the human pluripotent stem cells of the present invention from undifferentiated stem cells present in a human postnatal tissue in which each gene of Tert, Nanog, Oct3/4 and Sox2 has not undergone epigenetic inactivation, the following method may be used. First, an adenovirus vector is constructed carrying cDNA having the sequence of coding region of the mouse-derived cationic amino acid transporter (mCAT) gene (see Example 2, Table 1), which is then introduced into the packaging cell based on the HEK293 cell to prepare a virus solution of the adenovirus vector. The virus solution is added at a multiplicity of infection (m.o.i.: the ratio of the number of virus particles to the number of cells) of 1 to 20 to undifferentiated stem cells present in a human postnatal tissue in which each gene of Tert, Nanog, Oct3/4 and Sox2 has not undergone epigenetic inactivation, and thus undifferentiated stem cells expressing mCAT are prepared.

Then, a retrovirus vector carrying cDNA encoding human Oct3/4, a retrovirus vector carrying cDNA encoding human Sox2, a retrovirus vector carrying cDNA encoding human Klf4, and a retrovirus vector carrying cDNA encoding human c-Myc are constructed (Table 1), and then each of them is introduced into the packaging cell capable of producing an ecotropic recombinant virus constructed based on the HEK293 cell to prepare a virus solution of retrovirus vectors.

To the undifferentiated stem cells in which mCAT has been expressed using an adenovirus vector and in which each of the Tert, Nanog, Oct3/4 and Sox2 genes has not undergone epigenetic inactivation, four types of retrovirus vectors each carrying the four genes (coding regions) of Oct3/4, Sox2, Klf4 and c-Myc, respectively, are added at a m.o.i. of 1 to 200 per virus vector to establish the induction of the human pluripotent stem cells of the present invention.

To the undifferentiated stem cells in which mCAT has been expressed using an adenovirus vector and in which each of the Tert, Nanog, Oct3/4 and Sox2 genes has not undergone epigenetic inactivation, three types of virus vectors each carrying the genes (coding regions) of Oct3/4, Sox2 and Klf4, respectively, at a m.o.i. of 1 to 200 per virus vector, as well as MS-275 at a final concentration of 10 nM to 100 µM, preferably 100 nM to 1 µM, are added to establish the induction of the human pluripotent stem cells of the present invention.

It is preferred that the human pluripotent stem cells of the present invention after being suspended in the Cryopreservation Medium For Primate ES Cells (manufactured by ReproCELL), preferably are rapidly frozen in liquid nitrogen, and stored in a liquid nitrogen storage vessel.

It is preferred that the pluripotent stem cells of the present invention that were stored frozen are rapidly thawed by suspending in a medium that had been warmed to 37° C., removing the medium from the suspension by centrifugation, and then suspending again in a fresh medium to start culturing.

The following explains a method in which, by applying the present invention, siRNA and a compound that inhibit the induction from undifferentiated stem cells present in a human postnatal tissue in which the Tert, Nanog, Oct3/4 and Sox2 genes have not undergone epigenetic inactivation to human pluripotent stem cells are searched using a high throughput screening system.

siRNA represents a double stranded RNA that comprises about 19 base pairs which is part of the sequence of a gene, and that has an effect of inhibiting the translation of the gene to the protein due to RNA interference. When siRNA of a gene is introduced into a cell, only the function carried by the protein can be specifically deleted. Thus, by using a whole genome siRNA library in a specific cell, the state in which the function of only one gene among all the genes was deleted can be observed individually for every gene.

Thus, by using the above siRNA library, it is possible to identify a gene that inhibits the induction from a undifferentiated stem cell present in a human postnatal tissue in which the Tert, Nanog, Oct3/4 and Sox2 genes have not undergone epigenetic inactivation to a human pluripotent stem cell. By developing an inhibitor of the gene using this method, it is possible to induce human pluripotent stem cells from undifferentiated stem cells present in a human postnatal tissue.

As the siRNA library, those in which four siRNA's are synthesized for each gene of a total of about 25,000 human genes, mixed in equal amounts, and dispensed in a 384-well culture plate are used, and subjected to screening (manufactured by Qiagen). Details of it are as follows. Four siRNA's synthesized for each gene are mixed in equal amounts, and 2.5 pmol each is dispensed in each well of a 384-well culture plate. In order to cover all of about 25,000 genes, seventy three 384-well culture plates are needed. To predetermined wells of each plate, 2.5 pmol each of the positive and negative control siRNAs is dispensed in order to determine the introduction efficiency of siRNA into the cell and to correct for efficiency of each plate. The final concentration of siRNA is 50 nM.

After siRNA was prepared, a primary screening is conducted. As methods of detecting the activation of genes that could be an index for differentiation into the pluripotent stem cells of the present invention such as Tert, Nanog, Oct3/4 and Sox2 in the cell to be targeted, there are the promoter reporter assay of the gene of interest [as the reporter gene, EGFP (enhanced green fluorescence protein), luciferase etc.], the immunocytochemical staining method to said gene product, and the like.

For transfection of siRNA to the cell, the lipofection method may be used. To each well of a total of 73 plates in which siRNA has been dispensed, 0.1 µl of LipofectAMINE RNAiMax (manufactured by Invitrogen) in 10 µl of Opti-MEM (manufactured by Invitrogen) is dispensed. Ten minutes later, target cells prepared at 20 to 25 cells/µl in up to 40 µl of the medium are dispended to every well on the 73 plates to introduce siRNA into the cell. The number of cells and the amount of the medium are determined as appropriate depending on the cell used for screening.

In conducting a reporter assay, cells in which a reporter system has been permanently integrated with a retrovirus vector (including lentivirus) or cells 1 to 7 days after infection with an adenovirus vector carrying the reporter system of interest are used for cells such as adult stem cells for which gene introduction by the lipofection method or the calcium phosphate method is difficult. When the reporter system of the present invention is applied to cultured lined cells such as HEK293 cells and Hela cells, the reporter system should be introduced one day in advance or simultaneously with siRNA by a gene introduction method suitable for respective cells.

The entire 73 plates to which transfection reagents and cells have been dispensed are cultured in a culturing equipment maintained at 37° C. and 5% $CO_2$ for 2 to 7 days. The culturing time may vary as appropriate depending on the type of the cell, the gene to be detected, and the like.

As a method of selecting siRNA that promotes the induction from undifferentiated stem cells present in a human postnatal tissue to human pluripotent stem cells, alkaline phosphatase staining can be used. As the alkaline phosphatase staining method, the following method can be mentioned. After removing the culture liquid from each well, cells are fixed in a 10% formaldehyde solution at room temperature for 2 to 5 minutes, washed with a phosphate buffer etc., and a chromogenic substrate of alkaline phosphatase, nitroblue tetrazolium chloride/5-bromo-4-chloro-3'-indolyl phosphate para-toluidine salt solution (hereinafter referred to as the NBT/BLIP solution) is added and reacted at room temperature for 20 to 30 minutes.

Also when a compound library is used, the method used is conducted similarly to the above screening used for siRNA. The compound in stead of siRNA is spotted in each well, the cell is dispensed and cultured, and similarly determined. The transfection procedure is not necessary.

EXAMPLES

Example 1. Preparation of Retrovirus Vector

The retrovirus vector plasmids for the four genes of Oct3/4-pMx, Sox2-pMx, Klf4-pMx and c-Myc-pMx constructed as in Table 1 were introduced into the packaging cell, the Plat-E cell [Experimental Hematology, 2003, 31 (11): 1007-14], using Fugene HD (manufactured by Roche). During 24 to 48 hours after retrovirus vector introduction, the medium was replaced with a medium suitable for the cell to which gene is to be introduced. After culturing the Plat-E cell to which retrovirus vector was introduced for more than 4 hours, the supernatant was recovered and passed through a filter of 45 µm in diameter (manufactured by Millipore). By the above procedure, the retrovirus vector solutions of the four genes (Oct3/4, Sox2, Klf4 and c-Myc) were prepared.

The retrovirus vector plasmids for the three genes of Oct3/4-pMx, Sox2-pMx, Klf4-pMx and c-Myc-pMx were introduced into the packaging cell, the Plat-E cell, using Fugene HD (manufactured by Roche). During 24 to 48 hours after retrovirus vector introduction, the medium was replaced with a medium suitable for the cell to which gene is to be introduced. After culturing the Plat-E cell to which retrovirus vector was introduced for more than 4 hours, the supernatant was recovered and passed through a filter of 45 µm in diameter (manufactured by Millipore). By the above procedure, the retrovirus vector solution of the three genes (Oct3/4, Sox2 and Klf4) were prepared.

Example 2. Preparation of Adenovirus Vector

According to the present invention, it was necessary to introduce genes including an oncogene (c-Myc) into human cells by retrovirus vector in order to induce pluripotent stem cells. In this case, when a gene is introduced into human cells using an amphotropic retrovirus vector which can infect into human cells, there is a risk of infection to human cells other than the cells of interest. Thus, in preparation for safe experiment, an ecotropic retrovirus vector that infect the rodent cells but not human cells and an adenovirus vector carrying gene encoding its receptor which is mouse-derived cationic amino acid transporter 1 (mCAT1) were combined and used in gene introduction into the human cells.

First, an adenovirus vector carrying cDNA having the sequence of coding region of the mouse-derived cationic amino acid transporter (mCAT1) gene was constructed. Specifically, Adeno-X Expression System 1 kit (manufactured by TakaraBio Clontech) was used. In Adeno-X Expression System 1 kit, based on the experimental method attached to the kit by TakaraBio, the mCAT1 gene was subcloned into the multi-cloning site of a vector called pShuttle.

Subsequently, an expression cassette was excised by the PI-Sce I site and the I-Ceu I site, cleavage sites on both ends of the expression cassette of pShuttle, and a DNA fragment containing the desired gene was inserted in between the PI-Sce I site and the I-Ceu I site in the Adeno-X Viral DNA in the above kit, which was then treated with a restriction enzyme Swa I to remove adenovirus DNA for which integration was unsuccessful. After the plasmid was transformed into an *E. coli* DH5 strain, whether the desired gene was correctly introduced into adenovirus DNA or not was confirmed by restriction enzyme treatment, PCR etc. The plasmid was prepared in large quantities, and cleaved with the Pac I restriction enzyme. Using the recombinant adenovirus DNA thus obtained, the gene was introduced into the HEK293 cells (MicroBix) plated in six wells using Lipofectamin 2000 (manufactured by Invitrogen), and two weeks later when the cell exhibited a cytopathic effect (CPE), the cells were collected as they are in the medium.

Subsequently, after the cell suspension was subjected to freezing and thawing for three times, the cells were disrupted, and virus particles present in the cells were allowed to release into the liquid. The virus suspension thus prepared was added to one 100 mm plastic culture dish equivalent of HEK293 cells ($5 \times 10^6$ cells) to infect the cells, the virus was propagated. Furthermore, after virus was prepared in large quantities using four 150 mm plate equivalent of HEK293 cells, virus was purified using the Adenovirus Purification kit (manufactured by Clontech), and stored frozen at $-80°$ C.

The titer (plaque forming units, PFU) of the mCAT1 adenovirus vector was determined using the Adeno-X Rapid Titer kit. On a 24-well plate, HEK293 low cells were plated at a concentration of $5 \times 10^4$ cells/500 µl per well. Fifty µl of serially diluted (from $10^{-2}$ to $10^{-7}$) virus vector was mixed with 500 µl of the medium, and then used to infect the cells. After culturing at 5% $CO_2$ and 37° C. for 48 hours, the medium was aspirated off, the cells were dried for 5 minutes, and then using 500 µl of cold 100% methanol the cells were fixed by allowing to stand at $-20°$ C. for 10 minutes. After aspirating off methanol, the wells were washed three times with 500 µl of phosphate buffer containing 1% bovine serum albumin. A mouse anti-Hexon antibody was diluted 1000-fold with phosphate buffer containing 1% bovine serum albumin, and 250 µl each of it was added to wells.

After allowing to stand at 37° C. for 1 hour, the antibody solution was removed, and the wells were washed three times with 500 µl of phosphate buffer containing 1% bovine serum albumin. Horseradish peroxidase-labelled rat anti-mouse immunoglobulin antibody was diluted 500-fold with phosphate buffer containing 1% bovine serum albumin, and 250 µl was added to wells. After allowing to stand at 37° C. for 1 hour, the antibody solution was removed, and washed three times with 500 µl of phosphate buffer containing 1% bovine serum albumin. 250 µl of the DAB (diaminobenzidine) solution (10-fold DAB concentrate was diluted with a stable peroxidase buffer) was added to wells, and was allowed to stand at room temperature for 10 minutes. After aspirating off DAB, 500 µl of phosphate buffer was added. Using a 20× objective lens, the number of brown positive cells in six viewing fields was counted.

Radius of a standard 20× objective lens: 0.5 mm
Area in one viewing field: $7.853 \times 10^{-3}$ cm$^2$
Area of a well: 2 cm$^2$
Viewing field of a well: 2 cm$^2$/$7.853 \times 10^3$ cm$^2$=254.7 viewing fields $(32/6) \times 254.7/(0.55 \times 10^{-5}) = 2.5 \times 10^8$ ifu (infection unit)/ml

Example 3. Alkaline Phosphatase Staining

Staining for confirming alkaline phosphatase activity which is a characteristic of pluripotent stem cells was conducted in the following manner. After removing the culture medium, a 10% formalin neutral buffer solution was added to wells, and cells were fixed at room temperature for 5 minutes. After washing with a phosphate buffer etc., a chromogenic substrate of alkaline phosphatase, 1 step NBT/BCIP (manufactured by Pierce) was added and reacted at room temperature for 20 to 30 minutes. Cells having alkaline phosphatase activity were all stained blue violet.

Example 4. Determination Gene Expression of a Colony by Quantitative PCR

The expression of target gene of each colony including an alkaline phosphatase-positive colonies was determined using quantitative PCR in the following manner. Colonies developed by the induction of pluripotent stem cells were harvested, and RNA was extracted using the Recoverall total nucleic acid isolation kit for FFPE (manufactured by Ambion). After synthesizing cDNA from the extracted RNA, the target gene was amplified using the Taqman Preamp mastermix (manufactured by Applied Biosystems).

As the primers for quantitative PCR, the Taqman gene exprESsion assay (manufactured by Applied Biosystems) was used. The following shows the name of the target gene and the product code of each primer. Human Hprt: Hs99999909_m1, human Nanog: Hs02387400_g1, human Tert: Hs00162669_m1, Mouse Hprt: Mm01545399_m1, mouse Nanog: Ma02019550_s1.

As the positive control for quantitative PCR, cDNA extracted from mesenchymal stem cells established by the following manner was used.

One vial ($2.5 \times 10^7$ cells) of human bone marrow-derived mononuclear cells (hBMMNCs (manufactured by Lonza), Lot 060175A: female, 21 years old, black) was thawed in a 37° C. water bath, and suspended in 10 ml of the MSCGM medium (a growth medium for mesenchymal cells) (manufactured by Lonza). In order to remove DMSO in the frozen solution, this was centrifuged at 300 g and 4° C. for seven minutes and the supernatant was removed. The cell mass thus obtained was resuspended in 10 ml of MSCGM medium, and plated on a 100 mm plate at a concentration of $10^5$ cells/cm$^2$ and cultured at 37° C. Seven days later, the medium was changed. At this time, the suspended cells in the old medium were collected by centrifuging at 300 g and 4° C. for five minutes, and were returned to the cells together with the fresh medium. On day 13 when the adherent cells became confluent, the supernatant was removed, non-adherent cells were washed off with a phosphate buffer, and adherent cells were collected by detaching with a 0.05% trypsin-EDTA solution and plated at a concentration of 3000 cells/cm$^2$. RNA was collected from the cells of the third subculture, and cDNA was synthesized.

Example 5. Induction of Human Pluripotent Stem Cells from Undifferentiated Stem Cells Present in a Postnatal Human Adult Bone Marrow Tissue From human adult bone marrow-derived cells (trade name: Human Bone Marrow-Derived Mononuclear Cell) containing undifferentiated stem cells present in a postnatal human adult bone marrow tissue, the cells were established under the low serum (2%) and the high serum (10%) culture conditions, and were used in the experiment for inducing pluripotent stem cells. Thus, one vial each ($2.5 \times 10^7$ cells) of frozen human bone marrow-derived mononuclear cells (hBMMNCs (manufactured by Lonza), Lot 060809B: female, 20 years old, white/and hBMMNCs (manufactured by Lonza), Lot 060470B: female, 20 years old, black) was thawed in a 37° C. water bath, and suspended in 10 ml of the MAPC medium for use in the low serum culture. In order to remove DMSO in the frozen solution, this was centrifuged at 300 g and 4° C. for seven minutes and the supernatant was removed.

The cell mass thus obtained was resuspended, and plated at a concentration of $10^5$ cells/cm$^2$ on a 100 mm plate coated with 10 ng/ml fibronectin. Growth factors [10 ng/ml PDGF- BB (manufactured by Peprotech), 10 ng/ml EGF (manufactured by Peprotech), 10 ng/ml IGF-1 (manufactured by Peprotech)] were added. Three days later, growth factors were only added. Seven days later, the suspended cells and the medium were collected except the adherent cells, and centrifuged at 300 g and 4° C. for five minutes. After the supernatant was removed, the cells were resuspended in a fresh medium. The cell suspension was returned to the original 10 cm dish, and growth factors were added thereto. On day 10 when the adherent cells became confluent, the supernatant was removed, non-adherent cells were washed off with a phosphate buffer, and adherent cells were collected by detaching with a 0.05% trypsin-EDTA solution, and using a cell banker (manufactured by Juji Field), the primary culture was stored frozen.

Using the human bone marrow-derived mononuclear cell of the same lot, the cells were established using a MSCGM medium (manufactured by Lonza) containing 10% FBS under the high serum condition. The Human Bone Marrow-Derived Mononuclear Cells were plated at a concentration of $10^5$ cells/cm$^2$ in a 100 mm plate to which 10 ml of the MSCGM medium had been added, and cultured at 37° C. Seven days later, the suspended cells and the medium were collected except the adherent cells, and centrifuged at 300 g and 4° C. for five minutes, and after the supernatant was removed, the cells were resuspended in a fresh medium. The cell suspension was returned to the original 10 cm dish, and culturing was continued. On day 13 when the adherent cells became confluent, the supernatant was removed, non-adherent cells were washed off with a phosphate buffer. Adherent cells were collected by detaching with a 0.05% trypsin-EDTA solution, and using a cell banker (manufactured by Juji Field), the primary culture was stored frozen.

One vial each of the human bone marrow-derived primary culture cells that were established under the high serum and the low serum conditions and stored frozen was thawed in a 37° C. incubator. Two ml of the medium used for the establishment was added to the cells respectively, and the cells were plated at a concentration of $10^4$ cells/cm$^2$ on a 6-well plastic culture dish of which bottom had been coated with matrigel (manufactured by Becton Dickinson) at a concentration of 20 μg/cm$^2$ and cultured for 14 hours (a second subculture cells). Fourteen hours later, the medium was removed, and the mCAT1 adenovirus vector prepared in Example 2 at an amount equivalent to a m.o.i. of 10 in 500 μl of the Hank's balanced salt solution per well was added, and were infected at room temperature for 30 minutes.

Two ml each of the medium used for establishment was added to each well, and cultured at 37° C. Forty eight hours after the introduction of the mCAT-1 adenovirus vector, the medium of each well was replaced with 2 ml of the retrovirus vector solution (polybrene at a final concentration of 4 μg/ml was added) of four genes (Oct3/4, Sox2, Klf4, c-Myc) which were prepared in Example 1, and cultured at 37° C. for 14 hours. The virus supernatant was removed and replaced with the MEF-conditioned ES medium. Then medium change with the MEF-conditioned ES medium was continued every two days. On examining fourteen days after the introduction of the four genes, one typical colony was found in the low serum condition group of Lot 060809B that exhibits a characteristics of the induced pluripotent stem cells. Said colony was composed of markedly smaller cells than the surrounding cells. In addition to the pluripotent stem cell-like colony, a plurality of colonies were observed in both the low serum group and the high serum group, but they were not stained with alkaline phosphatase.

In order to isolate the pluripotent stem cell-like colonies, the wells were washed with the Hank's balanced salt solution, and then colonies were surrounded by a cloning ring (manufactured by Iwaki) to the bottom of which silicone grease had been applied. One hundred μl of the Detachment Medium For Primate ES Cells (manufactured by ReproCELL) was added in the ring and cultured at 37° C. for 10 to 20 minutes. The cell suspension in the ring containing the detached colony was added to 2 ml of the MEF-conditioned ES medium, and plated in one well of a MEF-coated 24-well plate. After culturing at 37° C. for 8 to 14 hours, the medium was changed, and subsequently medium change was continued every two days, and 8 days later a second subculture was carried out.

The medium was removed, washed with the Hank's balanced salt solution, the Detachment Medium For Primate ES Cells (manufactured by ReproCELL) was added, cultured at 37° C. for 10 minutes, and 2 ml of the medium was added to stop the reaction. The cell suspension was transferred to a centrifuge tube, and centrifuged at 4° C. and 200 g for 5 minutes to remove the supernatant. The cells were resuspended in the MEF-conditioned ES medium, and plated in 4 wells of the MEF-coated 24-well plate. Medium change was continued every 2 days, and seven days after the second subculture, the cells were subjected to alkaline phosphatase staining, and the cloned colony-derived cells were stained blue violet.

Figure 1:
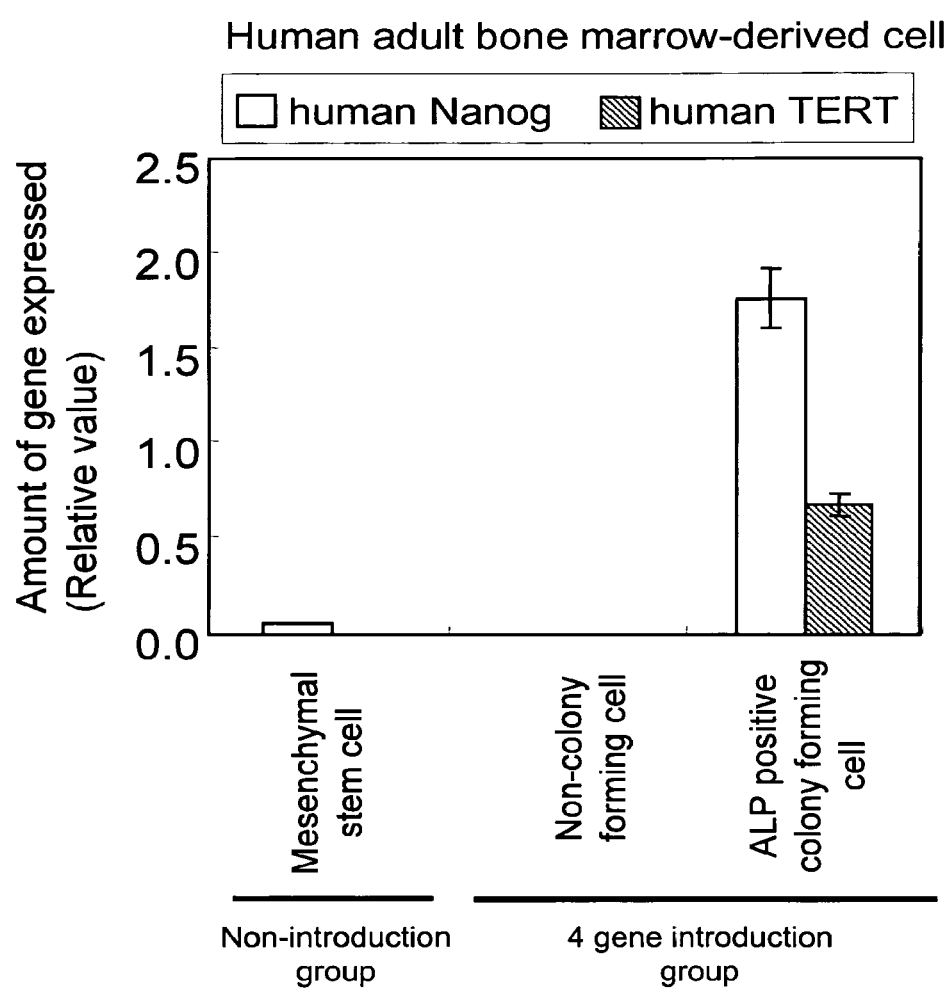
FIG. 1: Four genes of Oct3/4, Sox2, Klf4 and c-Myc were introduced into cells established under a low serum condition from mononuclear cells derived from a human adult bone marrow, and RNA was extracted from the colonies obtained, and the amount expressed of the human Nanog and human Tert genes was demonstrated by quantitative PCR. Fibroblasts and mesenchymal stem cells in which the four genes were not introduced were used as the control in the experiment. The amount expressed of the gene was expressed by a relative value in which the amount expressed was normalized by the amount expressed of the human HPRT gene, and by setting as one the amount expressed of the gene in alkaline phosphatase-positive colonies induced from a neonatal skin fibroblast established by example 6. It was confirmed that the expression of Nanog and Tert was significantly high in colonies in which four genes were introduced and which were positive for alkaline phosphatase.

Furthermore, by quantitative PCR, it was confirmed that Nanog and Tert were expressed by the colony of alkaline phosphatase activity-positive pluripotent stem cells. When compared to the mesenchymal stem cells established in Example 4, the amount expressed of Nanog was as much as 30-fold higher. The expression of Tert was noted only in said pluripotent stem cells, and not in the mesenchymal stem cells. In the cells that did not form colonies despite the introduction of the four genes, Nanog or Tert was not expressed (FIG. 1).

From the foregoing, when human adult bone marrow-derived cells were used, the pluripotent stem cells were obtained from the low serum culture group but not at all from the high serum culture group (Lot 060809B and Lot 060470B) (Table 2). Also, culturing under the low serum condition was suitable for the maintenance of the undifferentiated cells.

Example 6. Induction of Human Pluripotent Stem Cells from Undifferentiated Stem Cells Present in Human Neonatal Skin Using cells (trade name: Neonatal Normal Human Skin Fibroblasts, primary culture) derived from a human neonatal tissue, a human tissue immediately after birth, the induction of human pluripotent stem cells from undifferentiated stem cells present in the skin of a human neonate was attempted.

One vial of the frozen Neonatal Normal Human Skin Fibroblasts (primary culture, manufactured by Lonza, Lot 5F0438) was thawed in a 37° C. incubator, and was suspended in the MCDB202 modified medium, a medium containing 2% fetal bovine serum, 5 μg/ml insulin, 50 μg/ml gentamycin, 50 ng/ml amphotericin-B (FBM medium, manufactured by Lonza) to obtain 12 ml of a cell suspension. Two ml each of the cell suspension was plated on a 6-well plastic culture dish of which bottom had been coated with matrigel (manufactured by Becton Dickinson) at a concentration of 20 μg/cm$^2$ (second subculture cells).

Fourteen hours later, the medium was removed, and the mCAT1 adenovirus vector prepared in Example 2 at an amount equivalent to a m.o.i. of 5 in 500 µl of the Hank's balanced salt solution per well was added, and was infected at room temperature for 30 minutes. To each well, 2 ml of the FBM medium was added respectively, and cultured at 37° C. Forty eight hours after the introduction of the mCAT-1 adenovirus vector, the medium of each well was replaced with 2 ml of the retrovirus vector solution (polybrene at a final concentration of 4 µg/ml was added) of the four genes (Oct3/4, Sox2, Klf4 and c-Myc) prepared in Example 1, and cultured at 37° C. for 4 hours.

The virus supernatant was removed and replaced with the MEF-conditioned ES medium. Then medium change with the MEF-conditioned ES medium was continued every two days, and fourteen days after the introduction of the four genes, one well of the 6-well plate was subjected to alkaline phosphatase staining. As a result, six pluripotent stem cell-like alkaline phosphatase-positive colonies were obtained. Alkaline phosphatase-positive colonies were composed of markedly smaller cells than the neonatal normal human skin fibroblasts.

Figure 2:
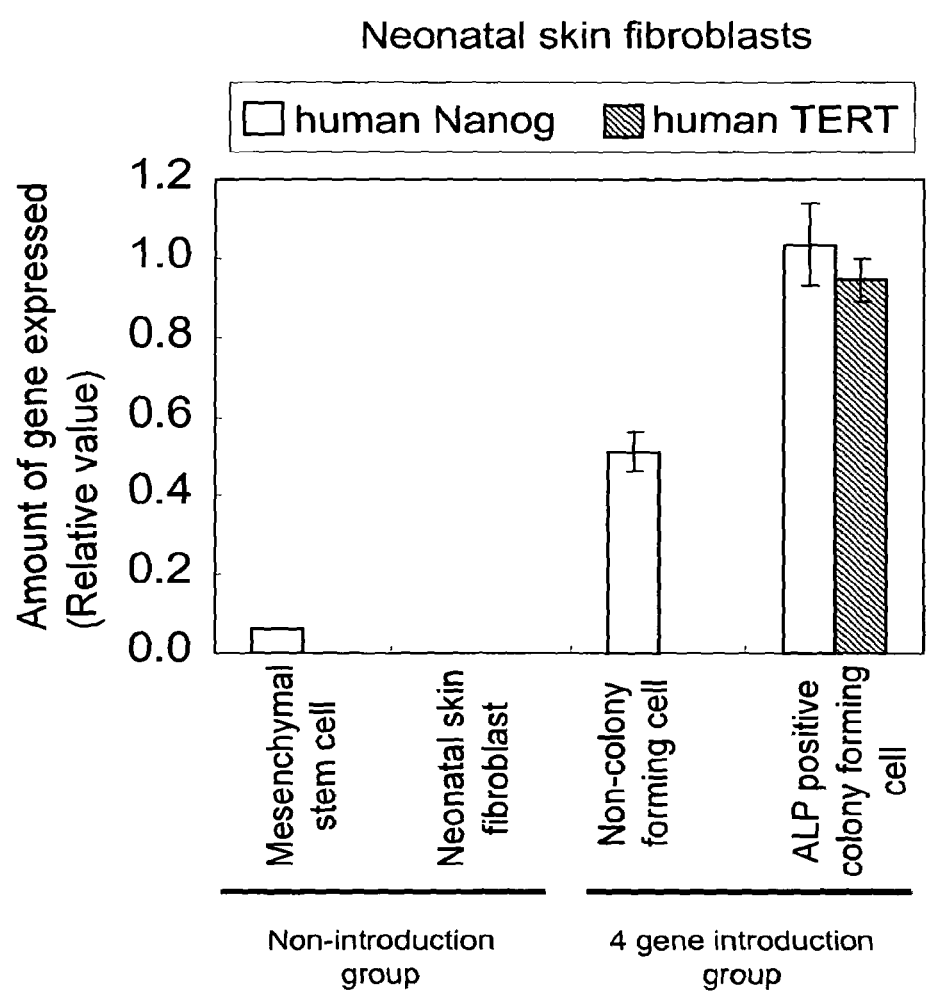
FIG. 2: Four genes of Oct3/4, Sox2, Klf4 and c-Myc were introduced into the primary culture fibroblasts derived from a neonatal skin, RNA was extracted from the colonies obtained, and the amount expressed of the human Nanog and human Tert genes was demonstrated by quantitative PCR. Its parental fibroblasts and mesenchymal stem cells in which four genes were not introduced were used as the control in the experiment. The amount expressed of genes was normalized by the amount expressed of the human HPRT gene, and further was expressed by a relative value by setting as one the amount expressed of the gene in alkaline phosphatase-positive colonies induced from a neonatal skin fibroblast established by example 6. It was confirmed that the expression of Nanog and Tert was significantly high in colonies in which four genes were introduced and which were positive for alkaline phosphatase.

Subsequently, by quantitative PCR, it was confirmed that Nanog and Tert were expressed by the colonies of alkaline phosphatase activity-positive pluripotent stem cells. When compared to the mesenchymal stem cells established under the high serum (10%) culture condition in Example 5, the neonatal normal human skin fibroblasts before the introduction of the four genes did not express Nanog, whereas in the case of the cells after the introduction of the four genes, 9-fold as much in the cells that are not forming colonies and 18-fold as much expression of Nanog in the alkaline phosphatase activity-positive colonies were observed (FIG. 2). On the other hand, the expression of Tert was only noted in the alkaline phosphatase activity-positive colonies. From this, the pluripotent stem cells are defined by the characteristics of alkaline phosphatase activity-positive and Nanog-positive and Tert-positive. Also, the neonatal normal human skin fibroblasts were confirmed to be the cells that have a relatively high efficiency of inducing the pluripotent stem cells and that can express Nanog by the introduction of the four genes.

Colonies of the pluripotent stem cells were isolated in the following manner. On day 17 after gene introduction, six colonies with a characteristic shape were selected from the remaining wells. After washing the wells with the Hank's balanced salt solution, colonies were surrounded by a cloning ring (manufactured by Iwaki) to the bottom of which silicone grease had been applied. One hundred µl of the Detachment Medium For Primate ES Cells (manufactured by ReproCELL) was added in the ring and cultured at 37° C. for 20 minutes. The cell suspension in the ring containing the detached colonies was added to 2 ml of the MEF-conditioned ES medium, and plated in one well of a MEF-coated 24-well plate. After culturing at 37° C. for 14 hours, the medium was changed, and subsequently medium change was continued every two days, and 8 days later a second subculture was carried out. The medium was removed, the cells were washed with the Hank's balanced salt solution, the Detachment Medium For Primate ES Cells was added and cultured at 37° C. for 10 minutes, and 2 ml of the medium was added to stop the reaction.

The cell suspension was transferred to a centrifuge tube, and centrifuged at 4° C. and 200 g for 5 minutes, and the supernatant was removed. The cells were resuspended in the MEF-conditioned ES medium, and plated on four wells of a MEF-coated 24-well plate. Seven days after the second subculture, in a subculturing method described below, the cells were plated on a 60 mm plastic culture dish of which bottom had been coated with matrigel at a concentration of 20 µg/cm². Further eight days later (37 days after the introduction of the four genes), a third subculture was conducted, and plated on two matrigel-coated 60 mm plastic culture dishes, and part of it was used in alkaline phosphatase staining and RNA extraction. The result confirmed that the cells derived from the cloned colonies are alkaline phosphatase activity-positive and are expressing Nanog and Tert at high rate, thereby endorsing that they are pluripotent stem cells.

The induced pluripotent stem cells were subcultured every 5 to 7 days for maintenance and growth. From the plastic culture dish on which subculturing is to be conducted, the medium was removed, the cells were washed with the Hank's balanced salt solution, dispase or the Detachment Medium For Primate ES Cells was added, and cultured at 37° C. for 5 to 10 minutes. When more than half of the colonies were detached, the ES medium was added to stop the reaction, and the cell suspension was transferred to a centrifuge tube. When colonies precipitated on the bottom of the tube, the supernatant was removed, and the ES medium was added again for suspension. After examining the size of the colonies, any extremely large ones were divided into appropriate sizes by slowly pipetting. Appropriately sized colonies were plated on a matrigel-coated plastic culture dish with a base area of about 3 to 6 times that before subculture. The colony-derived pluripotent stem cells are being grown and maintained now.

As shown in Table 2, the Neonatal Normal Human Skin Fibroblasts in the lot (Lot 5F0474) other than the above lot 5F0438 exhibited a favorable induction of pluripotent stem cells. From comparison to Example 5, cells derived from young individuals or cells of which culturing time is short were thought to be suitable for the induction of the pluripotent stem cells.

From the above results, when cells derived from human neonatal tissue that is a human postnatal tissue containing undifferentiated cells were subjected to a second subculture in a culture medium containing 2% serum, it was possible to induce the pluripotent stem cells.

Example 7. Induction of Human Pluripotent Stem Cells from Undifferentiated Stem Cells Present in a Human Adult Skin Then, using human adult tissue-derived cells (trade name: Adult Normal Human Skin Fibroblasts, primary culture) containing undifferentiated stem cells present in a human adult skin, the induction of pluripotent stem cells of the present invention was carried out.

One vial each of the frozen Adult Normal Human Skin Fibroblasts (primary culture, manufactured by Lonza, Lot 6F3535: 28 years old, female, white, Lot 6F4026: 39 year old, female, white) was thawed in a 37° C. incubator, suspended in the FBM medium, and 12 ml of the cell suspension was obtained, respectively. Two ml each of the cell suspensions was plated on a 6-well plastic culture dish of which bottom had been coated with matrigel at a concentration of 20 µg/cm² (second subculture cells).

Fourteen hours later, the medium was removed, and the mCAT1 adenovirus vector prepared in Example 2 at an amount equivalent to a m.o.i. of 5 in 500 µl of the Hank's balanced salt solution per well was added, and was infected at room temperature for 30 minutes. To each well, 2 ml of the FBM medium was added, and cultured at 37° C. Forty eight hours after the introduction of the mCAT-1 adenovirus vector, the medium of each well was replaced with 2 ml of the retrovirus vector solution (polybrene at a final concentration of 4 µg/ml was added) of the four genes (Oct3/4, Sox2, Klf4 and c-Myc) prepared in Example 1, and cultured at 37° C. for 4 hours. The virus supernatant was removed and replaced with the MEF-conditioned ES medium. Then medium change with the MEF-conditioned ES medium was continued every two days, and thirteen days after the introduction of the four genes, alkaline phosphatase staining was carried out. As a result, two pluripotent stem cell-like alkaline phosphatase-positive colonies per well were obtained from the Lot 6F3535, whereas no alkaline phosphatase-positive colonies were obtained from the Lot 6F4242 (Table 2).

From comparison to Example 6, the neonate-derived cells among the skin fibroblasts had a higher efficiency of inducing the pluripotent stem cells. Also, among the Adult Normal Human Skin Fibroblasts, cells derived from younger donors had a higher transformation efficiency. From the foregoing, it was demonstrated that the efficiency of inducing the pluripotent stem cells decreases in an age-dependent manner.

Example 8. Examination Using Neonatal Normal Human Skin Fibroblasts of the Third Subculture One vial of frozen Neonatal Normal Human Skin Fibroblasts (primary culture, manufactured by Lonza, Lot 5F0439) was thawed in a 37° C. incubator, suspended in the FBM medium, and plated on two 100 mm plastic culture dishes (a second subculture). After culturing for six days until a 70 to 90% confluence could be obtained, the cells were detached using a 0.025% trypsin-EDTA solution (manufactured by Lonza), centrifuged at 4° C. and 200 g for 5 minutes, and the supernatant was removed. The second subcultured cells collected were stored frozen using the cell banker.

The frozen second subculture cells were thawed in a 37° C. incubator, suspended in 12 ml of the FBM medium, centrifuged at 4° C. and 200 g for 5 minutes, and the supernatant was removed. The cells were suspended, and plated at a concentration of $10^4$ cell/$cm^2$ on a 100 mm plastic culture dish of which bottom had been coated with matrigel at a concentration of 20 µg/$cm^2$ (a third subculture). Fourteen hours later, the medium was removed, and the mCAT1 adenovirus vector prepared in Example 2 at an amount equivalent to a m.o.i. of 5 in 2 ml of the Hank's balanced salt solution was added, and was infected at room temperature for 30 minutes. To each well, 10 ml of the FBM medium was added, and cultured at 37° C.

Forty eight hours after the introduction of the mCAT-1 adenovirus vector, the medium was removed, and replaced with 10 ml of the retrovirus vector solution (polybrene at a final concentration of 4 µg/ml was added) of the four genes (Oct3/4, Sox2, Klf4 and c-Myc) prepared in Example 1, and cultured at 37° C. for 4 hours. The virus supernatant was removed and replaced with the MEF-conditioned ES medium. Then medium change with the MEF-conditioned ES medium was continued every two days, and fourteen days after the introduction of the four genes, alkaline phosphatase staining was carried out. As a result, five pluripotent stem cell-like alkaline phosphatase-positive colonies were obtained. By calculating based on the area of the bottom, this indicates that 0.83 colony per well of the 6-well plate was obtained (Table 2).

From comparison to Example 6, it was demonstrated that the efficiency of inducing the pluripotent stem cells decreases with the prolonged culture period.

Example 9. Induction of Human Pluripotent Stem Cells from Undifferentiated Stem Cells Present in the Umbilical Cord (1)

Using the cells (trade name: Normal Human Umbilical Vein Endothelial Cells, primary culture) derived from a human umbilical cord, a human tissue immediately after birth, the induction of the human pluripotent stem cells of the present invention from undifferentiated stem cells present in the umbilical cord was attempted.

One vial of the frozen Normal Human Umbilical Vein Endothelial Cells (primary culture, manufactured by Lonza) was thawed in a 37° C. incubator, and suspended in the Endothelial Cell Medium kit-2 manufactured by Lonza (2% serum) (hereinafter referred to as EBM-2) to obtain 12 ml of the cell suspension. About $10^5/2$ ml/well each of the cell suspension was plated to a 6-well plastic culture dish of which bottom had been coated with matrigel at a concentration of 20 µg/$cm^2$ (second subculture). Six hours later, the medium was removed, and the mCAT1 adenovirus vector prepared in Example 2 at an amount equivalent to a m.o.i. of 5 in 500 µl of the Hank's balanced salt solution per well was added, and infected at room temperature for 30 minutes.

2.5 ml each of the EBM-2 medium was added to each well, and cultured at 37° C. Forty eight hours after the introduction of the mCAT-1 adenovirus vector, the medium of each well was replaced with 2 ml each of the retrovirus vector solutions (polybrene at a final concentration of 5 µg/ml was added) of the four genes (Oct3/4, Sox2, Klf4 and c-Myc) prepared in Example 1, and cultured at 37° C. for 4 hours. The virus supernatant was removed and replaced with the MEF-conditioned ES medium. Then medium change with the MEF-conditioned ES medium was continued every two days. Twelve days after the introduction of the four genes, colonies were confirmed.

Thirteen days after the introduction of the four genes, the induced colonies were stained with alkaline phosphatase activity.

From the above results, when cells derived from human umbilical cord that is a human tissue immediately after birth containing undifferentiated cells were subjected to a second subculture in a culture medium containing 2% serum, it was possible to induce the pluripotent stem cells.

Example 10. Induction of Human Pluripotent Stem Cells from Undifferentiated Stem Cells Present in the Umbilical Cord (2)

As described below, using the cells (trade name: Normal Human Umbilical Artery Smooth Muscle Cells, the third subculture) derived from a human umbilical cord, a human tissue immediately after birth, the induction of the human pluripotent stem cells of the present invention from undifferentiated stem cells present in the umbilical cord was attempted.

One vial of the frozen Normal Human Umbilical Artery Smooth Muscle Cells (the third culture, manufactured by Lonza) was thawed in a 37° C. incubator, and suspended in the Smooth Muscle Cell Medium kit-2 manufactured by Lonza (5% serum) (hereinafter referred to as SmGM-2) to obtain 12 ml of the cell suspension. About $10^5/2$ ml/well each of the cell suspension was plated to a 6-well plastic culture dish (manufactured by Becton Dickinson) of which bottom had been coated with matrigel (manufactured by Becton Dickinson) at a concentration of 20 μg/cm² (the fourth subculture). One day later, the medium was removed, and the mCAT1 adenovirus vector at an amount equivalent to a m.o.i. of 1.25 to 5 in 500 μl of the Hank's balanced salt solution per well was added, and infected at room temperature for 30 minutes. 2.5 ml each of the SmGM-2 medium was added to each well, and cultured at 37° C.

Forty eight hours after the introduction of the mCAT-1 adenovirus vector, the medium of each well was replaced with 2 ml each of the retrovirus vector solutions (polybrene at a final concentration of 5 μg/ml was added) of the four genes (Oct3/4, Sox2, Klf4 and c-Myc) prepared in Example 1, and cultured at 37° C. for 4 hours. The virus supernatant was removed and replaced with the MEF-conditioned ES medium. Then medium change with the MEF-conditioned ES medium was continued every two days. Thirteen days after the introduction of the four genes, colonies were confirmed. However, the induced colonies were not stained with alkaline phosphatase activity.

From the above results, it was revealed that though the cells derived from human umbilical cord which is a human tissue immediately after birth contains undifferentiated cells present in the umbilical cord, when the cells were subjected to a fourth subculture in a culture medium containing 5% serum, the induction of the pluripotent stem cells was extremely difficult.

Example 11. Induction of Mouse Pluripotent Stem Cells from Undifferentiated Stem Cells Present in a Mouse Postnatal Tissue Using mouse bone marrow-derived cells, a mouse postnatal tissue, the induction of pluripotent stem cells of the present invention from undifferentiated stem cells present in a mouse postnatal tissue was attempted.

Femurs and tibias were extracted from 4 to 6 week-old mice (c57BL/6N lineage, 4-week-old, female) taking utmost care not to bring in any other tissue. By soaking the collected bone in 70% ethanol for a short period of time, the cells that attached to the outside of the bone were killed to prevent the contamination of cells other than the bone marrow. After ethanol treatment, the bone was immediately transferred to IMDM (Iscove's Modified Dulbecco's Medium) (manufactured by SIGMA) to prevent the effect of the cells inside of the bone marrow. The outside of each bone was wiped with Kimwipe to remove the connective tissue. All of the treated bone was transferred to a mortar having IMDM, and was smashed with a pestle. After washing several times with IMDM, the bone was cut into pieces with scissors. After further washing with IMDM several times, bone fragments were transferred to centrifuge tubes.

After removing IMDM, 10 ml per five mice of IMDM containing 0.2% collagenase I (manufactured by SIGMA) was added, and shaken at 37° C. for 1 hour. After shaking, the suspension was stirred several times using a Pipetman, and then the supernatant was transferred to another tube, to which an equal amount of cold 10% FBS-containing IMDM was added to stop the enzyme reaction. The bone fragments after enzyme treatment were transferred to a mortar containing cold 10% FBS-containing IMDM, and smashed again with a pestle, and after stirring several times, the supernatant was collected. The cell suspension thus collected was filtered by sequentially passing through a Nylon mesh of 70 μm and 40 μm in diameter. The cell suspension was centrifuged at 4° C. and 600 g for 7 minutes, and cells derived from the mouse deep bone marrow were collected.

The cells derived from mouse deep bone marrow were suspended in the MAPC medium, and plated at a concentration of $10^5$ cells/cm². For plating of cells, a dish previously coated with a phosphate buffer containing 10 ng/ml fibronectin (Becton Dickinson) was used. To the medium, growth factors [10 ng/ml PDGF-BB (manufactured by Peprotech), 10 ng/ml EGF (manufactured by Peprotech), 1000 units/ml LIF (manufactured by Chemicon)] were added at the time of use. Three days after plating, growth factors were only added without changing the medium. Six days later, non-adherent cells were washed off with the phosphate buffer, and adherent cells were collected by detaching with a 0.05% trypsin-EDTA solution (manufactured by Invitrogen), and using a cell banker (manufactured by Juji Field), the cells were stored frozen as the primary culture.

The primary culture cells that had been stored frozen were thawed in a 37° C. water bath, and suspended in 10 ml of the MAPC medium that is a medium containing 2% FBS. In order to remove DMSO in the frozen solution, it was centrifuged at 4° C. and 300 g for 7 minutes, and the supernatant was removed. The cell mass obtained was resuspended, and plated at a concentration of $2.5 \times 10^3$ cells/cm² on a 12-well plastic plate having the bottom which had been gelatin-coated with 0.1% gelatin/phosphate buffer, and 2 ml each of the MAPC medium was added (the second subculture).

Eight to 14 hours later, the medium was removed, and 2 ml each of the four gene retrovirus vector solution prepared as in Example 1 was added thereto and cultured at 37° C. for 4 to 14 hours. Then the virus solution was removed, and replaced with the mouse ES medium [the ES medium to which a final concentration of 0.3% FBS (manufactured by Invitrogen), 1000 units/ml LIF (manufactured by Chemicon), and 0.1 mM 2-mercaptoethanol were added]. Then medium change with the mouse ES medium was continued every three days, and 5 to 7 days after the introduction of the four genes, said pluripotent stem cells formed colonies comprising mouse ES cell-like small cells. The colonies of the induced pluripotent stem cells were stained blue violet by alkaline phosphatase activity.

From the remaining wells of the 12-well plate, the mouse pluripotent stem cells were subcultured, and subculture was continued to a gelatin-coated 100 mm plate. From the seventh subculture cells, RNA was extracted using the RNeasy mini kit (manufactured by QIAGEN) and cDNA was synthesized. Using the cDNA, quantitative PCR was conducted to confirm the expression of Nanog.

The mouse pluripotent stem cells of the seventh subculture were subcutaneously transplanted to the back of three syngeneic C57BL/6N mice at $3 \times 10^5$ cells/mouse, and 38 days later the teratoma that formed was extracted. Teratoma was formed in all three mice. From the extracted teratoma, slices were prepared, and differentiation potential into three germ layers was analyzed by immunological staining and histological staining (HE stain, alcian blue stain). As a result, MAP2-positive cells (the nervous system) and GFAP-positive cells (the nervous system) as the ectodermic system, skeletal muscle cells (myocytes) and cartilage tissues as the mesodermic system, and intestinal tract tissues as the endodermic system were observed.

In order to maintain and grow the mouse pluripotent stem cells, they were subcultured every 3 to 4 days. The medium was removed from the plastic culture dish in which subculture is carried out, washed with phosphate buffer, a 0.05% trypsin-EDTA solution was added, and cultured at 37° C. for 5 minutes. When the cells detached, the ES medium was added to stop the reaction, and the cell suspension was transferred to a centrifuge tube. By centrifuging at 200 g for 5 minutes, the supernatant was removed, and after suspending the precipitate in the mouse ES medium, the cells were plated in a gelatin-coated plate at a concentration of $10^4$ cells/cm². The pluripotent stem cells induced from the cells derived from the mouse bone marrow cultured in low serum in the same subculture method could be cultured for a long time.

As described above, pluripotent stem cells were induced from the postnatal mouse bone marrow-derived cells established under the low serum condition.

Example 12. Induction of Mouse Pluripotent Stem Cells by the Introduction of Three Genes and Histone Deacetylase Inhibitor Treatment Using cells derived from mouse bone marrow that is a mouse postnatal tissue, the induction of pluripotent stem cells was carried out with the introduction of three genes and histone deacetylase inhibitor treatment.

The primary culture cells derived from mouse bone marrow containing undifferentiated stem cells that had been stored frozen after preparing in a manner similar to Example 11 were plated at a concentration of $5 \times 10^3$ cells/cm² on a 24-well plastic plate (manufactured by Becton Dickinson) having the bottom which had been gelatin-coated with a 0.1% gelatin/phosphate buffer, and 2 ml each of the MAPC medium was added.

Eight hours later, the medium was removed, 2 ml each of the three gene (human Oct3/4, Sox2 and Klf4) retrovirus vector solution prepared as in Example 1 were added, and after further adding MS-275, a histone deacetylase inhibitor, at a final concentration of 1 or 0.1 µM, they were cultured at 37° C. for 14 hours. Then after removing the virus solution, 2 ml each of the MAPC medium containing MS-275, a histone deacetylase inhibitor, at a final concentration of 1 or 0.1 µM was added. Three days later, the medium was replaced with the mouse ES medium [a final concentration of 0.3% FBS (manufactured by Invitrogen), 1000 units/ml LIF (manufactured by Chemicon) and 0.1 mM 2-mercaptoethanol were added to the ES medium at the time of use].

Medium change with the mouse ES medium was continued every 2 to 3 days. Twelve days after the introduction of three genes (human Oct3/4, Sox2 and Klf4) retrovirus vector, the cells were subcultured from each well of the 24-well plastic plate to each well of a 6-well plastic plate. A portion of it was also cultured in a 24-well plastic plate. Fifteen days after said three gene introduction and MS-275 treatment, the pluripotent stem cells formed colonies composed of mouse ES cell-like small cells. The colonies of said pluripotent stem cells were stained blue violet by alkaline phosphatase activity.

Figure 3:
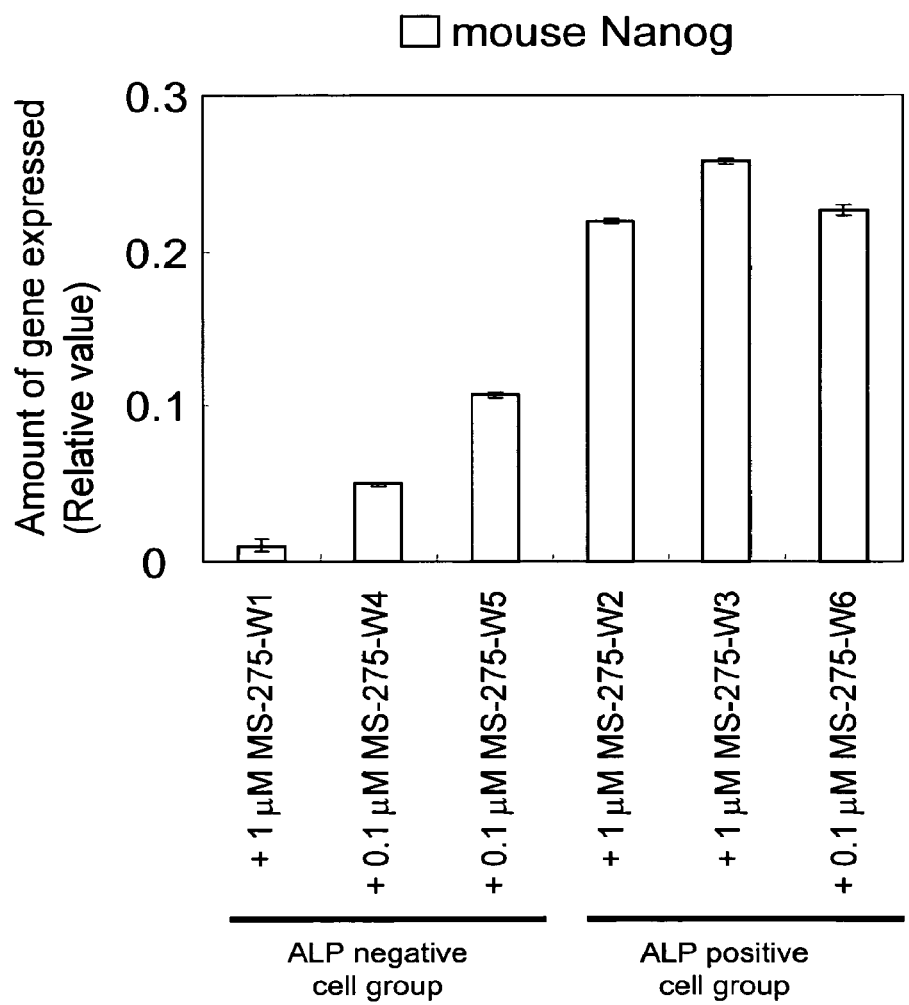
FIG. 3: After three gene introduction and treatment with MS-275 (0.1 or 1.0 µM), a histone deacetylase (HDAC) inhibitor by using cells derived from a mouse bone marrow established under a low serum condition, RNA was extracted from the colonies obtained, and the amount expressed of Nanog was demonstrated by quantitative PCR. From the cells in which three genes were introduced and which were treated with a histone deacetylase inhibitor, alkaline phosphatase-positive cell group (colonies) was formed, and it was confirmed that the expression of Nanog in these colonies was significantly higher than the alkaline phosphatase-negative colonies.

Then, the amount expressed of the Nanog gene was confirmed by quantitative PCR, and the expression of mouse Nanog of colonies of pluripotent stem cells having alkaline phosphatase activity was confirmed (FIG. 3).

Eighteen days after said three gene introduction and MS-275 treatment, the pluripotent stem cells were subcultured from each well of the 6-well plate to a gelatin-coated 100 mm plate. Subculture was continued similarly.

Twenty nine days after said three gene introduction and MS-275 treatment, the mouse pluripotent stem cells were subcutaneously transplanted to the back of syngeneic C57BL/6N mice at $2 \times 10^7$ cells/mouse, and 34 days later the teratoma that formed was extracted. From the extracted teratoma, slices were prepared, and differentiation potential into three germ layers was analyzed by immunological and histological staining (HE stain, alcian blue stain). As a result, GFAP-positive cells (the nervous system) and keratin producing cells (skin cells) as the ectodermic system, smooth muscle actin-positive cells (smooth muscle cells), bone tissues and cartilage tissues as the mesodermic system, and intestinal tract tissues (endodermal epithelium positive for MUC-1) as the endodermic system were observed.

Example 13. Induction of Mouse Pluripotent Stem Cells by the Introduction of Three Genes Then, using cells derived from mouse bone marrow that is a mouse postnatal tissue, the induction of mouse pluripotent stem cells was carried out with the introduction of three genes.

The primary culture cells derived from mouse bone marrow containing undifferentiated stem cells that had been stored frozen after preparing in Example 11 were plated at a concentration of $1 \times 10^4$ cells/cm² on a 24-well plastic plate (manufactured by Becton Dickinson) having the bottom which had been gelatin-coated with a 0.1% gelatin/phosphate buffer solution, and 2 ml each of the MAPC medium was added.

Two days later, the medium was removed, 2 ml each of the three gene (human Oct3/4, Sox2 and Klf4) retrovirus vector solution prepared as in Example 1 were added, and after culturing at 37° C. for 1 day, the virus solution was removed, and 2 ml each of the MAPC medium was added. Three days later, the medium was replaced with the mouse ES medium [a final concentration of 0.3% FBS (manufactured by Invitrogen), 1000 units/ml LIF (manufactured by Chemicon) and 0.1 mM 2-mercaptoethanol were added to the ES medium at the time of use]. Then medium change with the mouse ES medium was continued every 2 to 3 days. Eleven days after the introduction of three gene (human Oct3/4, Sox2 and Klf4) retrovirus vector, the cells were subcultured from each well of the 24-well plastic plate to each well of a 6-well plastic plate.

Then medium change with the mouse ES medium was continued every 2 to 3 days. Nineteen days after said three gene introduction, the pluripotent stem cells formed colonies composed of mouse ES cell-like small cells. In order to confirm the alkaline phosphatase activity, the medium was removed and then a 10% formalin neutral buffer solution was added to wells, and fixed at room temperature for 5 minutes. After washing with a phosphate buffer etc., the 1 step NBT/BCIP solution (manufactured by Pierce) comprising a chromogenic substrate of alkaline phosphatase was added and reacted at room temperature for 20 to 30 minutes. The colonies of said pluripotent stem cells were stained blue violet by alkaline phosphatase activity.

Then, the amount expressed of the Nanog gene was confirmed by quantitative PCR, and the expression of mouse Nanog of colonies of pluripotent stem cells having alkaline phosphatase activity was confirmed.

Using cells derived from mouse bone marrow that is a mouse postnatal tissue, the induction of pluripotent stem cells was carried out with the introduction of three genes.

The primary culture cells derived from mouse bone marrow containing undifferentiated stem cells that had been stored frozen after preparing in Example 11 were plated at a concentration of $1 \times 10^4$ cells/cm² on a 6-well plastic plate (manufactured by Becton Dickinson) the bottom of which had been gelatin-coated with a 0.1% gelatin/phosphate buffer solution, and the MAPC medium was added in 2 ml portions.

Two days later, the medium was removed, the three gene (human Oct3/4, Sox2 and Klf4) retrovirus vector solution prepared as in Example 1 were added in 2 ml portions, and after culturing at 37° C. for 1 day, the virus solution was removed, and the MAPC medium was added in 2 ml portions. Three days later, the medium was replaced with the mouse ES medium [a final concentration of 0.3% FBS (manufactured by Invitrogen), 1000 units/ml LIF (manufactured by Chemicon) and 0.1 mM 2-mercaptoethanol were added to the ES medium at the time of use]. Medium change with the mouse ES medium was continued every 2 to 3 days. Nine days after the introduction of three gene (human Oct3/4, Sox2 and Klf4) retrovirus vector, the cells were subcultured from each well of the 6-well plastic plate to each well of a 10 cm plastic dish.

Medium change with the mouse ES medium was continued every 2 to 3 days. Seven days after said three gene introduction, the pluripotent stem cells formed colonies composed of mouse ES cell-like small cells. In order to confirm the alkaline phosphatase activity, the medium was removed and then a 10% formalin neutral buffer solution was added to wells, and fixed at room temperature for 5 minutes. After washing with a phosphate buffer etc., the 1 step NBT/BCIP (manufactured by Pierce), a chromogenic substrate of alkaline phosphatase, was added and reacted at room temperature for 20 to 30 minutes. The colonies of said pluripotent stem cells were stained blue violet by alkaline phosphatase activity.

Then, the amount expressed of the Nanog gene was confirmed by quantitative PCR, and the expression of mouse Nanog of colonies of pluripotent stem cells having alkaline phosphatase activity was confirmed.

Forty nine days after said three gene introduction, the mouse pluripotent stem cells were subcutaneously transplanted on the back of syngeneic C57BL/6N mice at $2 \times 10^7$ cells/mouse, and 13 and 17 days later the teratoma that formed was extracted. Slices were prepared from the extracted teratoma, and differentiation potential into three germ layers was analyzed by immunological and histological staining (HE stain, alcian blue stain). As a result, GFAP-positive cells (the nervous system) and keratin producing cells as the ectodermic system, smooth muscle actin-positive cells (smooth muscle cells), bone tissues and cartilage tissues as the mesodermic system, and intestinal tract tissues (endodermal epithelium positive for MUC-1) as the endodermic system were observed.

Likewise, after said three gene introduction, the mouse pluripotent stem cells which were single-sorted based on GFP and SSEA-1 positive with FACSAria, were subcutaneously transplanted on the back of syngeneic C57BL/6N mice at $2 \times 10^7$ cells/mouse, and 13 and 14 days later the teratoma that formed was extracted. Slices were prepared from the extracted teratoma, and differentiation potential into three germ layers was analyzed by immunological and histological staining (HE stain, alcian blue stain). As a result, neural tube derived cells positive for GFAP, Nestin or Neurofilament as ectodermic system and cartilage tissues as the mesodermic system, and intestinal tract tissues (endodermal epithelium positive for MUC-1 and alpha-fetoprotein) as the endodermic system were observed.

From the above results, pluripotent stem cell were obtained by the forced expression of each of three genes of Oct3/4, Sox2, and Klf4 in undifferentiated stem cell present in a postnatal tissue. The pluripotent stem cells showed an in vitro long-term self-renewal ability, and were expressed ES cell marker, Nanog expression and alkaline phosphatase activity, and the ability of differentiation of tissues derivative from all three germ layers (ectoderm, mesoderm and endoderm).

Example 14. Long Term Expansion and Characterization of Human Induced Pluripotent Stem Cells Human induced pluripotent stem (iPS) cell line generated from neonatal human skin fibroblasts (lot #5F0438) in Example 6 which was termed iPS-1 was further sub-cloned with cloning cylinder and 0.25% trypsin-EDTA as described in Example 6. Nine sub-clones which were termed human iPS-1-1, 1-2, 1-3, 1-4, 1-5, 1-6, 1-7, 1-8 and 1-9 were obtained. One of nine sub clones, termed human iPS-1-8 clone, was successfully expanded on MEF feeder cells in human ES medium supplemented with 0.1 mM 2-mercaptoethanol and 10 ng/ml bFGF or in mTeSR1 defined medium (Stem cell Technologies) on matrigel (Invitrogen)-coated culture dishes. Medium was changed for human iPS-1-8 clone culture everyday and usually treated with 5 to 20 μM of Y-27632 (Calbiochem) to avoid cell apoptosis triggered by the passaging procedures. For the passage to continue the culture, human induced pluripotent stem cells were washed with Hanks's balanced solution, incubated in 0.25% trypsin-EDTA (Gibco) at 37° C. for 3 minutes, and then added the culture medium to terminate the trypsin activity. Human induced pluripotent stem cells were centrifuged at 300×g at room temperature or 4° C. for 5 minutes and the supernatant was removed. Precipitated human induced pluripotent stem cells were re-suspended into culture medium. The pluripotent stem cells were usually split into new culture dishes using 1:4 to 1:6 splits. Human iPS-1-8 clone was frozen using Cell freezing solution for ES cells (Reprocell) according to the manufacture's manual.

Human iPS-1-8 clone was morphologically indistinguishable from typical human ES cell colonies that consist of small, round, and compact cells with defined edges when cultured on mitomycin-C treated mouse embryonic fibroblasts (MEFs) (FIG. 4). Human iPS-1-8 clone actively proliferated in mTeSR1 medium. Human iPS-1-8 clone derived cells cultured in mTeSR1 medium was termed human iPS-1-8 mTeSR cells. Human iPS-1-8 clone was able to be passaged more than 30 times, and cultured for more than half year after four factor infections (FIG. 4f, g). Human iPS-1-8 mTeSR cells were able to be stored in liquid nitrogen and recultured in mTeSR medium in the presence of 5 to 20 μM of Y-27632. Population doubling time of human iPS-1-8 mTeSR cells was approximately 48.5 hours when analyzed between passages 19 to 26 which correspond to days 123 to 148 after four factor infection.

Karyotype analysis of long-term cultured human iPS-1-8 clone (1-8 mTeSR) was performed using giemsa stain and multicolor-FISH analysis. Human iPS cells were pretreated with 0.02 μg/ml colecemid for 2 hours, followed by incubation with 0.075 M KCl for 20 minutes, and then fixed with Carnoy's fixative. For multicolor-FISH analysis, cells were hybridized with the multicolor FISH probe (Cambio) and analyzed under DMRA2 fluorescent microscope (Leica). Human iPS-1-8 mTeSR cells mainly maintained a normal karyotype (46XY) after long-term culture in mTeSR (68%) without any chromosomal translocation or deletion (FIG. 4h, Table 3).

For alkaline phosphatase staining, cells were fixed with 10% formalin neutral buffer solution (Wako) at room temperature for 5 minutes, washed with PBS, and incubated with alkaline phosphatase substrate 1 step NBT/BCIP (Pierce) at room temperature for 20-30 minutes. Cells having alkaline phosphatase activity were stained in blue violet. For immunocytochemistry, cultured cells were fixed with 10% formaldehyde for 10 minutes and blocked with 0.1% gelatin/PBS at room temperature for 1 hour. The cells were incubated overnight at 4° C. with primary antibodies against SSEA-3 (MC-631; Chemicon), SSEA-4 (MC813-70; Chemicon) TRA-1-60 (abcam), TRA-1-81 (abcam), CD9 (M-L13; R&D systems), CD24 (ALB9; abcam), CD90 (5E10; BD bioscience), or Nanog (R&D systems). For Nanog staining, cells were permeabilized with 0.1% Triton X-100/PBS before blocking. The cells were washed with PBS for three times, and then incubated with AlexaFluor 488-conjugated secondary antibodies (Molecular Probes) and Hoechst 33258 at room temperature for 1 hour. After further washing, fluorescence was detected with an Axiovert 200M microscope (Carl Zeiss).

Human iPS-1-8 mTeSR cells were positive for alkaline phosphatase (hereinafter referred to as "ALP") activity and the glycolipid antigens SSEA-3 and SSEA-4, the keratin sulfate antigens TRA-1-60 and TRA-1-81, and the protein antigens CD9, CD24, Thy-1 (CD90) staining (FIG. 5).

Total RNA was isolated from human iPS-1-8 clone, its parental fibroblasts, and crude fibroblasts obtained on 17 days after gene transduction by using RNeasy (Qiagen). cDNA was synthesized by SuperScript III (Invitrogen). Gene expressions were detected by PCR using Extaq (Takara). Sequences of the primers were described in Table 4.

Human iPS-1-8 clone expressed human ES marker genes Nanog, TERT, Sall4, Zfp42, GDF3, Dnmt3b, TDGF1, GABRB3, and CYP26A1 though the parental fibroblasts expressed none of those marker genes (FIG. 6a). In contrast to crude fibroblasts, human iPS-1-8 clone down-regulated forced expression of four genes (FIG. 6b).

Human iPS cells cultured in both mTeSR on matrigel □1-8 mTeSR□ and MEF-conditioned medium on matrigel (1-8CM) and its parental fibroblasts (5F0438) were analyzed for global gene expression. The microarray study was carried out using the Affymetrix Human Genome U133 Plus 2.0 gene expression arrays (Affymetrix, Santa Clara, Calif.). The GeneChip® Human Genome U133 Plus 2.0 Array provides comprehensive coverage of the transcribed human genome on a single array and analyzes the expression level of over 47,000 transcripts and variants, including 38,500 well-characterized human genes. Briefly, total RNA was extracted from cells with RNAeasy (Qiagen). Biotin-labelled cRNA was reverse transcribed from 1 μg of total RNA according to Affymetrix technical protocols. Fifteen micrograms of cRNA was fragmented and hybridized to a Affymetrix U133 plus 2 GeneChip arrays at 45° C. for 16 hours and then washed and stained using the Affimetrix Fluidics (Affymetrix). The assays were scanned in the Affimetrix GCS3000 scanner, and the image obtained were analyzed using the GCOS software. Data from this experiment and GEO were investigated with the GeneSpring 7.3.1. software.

For scatter plot analyses, human induced pluripotent stem cell clone-1-8, cultured in mTeSR on matrigel (1-8 mTeSR) and its parental fibroblasts (5F0438) were analyzed based on a set of 21,080 genes with present flag call (P<0.04) or marginal flag call (0.04□P<0.06) for both clone 1-8 and H14 hES line which is data from GEO (GSM151741), were used as a representative of human ES cells for comparison.

For cluster analysis, DNA microarray data for clone-1-8 cultured in mTeSR (1-8 mTeSR), clone 1-8 cultured in MEF-conditioned medium (1-8CM) and its parental fibroblasts (5F0438) were compared with DNA microarray data for Sheff 4 line cultured on MEF (hES1:GSM194307, hES2: GSM194308, hES3: GSM194309), Sheff 4 line cultured on matrigel (hES4: GSM194313, hES5: GSM194314), H14 line cultured on MEF (hES6: GSM151739, hES7: GSM151741), and three fibroblasts (GSM96262 for Fibroblasts1, GSM96263 for Fibroblasts2 and GSM96264 for Fibroblasts3).

The global gene expression profile of the human iPS cell line (clone 1-8) and its parental fibroblasts were analyzed. Cluster analysis using the gene set defined by the International Stem Cell Initiative revealed that the human iPS cell line 1-8 clustered with human ES cell lines but separated from the parental fibroblasts (FIG. 8). Although the pearson correlation coefficient was 0.675 between human ES cell lines sheff4 and H14, the coefficient was 0.835 between human iPS cell line 1-8 and human ES cell line H14 (FIG. 8). This analysis indicate that human iPS cell line 1-8 had a similar gene expression pattern to the human ES cell lines H14. Scatter plot analysis between indicate that the human ES cell marker genes, Nanog, Oct3/4, TDGF1, Dnmt3b, GABRB3, GDF3, Zfp42, ALP, CD9, and Thy-1 showed high correlation between human iPS cell line and human ES cell line H14 (FIG. 7a). In contrast, clone1-8 was different from the parental neonatal fibroblasts (FIG. 7b). This was confirmed by the cluster analysis using the nanog-related genes. Pearson correlation coefficient was 0.908 between human iPS cell line 1-8 and human ES cell line H14 and 0.100 between human iPS cell line 1-8 and its parental fibroblasts (FIG. 9). These analysis reveal that human iPS cell line is indistinguishable from human ES cell line in gene expression.

The promoter regions of Nanog and Oct3/4 were analyzed for methylation of individual CpG sites. Ten nanograms of bisulfite-treated genomic DNA was PCR-amplified with primers containing a T7-promoter and transcripts treated with RNase A. As fragments originating from a methylated CpG sequence contained a G instead of an A-base, they had a 16 Da higher molecular weight than those resulting from the corresponding non-methylated CpG. This mass difference was detected using a MALDI-TOF mass spectrometer (Autoflex, Bruker Daltonics). The spectra produced by the mass spectrometer were analyzed using the EpiTYPER (Sequenom). The percentage methylation of individual CpG sites was calculated using the area under the peak of the signal from the unmethylated and methylated fragments. The percentage methylation of individual CpG sites were calculated using the area under the peak of the signal from the unmethylated and methylated fragments. Table 9 lists up locations and sizes in genome corresponding to amplicon using for methylation analyses. Table 10 lists up the primer sets using for methylation analyses. The Oct3/4 proximal promoter including conserved region 1 (CR1), the Oct3/4 promoter distal enhancer including CR4 and the Nanog proximal promoter including Oct3/4 and Sox2 binding sites were examined (FIG. 10a). As shown in FIG. 10b, cytosine-phosphate-guanosine (CpG) dinucleotides in these regions are demethylated in clone 1-8 derived cells compared to the parental fibroblasts.

Human iPS-1-8 mTeSR cell-suspension (0.5 to $2\times10^6$ cells/mouse) was injected into the medulla of left testis of 7 to 8 week old SCID mice (CB17, Oriental Yeast) using a Hamilton syringe. After 6 to 8 weeks, the teratomas were excised under perfusion with PBS followed with 10% buffered formalin, and subjected to the histological analysis. Human iPS-1-8 mTeSR cells gave rise to teratomas 4 to 8 weeks after transplantation into testes of SCID mice.

Teratomas were embedded in the mounting medium, and sectioned at 10 μm on a cryostat. Serial sections were stained with hematoxylin-eosin (HE) to visualize the general morphology. For the detection of cartilage, alcian blue staining was employed or combined with HE.

For immunostaining, sections were treated with Immunoblock (Dainippon-Sumitomo) for 30 minutes to block non-specific binding. Slides were incubated with the following primary antibodies: anti Nestin polyclonal antibody (PRB-570C, COVANCE, 1:300), anti Type II collagen polyclonal antibody (LB-1297, LSL, 1:200), anti Smooth muscle actin polyclonal antibody (RB-9010-R7, LAB VISION, 1:1), anti α-Fetoprotein polyclonal antibody (A0008, DAKO, 1:500), anti MUC-1 polyclonal antibody (RB-9222-P0, LAB VISION, 1:100), and anti Human nuclei monoclonal antibody (HuNu) (MAB1281, CHEMICON, 1:300). For Type II collagen, before the treatment with primary antibody a section was incubated with Hyaluronidase (25 mg/mL) for 30 minutes. Localization of antigens was visualized by using appropriate secondary antibodies (Alexa fluor 594 and 688, Molecular Probes, 1:600). Nuclei were stained with DAPI. Immunostained teratoma sections were analyzed under a fluorescence microscope (Axio Imager Z1, Zeiss).

Teratomas of human iPS-1-8 mTeSR cells contained tissues representative of three germ layers, neuroectoderm, mesoderm, and endoderm. FIG. 11 shows teratoma that was derived from human iPS-1-8 mTeSR cells cultured for 94 days (T1). Human iPS-1-8 mTeSR cells were injected into SCID mouse testes and analyzed 56 days after injection. HE and alcian blue staining of teratoma tissues reveled that teratomas contained neural epitherium (positive for nestin) cartilage (positive for collagen II), endodermal tract (alpha-fetoprotein). Human iPS-1-8 mTeSR cell derived tissues were distinguished from host tissues by HuNu staining. In T1 teratoma, smooth muscle cells (positive for alpha-SMA) and secretary epithelium (positive for MUC-1) were also observed (FIG. 12). Human iPS-1-8 mTeSR cells which were cultured for 102 days and 114 days, were injected into SCID mouse testes and analyzed 48 days and 42 days (T3) after injection, respectively (T2, FIG. 12, T3, FIG. 13). Tissues representative of three germ layers, neuroectoderm, mesoderm and endoderm, were observed. To confirm whether human iPS can be cryopreserved, human iPS-1-8 mTeSR cells were frozen down, stored in liquid nitrogen and recultured. These cells were injected into SCID mouse testes and analyzed 46 days (T-F1) and 48 days (T-F2) after injection. Tissues representative of three germ layers, neuroectoderm, mesoderm and endoderm, were observed. Melanocytes were also observed in the T-F2 teratoma (FIG. 13). Thus, pluripotency was maintained via freezing and thawing.

Both southern blot analysis and genomic PCR analysis indicated human iPS-1-8 clone carried four transgenes. In southern blot analysis cDNA fragments were prepared by restriction enzyme digestion (XhoI for POU5F1, NotI for Sox2, PstI for KIF4) from the corresponding pMX vector plasmids. These fragments were purified as [32P]-labeled probes with agarose gel electrophoresis and a QIAquick gel extraction kit (QIAGEN). Genomic DNA was prepared from the human iPS clone 1-8 and its parental fibroblasts. Five μg of each genomic DNA was digested with KpnI (POU5F1, Sox2, and Klf4). Fragments were separated on a 0.8% agarose gel, blotted onto HybondXL membrane (GE Healthcare), and hybridized with [32P]-labeled probes. Human iPS clone-1-8 was shown to carry approximately ten copies of both Oct3/4 transgenes and Sox2 transgenes, and a single copy of Klf4 transgene (FIG. 14). In genomic PCR analysis, primer set indicated as c-Myc-total in Table 4 was designed so that the amplicon included whole second intron of c-Myc. Thus, amplicon size of the transgene (338 bp) was smaller than amplicon of endogene (1814 bp). Vector plasmid and the parental fibroblast genome, crude cultured fibroblast genome obtained from 17 days culture post infection were used as a control template. The genomic PCR confirmed clone-1-8 cells carries c-Myc transgene (FIG. 14).

SNP genotyping was performed with the use of the GeneChip Human Mapping 500K Array Set (Affymetrix) according to the manufacture's protocol. Human iPS-1-8 mTeSR cells cultured in mTeSR on matrigel, its parental fibroblasts (5F0438), and fibroblast (5F0416) derived from a different donor were analyzed for this assay. The array set includes a StyI and a NspI chip. Two aliquots of 250 ng of DNA each were digested with NspI and StyI, respectively. Each enzyme preparation was hybridized to the corresponding SNP array (262,000 and 238,000 on the NspI and StyI array respectively). The 93% call rate threshold at P=0.33 (dynamic Model algorithm confidence threshold) with the Dynamic Model algorithm 138 was used in individual assays.

To confirm whether human iPS-1-8 mTeSR cells were generated from fibroblasts (5F0438), we compared SNP genotyping between human iPS-1-8 mTeSR cells and the employed fibroblasts (Table 5). SNPs of human iPS-1-8 mTeSR cells were consistent to that of parental cells in 464,069 (99.17%) of 467,946 of called SNPs and different from that of parental cells in 3,877 (0.83%) of them. In contrast, SNPs of human iPS-1-8 mTeSR cells were consistent to that of unrelated donor cells (5F0416) only in 284,950 (60.50%) of 470,960 of called SNPs and different from that of the unrelated cells in 186,010 (39.50%) of them. Thus, human iPS-1-8 clone (1-8 mTeSR) and parental cells had almost the same SNP genotype each other, strongly suggesting that both cells were originated from a single donor.

HLA DNA typing was performed by utilizing hybridization of PCR-amplified DNA with sequence specific oligonucleotide probes (SSOP) (Luminex). Assays were performed to determine the HLA-A, HLA-B, HLA-Cw, HLA-DR, HLA-DQ, HLA-DP and Bw loci according to manufacturer's instructions. Human iPS cells are promising materials in cell transplantation therapies, they would overcome immune rejection, because human iPS cells can be directly generated from patients' cells and must be the identical HLA type. To actually prove the HLA issue, we carried out HLA typing of human iPS-1-8 clone (1-8 mTeSR), parental cells (5F0438), and unrelated fibroblasts (5F0416). As expected, HLA type of iPS-1-8 clone was completely identical to that of 5F0438 but not 5F0416 (Table 6).

From the foregoing, human pluripotent stem cell were obtained by the forced expression of each of four genes of Oct3/4, Sox2, Klf4, and c-Myc in undifferentiated stem cell present in a human postnatal tissue. The human pluripotent stem cells showed an in vitro long-term self-renewal ability and the pluripotency of differentiation into ectoderm, mesoderm and endoderm. The human pluripotent stem cells were expressed cell surface antigens SSEA-3, SSEA-4, TRA-1-60, TRA-1-81, CD9, CD24, and CD90, and ES cell marker genes Nanog, Oct3/4, TDGF1, Dnmt3b, GABRB3, GDF3, Zfp42, ALP, CD9, and Thy-1. The promoter regions of Nanog and Oct3/4 in the human pluripotent stem cells were demethylated compared to the parental fibroblasts. The human pluripotent stem cells carries at least a single copy of Oct3/4, Sox2, Klf4, and c-Myc transgene. The induced human pluripotent stem cells and the parental cells (undifferentiated stem cell present in a human postnatal tissue) had almost the same SNP genotype each other, and HLA type of the induced human pluripotent stem cell was completely identical to that of the parental cell (undifferentiated stem cell present in a human postnatal tissue).

Example 15. Gene Expression Profile of Primary Culture of 4 Genes Introduced Neonatal Fibroblast Two lots of neonatal fibroblasts (5F0416 and 5F0474) were seeded at $10^3$ cells/cm$^2$ or $10^4$ cells/cm$^2$ into 35 mm diameter wells of 6 well plates and cultured in FBM supplemented with FGM-2 SingleQuots (manufactured by Lonza) before the four genes transduction. Cells were infected with mCAT1-adenovirus vectors at $2 \times 10^5$ ifu/well and then infected with the retroviral vectors carrying four genes as described in Example 6. Eight wells were prepared for this study (2 different lot and 2 different densities in duplicate).

Seventeen days post 4-gene infection, cells were fixed and stained for alkaline phosphatase (ALP) as described in Example 3. In total, 163 ALP positive(+) colonies were observed in four independent experiments. All 163 ALP(+) colonies and 18 ALP-negative (ALP(−)) colonies were dissected, and total RNA from these colonies were extracted using a RecoverAll Total Nucleic Acid Isolation kit (manufactured by Ambion). After the cDNA preparation, genes of interest were amplified using Taqman preamp (manufactured by Applied Biosystems). Real-time quantitative PCR was performed with ABI PRISM 7900HT (manufactured by Applied Biosystems) using PCR primer sets (manufactured by Applied Biosystems, Nanog, Hs02387400_g1, Dnmt3b, Hs00171876_m1, FoxD3, Hs00255287_s1, Zfp42, Hs01938187_s1, TDGF1, Hs02339499_g1, TERT, Hs00162669_m1, GDF3, Hs00220998_m1, CYP26A1, Hs00175627_m1, GAPDH, Hs99999905_m1) to determine gene expression of human ES cell markers in colonies. Eight genes (Nanog, TDGF1, Dnmt3b Zfp42 FoxD3, GDF3, CYP26A1 and TERT genes) which were reported to express in human ES cells were selected as a pluripotent stem cell marker genes. A standard curves was generated for each primer pair. All expression values were normalized against GAPDH.

It is known that mouse ES cells and mouse iPS cells form multilayered/aggregated colonies. Thus we first analyzed the mouse ES cell like aggregated colonies which were induced by ectopic expression of four gene in human fibroblasts (e.g. colony #1-2-F and #1-2-B in FIG. 22). However, these colonies are all ALP(−). Next we analyzed the Nanog gene expression in colonies. Nanog gene expression was observed in 161 out of 163 ALP positive colonies and 16 out of 18 ALP negative colonies. On the other hand expression of TERT and CYP26A1 genes were observed only in 26 and 24 colonies out of 163 ALP positive colonies respectively (FIG. 15a). Genes such as Nanog, TDGF, and Dnmt3b which are well know to be close association with the pluripotent state in human ES cells, and to be strongly downregulated upon their differentiation had higher tendency to be induced by the four gene transduction.

ALP positive colonies can be categorized into 40 groups based on the gene expression pattern of the eight human marker genes (Table 7). When colonies are categorized by the total number of eight marker genes expression, the distribution of colony number followed a normal distribution suggesting the presence of a stochastic process in the colony induction (FIG. 15c,d). In addition the efficiency of human ES cell marker gene expression in human fibroblasts was affected by the donor difference.

Quantitative gene expression analysis of colonies formed 17 days after infection indicated that the transgenes c-Myc and Oct4 showed high expression in all the analyzed colonies (Table 11). In addition endogenous Nanog expression was very high in most of the ALP positive colonies, including cells lacking expression of one or more of the eight human ES cell marker genes (Table 11). These results indicate that the process of pluripotent stem cell induction from human skin fibroblasts is slower than that described for mouse iPS cell generation. Only 4 out of 163 ALP positive colonies were positive for Nanog, TDGF1, Dnmt3b, Zfp42, FoxD3, GDF3, Cyp26a1 and TERT (octa-positive colony). Cells in these octa-positive colonies showed common features: 1) small size with the high nucleus to cytoplasm ratio and 2) formation of small monolayer colonies within the space between fibroblasts (FIG. 15c). These features are consistent to the feature of human ES cells. However, these three features were also observed in some of ALP(+) colonies which lacked one or more ES cell marker expression. In addition, the large colony with these three features lack ALP expression (FIG. 22 colony #7-1-1). ALP (+) colonies with fibroblastic feature (colony #5-1-7, #3-1-214, #3-2-233, #3-1-212, #3-1-215, #5-1-4 in FIG. 16-22 and Table 7, 11) usually lacked one or more ES cell marker gene expressions.

These results indicate that induced pluripotent stem cells can be isolated from small monolayer colonies comprising small cells with high nucleus to cytoplasm ratio not from fibroblastic colonies, defused colonies or multilayered colonies. Table 8 summarizes all of experiments and results on the ALP positive colony number using human neonatal fibroblasts.

Example 16. Generation of Human iPS-2-4 Clone from Human Neonatal Skin Fibroblasts Adenovirus vector plasmids for mCAT1 were transfected into 29310 cells. The mCAT1-adenoviruses were isolated from these cells by three freeze-thaw cycles, purified using Adenovirus purification kit (Clontech) and stored at −80° C. The titer of the vector stocks was determined by Adeno-X rapid titer kit (Clontech).

The replication deficient MMLV derived retrovirus vector pMx was used for the ectopic expression of human Oct3/4, Sox-2, c-Myc and Klf4. Recombinant retroviruses were generated by transfecting vectors to the Plat-E packaging system (Morita et al., 2000) followed by incubation in FBM (Lonza) supplemented with FGM-2 SingleQuots (Lonza). Between 24 and 48 hours after the transfection, supernatant from the Plat-E culture was collected several times at intervals of at least 4 hours and passed through a 0.45 µm filter.

For MEF-conditioned medium (MEF-CM) preparation, human ES medium (DMEM/F12 (Gibco) supplemented with 20% Knockout Serum Replacement (KSR, Invitrogen), 2 mM L-glutamine (Sigma), 1× nonessential amino acids (Sigma), 10 µg/ml gentamycin), 10 ng/ml bFGF was conditioned on mitomycin-C treated MEF (Reprocell) for 20-24 hours, harvested, filtered through a 0.45 µm filter and supplemented with 0.1 mM 2-mercaptoethanol (Sigma) and 10 ng/ml bFGF before use.

Using cells (trade name: Neonatal Normal Human Skin Fibroblasts, primary culture) derived from a human neonatal tissue, a human tissue immediately after birth, the induction of human pluripotent stem cells from undifferentiated stem cells present in the skin of a human neonate was attempted.

Human neonatal dermal fibroblasts (Lonza; lot 5F0416) were cultured in FBM supplemented with FGM-2 Single- Quots. Three days before the 4 gene introduction, fibroblasts were seeded at $10^3$ cells/cm$^2$ into 6 well plates. Eighteen hours later, the cells were mixed with the mCAT1 adenovirus vector solution in 500 µl Hanks' balanced salt solution, and incubated at room temperature for 30 min. The cells were then added to 2 ml of medium and cultured for 48 hrs. Subsequently, the cells were incubated in 2 ml of the retrovirus/polybrene solution (mixture of equal volumes of the retrovirus vector suspension for each of the four genes (Oct3/4, Sox2, Klf4 and c-Myc) prepared in Example 1, supplemented with 5 µg/ml of polybrene) at 37° C. for 4 hrs to overnight. The virus supernatant was replaced with the MEF-conditioned ES medium. Then medium was changed every days.

On day 33 after gene introduction, a colony with a characteristic shape was picked with forceps from a well. The picked colony was transferred into a matigel-coated well in a 24-well plate and maintained in mTeSR defined medium supplemented with 10 µM Y-27632. Fourteen hours later the medium was changed. Medium change was continued every days. At day 54 after the infection a second culture was carried out. At day 67, human iPS-2-4 clone was sub-cloned and designated as human iPS-2-4 sub-clone.

For passaging, medium was removed, and the cells were washed with the Hank's balanced salt solution followed by the treatment with 0.25% trysin-EDTA at 37° C. for 3 minutes. Fresh medium was added to stop the reaction. The cell suspension was centrifuged at 4° C. and 200×g for 5 minutes, and the supernatant was removed. The cells were resuspended in mTeSR defined medium supplemented with 10 µM Y-27632 and plated.

Human iPS-2-4 sub-clone was successfully expanded in mTeSR1 defined medium (Stem cell Technologies) on matrigel (Invitrogen)-coated culture dishes. We termed cells derived from the sub-clone iPS-2-4 and cultured in mTeSR1 medium as human iPS-2-4 mTeSR cells. Medium was changed for human iPS-2-4 mTeSR cell culture everyday and usually treated with Y-27632 (Calbiochem) to avoid cell apoptosis after passaging. For passaging, cells were washed with Hanks's balanced solution, incubated in 0.25% trypsin-EDTA (Gibco) at 37° C. for 3 minutes, and then added the culture medium. Cells were centrifuged at 300×g at room temperature or 4° C. for 5 minutes and the supernatant was removed. The cells were re-suspended into culture medium. Human iPS-2-4 mTeSR cells were morphologically indistinguishable from typical human ES cells and human iPS-1-8 mTeSR cells consisting of small, round, and high nucleus to cytoplasm ratio cells with defined edges.

Fifty nine days post 4-gene infection, a part of cells were fixed and stained for alkaline phosphatase (ALP) as described in Example 3. Colonies consisting of cells were positive for ALP and Total RNA from colonies were extracted using a RecoverAll Total Nucleic Acid Isolation kit (manufactured by Ambion). After the cDNA preparation, genes of interest were amplified using Taqman preamp (manufactured by Applied Biosystems). Real-time quantitative PCR was performed with ABI PRISM 7900HT (manufactured by Applied Biosystems) using PCR primer sets (manufactured by Applied Biosystems, Nanog, Hs02387400_g1, Dnmt3b, Hs00171876_m1, FoxD3, Hs00255287_s1, Zfp42, Hs01938187_s1, TDGF1, Hs02339499_g1, TERT, Hs00162669_m1, GDF3, Hs00220998_m1, CYP26A1, Hs00175627_m1, GAPDH, Hs99999905_m1) to determine gene expression of human ES cell markers in colonies. Conle-2-4 showed ES cell marker gene expressions (Table 12).

From the above results, human pluripotent stem cell were obtained by the forced expression of each of four genes of Oct3/4, Sox2, Klf4, and c-Myc in undifferentiated stem cell present in a human postnatal tissue. The human pluripotent stem cells showed an in vitro long-term self-renewal ability, and were expressed ES cell marker genes Nanog, Oct3/4, TDGF1, Dnmt3b, GABRB3, GDF3, Zfp42, ALP, CD9, and Thy-1.

Example 17. Generation of Human iPS-3-2 Clone from Human Neonatal Skin Fibroblasts According to Example 16, human neonatal dermal fibroblasts (Lonza; lot 5F0438) were cultured in FBM supplemented with FGM-2 SingleQuots. Three days before the 4 gene introduction, fibroblasts were seeded at $10^3$ cells/cm$^2$ into 6 well plates. Eighteen hours later, the cells were mixed with the mCAT1 adenovirus vector solution in 500 µl Hanks' balanced salt solution, and incubated at room temperature for 30 min. The cells were then added to 2 ml of medium and cultured for 48 hrs. Subsequently, the cells were incubated in 2 ml of the retrovirus/polybrene solution (mixture of equal volumes of the retrovirus vector suspension for each of the four genes (Oct3/4, Sox2, Klf4 and c-Myc) prepared in Example 1, supplemented with 5 µg/ml of polybrene) at 37° C. for 4 hrs to overnight. The virus supernatant was replaced with the MEF-conditioned ES medium. Then medium was changed every days. On day 21 after gene introduction, a colony with a characteristic shape was directly picked with forceps from one of dishes. The picked colony was transferred into a matigel-coated well in a 24-well plate and maintained in mTeSR defined medium supplemented with 10 µM Y-27632.

Fourteen hours later the medium was changed. Medium change was continued every days. 40 days after the infection, a second subcloning was carried out, and cells were successfully expanded in mTeSR1 defined medium (Stem cell Technologies) on matrigel (Invitrogen)-coated culture dishes. Medium was changed everyday and usually treated with Y-27632 (Calbiochem) to avoid cell apoptosis after passaging. For passaging, cells were washed with Hanks's balanced solution, incubated in 0.25% trypsin-EDTA (Gibco) at 37° C. for 5 minutes, and then added the culture medium. Cells were centrifuged at 300×g at room temperature for 5 minutes and the supernatant was removed. The cells were re-suspended into culture medium.

Cells were morphologically indistinguishable from typical human ES cells, human iPS-1-8 mTeSR cells, and human iPS-2-4 mTeSR cells that consist of small, round, and high nucleus to cytoplasm ratio cells with defined edges. Thus we termed this clone as human iPS-3-2 clone. Human iPS-3-2 clone actively proliferated in mTeSR1 medium. We termed these cells derived from human iPS-3-2 clone which culture in mTeSR1 medium as human iPS-3-2 mTeSR cells.

Forty eight days post 4-gene infection, cells were fixed and stained for alkaline phosphatase (ALP) as described in Example 3. Total RNA from colonies were extracted using a RecoverAll Total Nucleic Acid Isolation kit (manufactured by Ambion). After the cDNA preparation, genes of interest were amplified using Taqman preamp (manufactured by Applied Biosystems). Real-time quantitative PCR was performed with ABI PRISM 7900HT (manufactured by Applied Biosystems) using PCR primer sets (manufactured by Applied Biosystems, Nanog, Hs02387400_g1, Dnmt3b, Hs00171876_m1, FoxD3, Hs00255287_s1, Zfp42, Hs01938187_s1, TDGF1, Hs02339499_g1, TERT, Hs00162669_m1, GDF3, Hs00220998_m1, CYP26A1, Hs00175627_m1, GAPDH, Hs99999905_m1) to determine gene expression of human ES cell markers in colonies. Conle-3-2 showed ES cell marker gene expressions (Table 12).

From the above results, human pluripotent stem cell were obtained by the forced expression of each of four genes of Oct3/4, Sox2, Klf4, and c-Myc in undifferentiated stem cell present in a human postnatal tissue. The human pluripotent stem cells showed an in vitro long-term self-renewal ability, and were expressed ES cell marker genes Nanog, Oct3/4, TDGF1, Dnmt3b, GABRB3, GDF3, Zfp42, ALP, CD9, and Thy-1.

Table 1 shows the name of gene, the NCBI number, the virus vector in which said gene was inserted, insert size, the restriction site at the 5'-end, the restriction site at the 3'-end, the length of the translated region, the length of the 3'-untranslated region, clone ID, and the supplier of the four genes or the three genes and the receptor of mouse ecotropic retrovirus vector (mCAT: mouse-derived cationic amino acid transporter) used in Examples.

TABLE 1

Construction data

| Name of gene | NCBI No. | Gene-inserted virus vector | Insert size | 5'-end restriction site | 3'-end restriction site | Length of translated region | 3'-untranslated region | Clone ID | Supplier |
|---|---|---|---|---|---|---|---|---|---|
| human Oct3/4 | NM_002701 | pMXs-puro | 1411 | EcoRI | Xho1 | 1083 | 274 | 6578897 | Open Biosystems |
| human Sox2 | BC013923 | pMXs-neo | 1172 | EcoRI | Xho1 | 954 | 143 | 2823424 | Open Biosystems |
| human c-Myc | BC058901 | pMXs-IB | 1876 | EcoRI | Xho1 | 1365 | 473 | 6012670 | Open Biosystems |
| human Klf4 | BC029923 | pMXs-IB | 1591 | EcoRI | EcoRI | 1413 | 38 | 5111134 | Open Biosystems |
| mCAT1 | NM_007513 | Adeno-X | 2032 | BssS1 | BssS1 | 1869 | 132 | A830015N05 | RIKEN FANTOM clone |

Table 2 summarizes the number of alkaline phosphatase-positive colonies of Examples 4 to 7. For cell type, the number of subculture is attached. The day of four gene introduction is a day when a retrovirus vector was infected. Lot No. is that of Lonza products. Age of donors is based on the donor information of Lonza products. The number of colonies is the number of colonies composed of alkaline phosphatase-positive small cells per 10 cm$^2$.

TABLE 2

Examples 5 to 8 and 10, Number of alkaline phosphatase (ALP)-positive colonies formed by gene introduction

| Example | Cell type | Donor age | Lot No. | Serum concentration (%) | No. of passages at the time of gene introduction | Date of gene introduction | Date of ALP staining | Colony count* |
|---|---|---|---|---|---|---|---|---|
| 8 | Neonatal skin fibroblast | Neonate | 5F0439 | 2 | 3 | 2007 Mar. 20 | 2007 Apr. 3 | 0.8 |
| 6 | Neonatal skin fibroblast | Neonate | 5F0438 | 2 | 2 | 2007 Apr. 15 | 2007 Apr. 29 | 6.0 |
| 6 | Neonatal skin fibroblast | Neonate | 5F0438 | 2 | 2 | 2007 May 5 | 2007 May 16 | 6.0 |
| 6 | Neonatal skin fibroblast | Neonate | 5F0474 | 2 | 2 | 2007 May 5 | 2007 May 16 | 4.0 |
| 6 | Neonatal skin fibroblast | Neonate | 5F0438 | 2 | 2 | 2007 May 12 | 2007 May 26 | 7.0 |
| 6 | Neonatal skin fibroblast | Neonate | 5F0474 | 2 | 2 | 2007 May 12 | 2007 May 26 | 9.5 |
| 7 | Adult skin fibroblast | 28 | 6F3535 | 2 | 2 | 2007 May 5 | 2007 May 16 | 2.0 |
| 7 | Adult skin fibroblast | 39 | 6F4026 | 2 | 2 | 2007 May 5 | 2007 May 16 | 0.0 |
| 5 | Adult BM-derived cell (low serum) | 20 | 060470B | 2 | 2 | 2007 Mar. 20 | 2007 Apr. 3 | 0.0 |
| 5 | Adult BM-derived cell (low serum) | 20 | 060809B | 2 | 2 | 2007 Mar. 26 | 2007 Apr. 9 | 0.0 |
| 5 | Adult BM-derived cell (low serum) | 20 | 060809B | 2 | 2 | 2007 Apr. 15 | 2007 Apr. 29 | 0.2 |
| 5 | Adult BM-derived cell (low serum) | 20 | 060809B | 2 | 2 | 2007 May 5 | 2007 May 19 | 0.0 |
| 5 | Adult BM-derived mesenchymal stem cell (high serum) | 20 | 060809B | 10 | 2 | 2007 Mar. 20 | 2007 Apr. 3 | 0.0 |
| 5 | Adult BM-derived mesenchymal stem cell (high serum) | 20 | 060470B | 10 | 2 | 2007 Mar. 26 | 2007 Apr. 9 | 0.0 |
| 10 | Neonatal umbilical cord artery smooth muscle cell | Neonate | 5F0442 | 5 | 4 | 2007 May 11 | 2007 May 24 | 0.0 |

*The number of colonies composed of alkaline phosphatase-positive small cells per 10 cm$^2$.
"BM" in Table 2 means "Bone Marrow".

Table 3 summarizes the distribution of the karyotype of clone 1-8 at day 101. After the Giemsa stain, chromosome numbers were counted. 67 of 100 cells showed normal karyotype.

TABLE 3

| karyotype analysis | |
|---|---|
| Chromosome no. | Cell no |
| 44 | 1 |
| 45 | 22 |

TABLE 3-continued

| karyotype analysis | |
|---|---|
| Chromosome no. | Cell no |
| 46 | 67 |
| 47 | 7 |
| 48 | 1 |
| 89 | 1 |
| 136 | 1 |

One hundred cells were analyzed in human iPS cells (clone 1-8mTeSR)

Table 4 shows primer sequences used in FIG. 6 and FIG. 14.

TABLE 4

| Primer Sequences for RT-PCR | | |
|---|---|---|
| | Forward primer sequence | Reverse primer sequence |
| HPRT | AGTCTGGCTTATATCCAACACTTCG | GACTTTGCTTTCCTTGGTCAGG |
| Nanog | TACCTCAGCCTCCAGCAGAT | TGCGTCACACCATTGCTATT |
| TERT | AGCCAGTCTCACCTTCAACCGC | GGAGTAGCAGAGGGAGGCCG |
| Sall4 | AAACCCCAGCACATCAACTC | GTCATTCCCTGGGTGGTTC |
| Zfp42 | TTGGAGTGCAATGGTGTGAT | TCTGTTCACACAGGCTCCAG |
| GDF3 | GGCGTCCGCGGGAATGTACTTC | TGGCTTAGGGGTGGTCTGGCC |
| Dnmt3b | GCAGCGACCAGTCCTCCGACT | AACGTGGGGAAGGCCTGTGC |
| TDGF1 | ACAGAACCTGCTGCCTGAAT | AGAAATGCCTGAGGAAAGCA |
| GABRB3 | CTTGACAATCGAGTGGCTGA | TCATCCGTGGTGTAGCCATA |
| CYP26A1 | AACCTGCACGACTCCTCGCACA | AGGATGCGCATGGCGATTCG |
| Oct4-total | GAGAAGGAGAAGCTGGAGCA | AATAGAACCCCCAGGGTGAG |
| Oct4-exo | AGTAGACGGCATCGCAGCTTGG | GGAAGCTTAGCCAGGTCCGAGG |
| Sox2-total | CAGGAGAACCCCAAGATGC | GCAGCCGCTTAGCCTCG |
| Sox2-exo | ACACTGCCCCTCTCACACAT | CGGGACTATGGTTGCTGACT |
| Klf4-total | ACCCTGGGTCTTGAGGAAGT | ACGATCGTCTTCCCCTCTTT |
| Klf4-exo | CTCACCCTTACCGAGTCGGCG | GCAGCTGGGGCACCTGAACC |
| c-Myc-total | TCCAGCTTGTACCTGCAGGATCTGA | CCTCCAGCAGAAGGTGATCCAGACT |
| c-Myc-exo | AGTAGACGGCATCGCAGCTTGG | CCTCCAGCAGAAGGTGATCCAGACT |

Table 5 summarizes SNP genotyping of human iPS clone 1-8 and fibroblasts (5F0438 and 5F04156) which were analyzed using the GeneChip Human Mapping 500K Array Set. SNPs of clone 1-8 were consistent to that of parental cells in 464,069 (99.17%) of 467,946 of called SNPs and different from that of parental cells in 3,877 (0.83%) of them. In contrast, SNPs of clone 1-8 mTeSR were consistent to that of unrelated donor cells (5F0416) only in 284,950 (60.50%) of 470,960 of called SNPs and different from that of the unrelated cells in 186,010 (39.50%) of them.

TABLE 5

| SNP genotyping | | |
|---|---|---|
| 500K_Set Number of total SNP | 500,568 | |
| Number of called SNP | | |
| human iPS-1-8 | 484,393 | 96.77% |
| neoFB (5F0438) | 480,249 | 95.94% |
| neoFB (5F0416) | 485,626 | 97.01% |

TABLE 5-continued

| SNP genotyping | | |
|---|---|---|
| human iPS-1-8 vs. neoFB (5F0438) | | |
| Called SNP in both samples | 467,946 | ratio |
| Consistent SNP | 464,069 | 99.17% |
| different SNP | 3,877 | 0.83% |
| No called SNP in neither | 32,622 | |
| human iPS-1-8 vs. neoFB (5F0416) | | |
| Called SNP in both samples | 470,960 | ratio |
| Consistent SNP | 284,950 | 60.50% |
| different SNP | 186,010 | 39.50% |
| No called SNP in neither | 29,608 | |

Table 6 The HLA-A, HLA-B, HLA-Cw and HLA-DR types of human iPS1-8 (1-8 mTeSR) and fibroblasts (5F0438 and 5F0416) were classified using hybridization of PCR-amplified DNA with sequence specific oligonucleotide probes (SSOP) (Luminex).

TABLE 6

| HLA genotyping | | | | | | | | | | | | |
|---|---|---|---|---|---|---|---|---|---|---|---|---|
| ID | A allele | | B allele | | Cw allele | | DRB1 allele | | DQB1 allele | | DPB1 allele | |
| 5F0438 | *0101/ | *0206/ | *3801/09 | *3905 | *0602/ | *0702/ | *0802 | *1104/43/ | *0301/ | *0402 | *0402/ | *0501 |
| 5F0416 | *0201/ | — | *1501/ | *5101/ | *0303/ | *0401/ | *0401/33/38 | *0801/26 | *0302/ | *0402 | *0201 | *0301/ |
| 1-8(5F0438) | *0101/ | *0206/ | *3801/09 | *3905 | *0602/ | *0702/ | *0802 | *1104/43/ | *0301/ | *0402 | *0402/ | *0501 |

| ID | HLA-A | | HLA-B | | HLA-Cw | | HLA-DR | | HLA-DQ | | HLA-DP | | Bw |
|---|---|---|---|---|---|---|---|---|---|---|---|---|---|
| 5F0438 | A1 | A2 | B38 | B39 | Cw6 | Cw7 | DR8.2 | DR11 | DQ7 | DQ4 | DP4 | DP5 | 4/6 |
| 5F0416 | A2 | — | B62 | B51 | Cw9 | Cw4 | DR4.1 | DR8.1 | DQ8 | DQ4 | DP2 | DP3 | 4/6 |
| 1-8(5F0438) | A1 | A2 | B38 | B39 | Cw6 | Cw7 | DR8.2 | DR11 | DQ7 | DQ4 | DP4 | DP5 | 4/6 |

Table 7 summarized hES cell marker gene expression patterns in colonies. Colonies were stained for alkaline phosphatase at 17 days post 4 genes transduction. All ALP(+) colonies and 18 ALP(−) colonies were dissected and determined their hES marker gene expression by RT-PCR. Each colony was categorized and counted the number. "+" represents gene expression, and "−" represents no detection by a 40 cycle RT-PCR using amplified cDNA samples.

TABLE 7

| Gene expression patterns in ALP(+) and ALP(−) colonies | | | | | | | | | | |
|---|---|---|---|---|---|---|---|---|---|---|
| Group No. | No. of gene expressed | Nanog | TDGF1 | Dnmt3b | Zfp42 | FoxD3 | GDF3 | CYP26A1 | TERT | No. of colony |
| Gene expression patterns in ALP(+) colonies | | | | | | | | | | |
| 1 | 8 | + | + | + | + | + | + | + | + | 4 |
| 2 | 7 | + | + | + | + | + | + | + | − | 7 |
| 3 | 7 | + | + | + | + | + | + | − | + | 11 |
| 4 | 7 | + | + | + | + | + | − | + | + | 1 |
| 5 | 6 | + | + | + | + | + | + | − | − | 25 |
| 6 | 6 | + | + | + | + | + | − | + | − | 4 |
| 7 | 6 | + | + | + | + | + | − | − | + | 3 |
| 8 | 6 | + | + | + | + | − | + | − | + | 2 |
| 9 | 6 | + | + | + | + | − | + | + | − | 3 |
| 10 | 6 | + | + | + | − | + | + | + | − | 1 |
| 11 | 6 | + | + | + | − | + | + | + | + | 1 |
| 12 | 5 | + | + | + | + | + | − | − | − | 22 |
| 13 | 5 | + | + | + | + | − | + | − | − | 9 |
| 14 | 5 | + | + | + | + | − | − | + | − | 2 |
| 15 | 5 | + | + | + | − | + | + | − | − | 4 |
| 16 | 5 | + | + | + | − | + | − | + | − | 2 |
| 17 | 5 | + | + | + | − | − | + | + | − | 1 |

TABLE 7-continued

Gene expression patterns in ALP(+) and ALP(-) colonies

| Group No. | No. of gene expressed | Nanog | TDGF1 | Dnmt3b | Zfp42 | FoxD3 | GDF3 | CYP26A1 | TERT | No. of colony |
|---|---|---|---|---|---|---|---|---|---|---|
| 18 | 5 | + | + | − | + | + | + | − | − | 2 |
| 19 | 5 | + | + | − | + | + | − | − | + | 1 |
| 20 | 4 | + | + | + | + | − | − | − | − | 9 |
| 21 | 4 | + | + | + | − | + | − | − | − | 3 |
| 22 | 4 | + | + | + | − | − | + | − | − | 5 |
| 23 | 4 | + | + | − | + | + | − | − | − | 7 |
| 24 | 4 | + | − | + | + | + | − | − | − | 1 |
| 25 | 4 | + | − | + | − | + | + | − | − | 2 |
| 26 | 4 | + | − | − | + | + | + | − | − | 1 |
| 27 | 3 | + | + | + | − | − | − | − | − | 1 |
| 28 | 3 | + | + | − | + | − | − | − | − | 3 |
| 29 | 3 | + | + | − | − | + | − | − | − | 4 |
| 30 | 3 | + | + | − | − | − | − | − | + | 1 |
| 31 | 3 | + | − | + | + | − | − | − | − | 1 |
| 32 | 3 | + | − | + | − | + | − | − | − | 2 |
| 33 | 3 | + | − | + | − | − | + | − | − | 1 |
| 34 | 3 | + | − | − | + | + | − | − | − | 1 |
| 35 | 3 | + | − | − | − | + | + | − | − | 1 |
| 36 | 2 | + | + | − | − | − | − | − | − | 4 |
| 37 | 2 | + | − | + | − | − | − | − | − | 5 |
| 38 | 2 | + | − | − | + | − | − | − | − | 2 |
| 39 | 1 | + | − | − | − | − | − | − | − | 2 |
| 40 | 0 | − | − | − | − | − | − | − | − | 2 |
| Gene expression patterns in ALP(−) colonies | | | | | | | | | | |
| 41 | 6 | + | + | + | + | + | − | + | − | 1 |
| 42 | 6 | + | + | − | + | + | + | − | + | 1 |
| 43 | 5 | + | + | + | + | + | − | − | − | 3 |
| 44 | 5 | + | + | − | + | + | − | − | + | 6 |
| 45 | 4 | + | + | + | − | + | − | − | − | 1 |
| 46 | 4 | + | + | − | + | + | − | − | − | 1 |
| 47 | 4 | + | + | + | − | − | − | − | + | 1 |
| 48 | 2 | + | − | − | − | − | − | − | + | 1 |
| 49 | 1 | + | − | − | − | − | − | − | − | 1 |
| 50 | 1 | − | + | − | − | − | − | − | − | 1 |
| 51 | 0 | − | − | − | − | − | − | − | − | 1 |

Table 8 summarizes the number of alkaline phosphatase-positive colonies of the experiments using neonatal fibroblasts. The date of four gene introduction is a day when a retrovirus vector was infected. The donor indicates lot number of Lonza products. The number of colonies is the number of colonies composed of alkaline phosphatase-positive small cells per 10 cm$^2$. ND: not determined.

TABLE 8

List of experiments

| experimental conditions | | | ALP staining | | |
|---|---|---|---|---|---|
| date of 4 gene transduction | donor | cell density (cell/cm$^2$) | date | number of colony (/10 cm$^2$) | notes |
| 2007 Mar. 20 | 5F0439 | 1 × 10$^4$ | 2007 Apr. 3 | 0.8 | |
| 2007 Apr. 15 | 5F0438 | 1 × 10$^4$ | 2007 Apr. 29 | 6.0 | iPS clone#1-8 |
| 2007 May 5 | 5F0438 | 1 × 10$^4$ | 2007 May 16 | 6.0 | |
| | 5F0474 | 1 × 10$^4$ | | 4.0 | |
| 2007 May 12 | 5F0438 | 1 × 10$^4$ | 2007 May 26 | 7.0 | |
| | 5F0474 | 1 × 10$^4$ | | 9.5 | |
| 2007 May 26 | 5F0474 | 1 × 10$^4$ | 2007 Jun. 9 | 13.3 | |
| 2007 Jun. 8 | 5F0416 | 1 × 10$^3$ | 2007 Jun. 22 | 19.0 | |
| | 5F0416 | 1 × 10$^4$ | | 17.5 | |
| | 5F0474 | 1 × 10$^4$ | | 14.0 | |
| 2007 Jul. 20 | 5F0416 | 1 × 10$^3$ | 2007 Aug. 6 | 3.0 | |
| | 5F0416 | 1 × 10$^4$ | | 9.0 | |

TABLE 8-continued

List of experiments

| experimental conditions | | | ALP staining | | |
|---|---|---|---|---|---|
| date of 4 gene transduction | donor | cell density (cell/cm$^2$) | date | number of colony (/10 cm$^2$) | notes |
| 2007 Aug. 10 | 5F0416 | $1 \times 10^3$ | 2007 Aug. 27 | 21.0 | ALP(+) colony classification |
| | 5F0416 | $1 \times 10^4$ | | 21.5 | |
| | 5F0474 | $1 \times 10^3$ | | 17.0 | |
| | 5F0474 | $1 \times 10^4$ | | 19.5 | |
| 2007 Aug. 17 | 5F0416 | $1 \times 10^3$ | | ND | iPS clone #2-4 |
| | 5F0416 | $1 \times 10^4$ | | ND | |
| | 5F0474 | $1 \times 10^3$ | | ND | |
| | 5F0474 | $1 \times 10^4$ | | ND | |
| 2007 Aug. 31 | 5F1195 | $1 \times 10^3$ | | ND | |
| 2007 Sep. 14 | 5F0438 | $1 \times 10^3$ | | ND | iPS clone #3-2 |

Table 9 lists up locations and sizes in genome corresponding to amplicons using for methylation analyses of the promoter regions of Nanog and Oct3/4. Columns A, B and C indicate amplicon name, locations and sizes in genome corresponding to amplicons, respectively.

TABLE 9

Promoter regions in methylation analysis

| amplicon name | location in genome corresponding to amplicon | size of amplicon |
|---|---|---|
| Nanog-z1 | chr12: 7832645-7832959 | 315 |
| Nanog-z2 | chr12: 7832877-7833269 | 393 |
| Oct3/4-z1 | chr6: 31248581-31249029 | 449 |
| Oct3/4-z2 | chr6_qbl_hap2: 2388299-2388525 | 227 |

Table 10 lists up the primer sets using for methylation analyses of the promoter regions of Nanog and Oct3/4. Columns A and B indicate names of primers and sequences of primers (capital for gene-specific sequences, lower case for tag sequences), respectively.

TABLE 10

Primer sequences for methylation analyses

| names of primers | sequences of primers (capital for gene-specific sequences, lower case for tag sequences) |
|---|---|
| Nanog-z1-L | aggaagagagGGAATTTAAGGTGTATGTATTTTTATTTT cagtaatacgactcactatagggagaaggctATAACCCACCCCTATAATC |
| Nanog-z1-R | CCAATA |
| Nanog-z2-L | aggaagagagGTTAGGTTGGTTTTAAATTTTTGAT cagtaatacgactcactatagggagaaggctTTTATAATAAAAACTCTAT |
| Nanog-z2-R | CACCTTAAACC |
| Oct3/4-z1-L | aggaagagagTAGTAGGGATTTTTTGGATTGGTTT cagtaatacgactcactatagggagaaggctAAAACTTTTCCCCCACTCT |
| Oct3/4-z1-R | TATATTAC |
| Oct3/4-z2-L | aggaagagagGGTAATAAAGTGAGATTTTGTTTTAAAAA cagtaatacgactcactatagggagaaggctCCACCCACTAACCTTAACC |
| Oct3/4-z2-R | TCTAA |

Table 11 summarizes relative mRNA expression in ALP positive colonies of Examples 15. Numbers of colonies are corresponding to FIG. 15-22. Colony #5-2-32, #5-2-49, #5-2-51, #7-2-37 expressed all analyzed human ES cell markers. In contrast, fibroblastic colonies #3-1-212, #3-1-215, #5-1-4 expressed only Nanog though it highly expressed transgenes.

TABLE 11

Relative mRNA expression of ES cell markers in ALP positive colonies

| Group | Sample | ALP | Nanog mean | | SD | GDF3 mean | | SD | CYP26A1 mean | | SD | TERT mean | | SD | Myc mean | | SD | Oct4 mean | | SD |
|---|---|---|---|---|---|---|---|---|---|---|---|---|---|---|---|---|---|---|---|---|
|  | iPS 1-8 | ALP(+) | 1.0 | | | 1.0 | | | 1.0 | | | 1.0 | | | 1.0 | | | 1.0 | | |
| 1 | #5-2-32 | ALP(+) | 9.3 | ± | 1.5 | 4.8 | ± | 0.3 | 27.2 | ± | 12.5 | 0.2 | ± | 0.0 | 1121.1 | ± | 25.3 | 39.3 | ± | 1.5 |
| 1 | #5-2-49 | ALP(+) | 15.9 | ± | 5.7 | 242.9 | ± | 78.8 | 3.0 | ± | 0.3 | 3.7 | ± | 0.5 | 1106.3 | ± | 51.8 | 770.6 | ± | 9.3 |
| 1 | #5-2-51 | ALP(+) | 27.1 | ± | 2.2 | 419.2 | ± | 24.7 | 73.5 | ± | 8.2 | 2.5 | ± | 0.1 | 1329.4 | ± | 272.1 | 101.6 | ± | 5.1 |
| 1 | #7-2-37 | ALP(+) | 36.9 | ± | 7.8 | 171.3 | ± | 20.0 | 110.1 | ± | 15.4 | 6.2 | ± | 1.1 | 566.9 | ± | 22.1 | 30.9 | ± | 2.4 |
| 3 | #1-1-5 | ALP(+) | 21.0 | ± | 2.4 | 59.2 | ± | 10.2 | 0.0 | ± | 0.0 | 0.12 | ± | 0.09 | 436 | ± | 12 | 25.0 | ± | 1.2 |
| 3 | #1-1-11 | ALP(+) | 127.6 | ± | 6.0 | 259.7 | ± | 3.9 | 0.0 | ± | 0.0 | 0.6 | ± | 0.3 | 59.2 | ± | 1.2 | 9.1 | ± | 0.1 |
| 3 | #1-1-19 | ALP(+) | 32.6 | ± | 8.4 | 34.0 | ± | 5.0 | 0.0 | ± | 0.0 | 1.1 | ± |  | 446.9 | ± | 15.8 | 14.9 | ± | 0.1 |
| 3 | #1-2-28 | ALP(+) | 9.5 | ± | 1.0 | 3.4 | ± | 0.9 | 0.0 | ± | 0.0 | 1.6 | ± | 0.1 | 1052.8 | ± | 129.5 | 17.1 | ± | 0.3 |
| 3 | #3-1-218 | ALP(+) | 141.5 | ± | 64.3 | 328.8 | ± | 54.1 | 0.0 | ± | 0.0 | 7.0 | ± | 0.7 | 9796.2 | ± | 275.5 | 324.2 | ± | 29.8 |
| 3 | #3-2-226 | ALP(+) | 78.0 | ± | 16.6 | 188.2 | ± | 3.8 | 0.0 | ± | 0.0 | 67.6 | ± | 7.1 | 9714.4 | ± | 15.7 | 258.7 | ± | 13.3 |
| 3 | #5-2-41 | ALP(+) | 55.5 | ± | 12.2 | 151.3 | ± | 21.2 | 0.0 | ± | 0.0 | 5.2 | ± | 0.1 | 285.3 | ± | 49.6 | 24.8 | ± | 3.2 |
| 3 | #5-2-44 | ALP(+) | 0.1 | ± | 0.1 | 0.1 | ± | 0.1 | 0.0 | ± | 0.0 | 1.1 | ± | 0.0 | 13065.1 | ± | 769.8 | 241.8 | ± | 0.7 |
| 3 | #5-2-46 | ALP(+) | 10.9 | ± | 2.6 | 67.9 | ± | 12.3 | 0.0 | ± | 0.0 | 4.4 | ± | 0.8 | 171.5 | ± | 2.3 | 578.7 | ± | 13.4 |
| 3 | #5-2-50 | ALP(+) | 0.1 | ± | 0.0 | 0.4 | ± | 0.1 | 0.0 | ± | 0.0 | 0.7 | ± | 0.5 | 3176.2 | ± | 751.2 | 233.4 | ± | 17.7 |
| 3 | #7-2-26 | ALP(+) | 51.5 | ± | 14.4 | 126.4 | ± | 1.1 | 0.0 | ± | 0.0 | 2.5 | ± | 0.3 | 1446.0 | ± | 421.7 | 33.8 | ± | 2.6 |
| 4 | #5-1-2 | ALP(+) | 0.7 | ± | 0.1 | 0.0 | ± | 0.0 | 5.0 | ± |  | 0.5 | ± | 0.2 | 6049.2 | ± | 396.9 | 3.8 | ± | 0.3 |
| 7 | #3-2-227 | ALP(+) | 14.6 | ± | 1.1 | 0.0 | ± | 0.0 | 0.0 | ± | 0.0 | 40.0 | ± | 5.7 | 27086.4 | ± | 3870.8 | 530.6 | ± | 84.1 |
| 7 | #5-1-13 | ALP(+) | 20.1 | ± | 5.9 | 0.0 | ± | 0.0 | 0.0 | ± | 0.0 | 1.9 | ± | 1.0 | 9125.8 | ± | 883.7 | 7.5 | ± | 0.7 |
| 7 | #7-2-31 | ALP(+) | 1.1 | ± | 0.4 | 0.0 | ± | 0.0 | 0.0 | ± | 0.0 | 20.6 | ± | 0.6 | 8344.9 | ± | 2054.5 | 6.7 | ± | 0.5 |
| 8 | #3-1-210 | ALP(+) | 103.4 | ± | 11.7 | 195.3 | ± | 17.7 | 0.0 | ± | 0.0 | 18.1 | ± | 1.8 | 95692.9 | ± | 5109.8 | 2843.9 | ± | 113.9 |
| 8 | #3-1-211 | ALP(+) | 50.8 | ± | 3.6 | 291.3 | ± | 43.9 | 0.0 | ± | 0.0 | 20.2 | ± | 2.9 | 29701.1 | ± | 4821.3 | 483.1 | ± | 13.9 |
| 11 | #1-1-20 | ALP(+) | 50.3 | ± | 14.5 | 34.3 | ± | 3.6 | 10.4 | ± | 2.0 | 1.3 | ± | 0.1 | 533.8 | ± | 24.8 | 30.2 | ± | 1.2 |
| 12 | #5-1-20 | ALP(+) | 9.3 | ± | 0.5 | 0.0 | ± | 0.0 | 0.0 | ± | 0.0 | 0.0 | ± | 0.0 | 16848.2 | ± | 1742.0 | 4.7 | ± | 0.2 |
| 19 | #3-2-233 | ALP(+) | 126.4 | ± | 65.3 | 0.0 | ± | 0.0 | 0.0 | ± | 0.0 | 28.7 | ± | 4.9 | 23614.4 | ± | 388.9 | 310.9 | ± | 19.2 |
| 23 | #5-1-16 | ALP(+) | 3.7 | ± | 1.3 | 0.0 | ± | 0.0 | 0.0 | ± | 0.0 | 0.0 | ± | 0.0 | 2927.9 | ± | 412.5 | 130.3 | ± | 10.1 |
| 23 | #5-1-18 | ALP(+) | 1.9 | ± | 0.3 | 0.0 | ± | 0.0 | 0.0 | ± | 0.0 | 0.0 | ± | 0.0 | 19433.2 | ± | 297.0 | 4.2 | ± | 0.5 |
| 23 | #7-2-46 | ALP(+) | 17.4 | ± | 5.1 | 0.0 | ± | 0.0 | 0.0 | ± | 0.0 | 0.0 | ± | 0.0 | 1959.8 | ± | 379.9 | 8.5 | ± | 0.7 |
| 28 | #3-1-215 | ALP(+) | 2.2 | ± | 0.3 | 0.0 | ± | 0.0 | 0.0 | ± | 0.0 | 0.0 | ± | 0.0 | 6065.6 | ± | 704.9 | 3.4 | ± | 0.3 |
| 29 | #3-1-212 | ALP(+) | 1.9 | ± | 0.3 | 0.0 | ± | 0.0 | 0.0 | ± | 0.0 | 0.0 | ± | 0.0 | 4572.6 | ± | 303.7 | 7.4 | ± | 0.1 |
| 29 | #5-1-4 | ALP(+) | 1.4 | ± | 0.2 | 0.0 | ± | 0.0 | 0.0 | ± | 0.0 | 0.0 | ± | 0.0 | 53755.3 | ± | 10897.7 | 22.9 | ± | 3.0 |
| 30 | #3-2-228 | ALP(+) | 5.6 | ± | 2.9 | 0.0 | ± | 0.0 | 0.0 | ± | 0.0 | 807.1 | ± | 13.4 | 25595.8 | ± | 2002.8 | 414.9 | ± | 22.6 |
| 42 | #305-2-28 | ALP(−) | 0.5 | ± | 0.1 | 0.1 | ± |  | 0.0 | ± | 0.0 | 0.0 | ± | 0.0 | 5873.2 | ± | 156.2 | 226.3 | ± | 12.9 |
| 44 | #5-1-3 | ALP(−) | 0.8 | ± | 0.2 | 0.0 | ± | 0.0 | 1.6 | ± | 0.3 | 0.5 | ± | 0.2 | 8698.4 | ± | 492.3 | 58.7 | ± | 2.6 |

TABLE 11-continued

Relative mRNA expression of ES cell markers in ALP positive colonies

| Group | Sample | ALP | Nanog mean | | SD | GDF3 mean | | SD | CYP26A1 mean | | SD | TERT mean | | SD | Myc mean | | SD | Oct4 mean | | SD |
|---|---|---|---|---|---|---|---|---|---|---|---|---|---|---|---|---|---|---|---|---|
| 44 | #5-1-23 | ALP(−) | 6.9 | ± | 1.1 | 0.0 | ± | 0.0 | 0.0 | ± | 0.0 | 0.7 | ± | 0.1 | 9350.1 | ± | 201.0 | 2.1 | ± | 0.1 |
| 44 | #5-1-24 | ALP(−) | 7.2 | ± | 2.0 | 0.0 | ± | 0.0 | 0.0 | ± | 0.0 | 7.3 | ± | 1.8 | 26133.6 | ± | 3528.5 | 8.0 | ± | 0.1 |
| 44 | #5-2-25 | ALP(−) | 0.2 | ± | 0.1 | 0.0 | ± | 0.0 | 0.0 | ± | 0.0 | 0.5 | ± | 0.1 | 5211.8 | ± | 618.7 | 370.7 | ± | 7.8 |
| 44 | #5-2-36 | ALP(−) | 2.5 | ± | 0.5 | 0.0 | ± | 0.0 | 0.0 | ± | 0.0 | 0.5 | ± | 0.1 | 8971.8 | ± | 110.3 | 266.6 | ± | 21.4 |
| 44 | #7-2-40 | ALP(−) | 3.4 | ± | 0.9 | 0.0 | ± | 0.0 | 0.0 | ± | 0.0 | 11.8 | ± | 3.4 | 9748.3 | ± | 530.0 | 7.3 | ± | 0.1 |
| 47 | #7-1-21 | ALP(−) | 0.2 | ± | 0.1 | 0.0 | ± | 0.0 | 0.0 | ± | 0.0 | 14.6 | ± | 1.9 | 7681.0 | ± | 286.9 | 261.0 | ± | 26.0 |
| 48 | #F | ALP(−) | 0.6 | ± | 0.3 | 0.0 | ± | 0.0 | 0.0 | ± | 0.0 | 8.2 | ± | 0.6 | 53887.9 | ± | 1343.2 | 13.3 | ± | 1.2 |
| 49 | #I | ALP(−) | 2.1 | ± | 0.6 | 0.0 | ± | 0.0 | 226.0 | ± | 17.7 | 0.0 | ± | 0.0 | 906.4 | ± | 231.6 | 7.2 | ± | 0.2 |
| 50 | #B | ALP(−) | 0.0 | ± | 0.0 | 0.0 | ± | 0.0 | 0.0 | ± | 0.0 | 0.0 | ± | 0.0 | 4461.3 | ± | 589.3 | 5.2 | ± | 0.4 |
| 51 | #H | ALP(−) | 2.1 | ± | 0.6 | 0.0 | ± | 0.0 | 226.0 | ± | 17.7 | 0.0 | ± | 0.0 | 906.4 | ± | 231.6 | 7.2 | ± | 0.2 |

Table 12 summarizes relative mRNA expression in clone-2-4 and 3-2. Total RNA was extracted from clones 2-4 and 3-2. Expression of ES cell marker genes were determined by qRT-PCR as described in Example 16 and 17. Both clone-2-4 and -3-2 showed ES cell marker gene expression. All expression values were normalized against human iPS clone-1-8 (day 94).

TABLE 12 relative mRNA expression in clone-2-4 and 3-2.

| | #3-2_day48 | #2-4_day59 | #1-8_day82 | #1-8_day94 |
|---|---|---|---|---|
| Nanog | 4.21 ± 1.11 | 2.88 ± 0.43 | 2.41 | 1.00 ± 0.24 |
| TERT | 1.52 ± 0.50 | 1.94 ± 0.14 | 0.69 | 1.00 ± 0.70 |
| GDF3 | 6.42 ± 0.16 | 6.65 ± 0.05 | 0.92 | 1.00 ± 0.49 |
| CYP26A1 | 72.45 ± 14.92 | 49.12 ± 0.06 | 62.50 | 1.00 ± 0.01 |
| TDGF1 | 2.55 ± 0.10 | 3.53 ± 0.05 | 3.53 | 1.00 ± 0.01 |
| Dnmt3b | 2.66 ± 0.04 | 0.96 ± 0.02 | 0.91 | 1.00 ± 0.01 |
| Foxd3 | 1.16 ± 0.08 | 0.59 ± 0.17 | 1.14 | 1.00 ± 0.18 |
| Zfp42 | 0.98 ± 0.15 | 0.76 ± 0.01 | 2.44 | 1.00 ± 0.02 |
| Myc | 6.14 ± 0.58 | 4.58 ± 0.16 | 3.82 | 1.00 ± 0.05 |
| Oct3/4 | 2.00 ± 0.07 | 1.08 ± 0.01 | 1.33 | 1.00 ± 0.00 |

INDUSTRIAL APPLICABILITY

Cells in a tissue that was lost in diseases etc. can be supplied by inducing human pluripotent cells from the undifferentiated stem cells harvested from a patient by using the induction method of the present invention, followed by inducing to differentiate into a necessary cell depending on diseases and then transplanting the cells to the patient. The undifferentiated stem cells of the present invention present in a human postnatal tissue can be used to search drugs that promote the induction from said undifferentiated stem cells to human pluripotent stem cells by using markers such as Tert, Nanog, Sox2, Oct3/4 and alkaline phosphatase that direct the induction to human pluripotent stem cells. Said drugs can be used in stead of gene introduction and can enhance the induction efficiency of human pluripotent stem cells.

What is claimed is:

1. A method for generating a human pluripotent stem cell, comprising the steps of:
   (i) introducing one or more retroviral vectors comprising a gene encoding Oct3/4, a gene encoding Sox2 and a gene encoding Klf4 into an isolated human post-natal cell; and
   (ii) culturing the cell of step (i) in the presence of an inhibitor of Rho kinase and/or a histone deacetylase inhibitor under conditions that maintain pluripotency and self-renewal, thereby generating a human pluripotent stem cell.

2. The method of claim 1, wherein the inhibitor of Rho kinase is Y-27632 or HA-1077.

* * * * *

SEQUENCE LISTING

<160> NUMBER OF SEQ ID NOS: 45

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agtctggctt atatccaaca cttcg                                           25

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 2
gactttgctt tccttggtca gg                                           22

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tacctcagcc tccagcagat                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgcgtcacac cattgctatt                                              20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agccagtctc accttcaacc gc                                           22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggagtagcag agggaggccg                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aaaccccagc acatcaactc                                              20

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 8
gtcattccct gggtggttc                                        19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttggagtgca atggtgtgat                                       20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tctgttcaca caggctccag                                       20

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggcgtccgcg ggaatgtact tc                                    22

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tggcttaggg gtggtctggc c                                     21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcagcgacca gtcctccgac t                                     21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
```
aacgtgggga aggcctgtgc                                          20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acagaacctg ctgcctgaat                                          20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agaaatgcct gaggaaagca                                          20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cttgacaatc gagtggctga                                          20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tcatccgtgg tgtagccata                                          20

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aacctgcacg actcctcgca ca                                       22

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aggatgcgca tggcgattcg                                          20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gagaaggaga agctggagca                                          20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aatagaaccc ccagggtgag                                          20

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agtagacggc atcgcagctt gg                                       22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggaagcttag ccaggtccga gg                                       22

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
caggagaacc ccaagatgc                                           19

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcagccgctt agcctcg                                             17

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
acactgcccc tctcacacat                                              20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cgggactatg gttgctgact                                              20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
accctgggtc ttgaggaagt                                              20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
acgatcgtct tcccctcttt                                              20

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctcaccctta ccgagtcggc g                                            21

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcagctgggg cacctgaacc                                              20

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tccagcttgt acctgcagga tctga                                          25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cctccagcag aaggtgatcc agact                                          25

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
agtagacggc atcgcagctt gg                                             22

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cctccagcag aaggtgatcc agact                                          25

<210> SEQ ID NO 37
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aggaagagag ggaatttaag gtgtatgtat ttttttattt                          40

<210> SEQ ID NO 38
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cagtaatacg actcactata gggagaaggc tataacccac ccctataatc ccaata        56

<210> SEQ ID NO 39
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aggaagagag gttaggttgg ttttaaattt ttgat                           35

<210> SEQ ID NO 40
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cagtaatacg actcactata gggagaaggc ttttataata aaaactctat caccttaaac    60
c                                                                    61

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aggaagagag tagtagggat tttttggatt ggttt                           35

<210> SEQ ID NO 42
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cagtaatacg actcactata gggagaaggc taaaactttt cccccactct tatattac    58

<210> SEQ ID NO 43
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
aggaagagag ggtaataaag tgagattttg ttttaaaaa                       39

<210> SEQ ID NO 44
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cagtaatacg actcactata gggagaaggc tccacccact aaccttaacc tctaa        55

```
<210> SEQ ID NO 45
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cttttgcatt acaatg                                                    16
```